(12) United States Patent
Qiu

(10) Patent No.: US 9,814,761 B2
(45) Date of Patent: Nov. 14, 2017

(54) COMPOSITIONS, METHODS AND ASSAYS COMPRISING AMYLIN OR AMLYIN ANALOGS FOR ABETA-PEPTIDE MEDIATED DISORDERS

(71) Applicant: TRUSTEES OF BOSTON UNIVERSITY, Boston, MA (US)

(72) Inventor: Wendy Wei Qiao Qiu, Brookline, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 14/388,485

(22) PCT Filed: Mar. 14, 2013

(86) PCT No.: PCT/US2013/031567
§ 371 (c)(1),
(2) Date: Sep. 26, 2014

(87) PCT Pub. No.: WO2013/151729
PCT Pub. Date: Oct. 10, 2013

(65) Prior Publication Data
US 2015/0051150 A1 Feb. 19, 2015

Related U.S. Application Data

(60) Provisional application No. 61/619,696, filed on Apr. 3, 2012.

(51) Int. Cl.
*A61K 38/00* (2006.01)
*A61K 38/22* (2006.01)
*A61K 45/06* (2006.01)
*G01N 33/68* (2006.01)

(52) U.S. Cl.
CPC ......... *A61K 38/22* (2013.01); *G01N 33/6896* (2013.01); *G01N 2333/4709* (2013.01); *G01N 2800/2821* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,686,411 | A | 11/1997 | Gaeta et al. |
| 5,998,367 | A | 12/1999 | Gaeta et al. |
| 6,087,334 | A | 7/2000 | Beeley et al. |
| 6,610,824 | B2 | 8/2003 | Gaeta et al. |
| 9,132,170 | B2 * | 9/2015 | Smith .................... A61K 38/22 |
| 2001/0007015 | A1 | 7/2001 | Kapurniotu et al. |
| 2008/0176804 | A1 | 7/2008 | Mack et al. |
| 2010/0221240 | A1 | 9/2010 | Kapurniotu et al. |
| 2010/0290985 | A1 | 11/2010 | Pardridge et al. |
| 2012/0019779 | A1 | 1/2012 | Legerton et al. |
| 2012/0071401 | A1 | 3/2012 | Roth et al. |
| 2012/0196796 | A1 | 8/2012 | Soares et al. |

FOREIGN PATENT DOCUMENTS

| | | | |
|---|---|---|---|
| WO | 02/24727 | A2 | 3/2002 |
| WO | 2005/066337 | A2 | 7/2005 |
| WO | 2006/083254 | A1 | 8/2006 |
| WO | 2008/002465 | A2 | 1/2008 |
| WO | 2009/048631 | A1 | 4/2009 |
| WO | 2009/070847 | A1 | 6/2009 |
| WO | WO2009091932 | * | 7/2009 ............. A61P 25/28 |

OTHER PUBLICATIONS

Demattos et al., PNAS, 98(15):8850-8855, (2001). "Pheripheral anti-a beta antibody alters CNS and plasma A beta clearance and decreases brain A beta burden in a mouse model of Alzheimer's disease."
Pathuri et al., Journal of Labelled Compounds and Radiopharmaceuticals, 53(4):186-191, (2010). "Radiosynthesis and in vivo evaluation of a F-18 labeled pancreatic islet amyloid inhibitor."
Thambisetty et al., Biomarkers in Medicine, 4(1):65-79 (2010). "Blood-based biomarkers of Alzheimer's disease: Challenging but feasible."
Zdrojewicz et al., Diabetologia Doświadczalna i Kliniczna, 6(4):169-172 (2006). "Amylin—structure, function, clinical meaning."
Banks et al., "Differential permeability of the blood-brain barrier to two pancreatic peptides: insulin and amylin", Peptides 19, 883-889 (1998).
Baron et al., "Novel peptides under development for the treatment of Type 1 and Type 2 diabetes mellitus", (2002) Curr. Drug Targets—Immune Endocr. Metabol. Disord. 2:63-82 (2002).
Bennett et al., "An insulin-degrading enzyme inhibitor decreases amylin degradation, increases amylin-induced cytotoxicity, and increases amyloid formation in insulinoma cell cultures", Diabetes 52:2315-2320 (2003).
Gotz et al., "Visions & Refelcetions: Common features between diabetes mellitus and alzheimer's disease", Cell Mol. Life Sci 66:1321-1325 (2009).
Lim et al., "Human but not rat amylin shares neurotoxic properties with a 42 in long-term hippocampal and cortical cultures", FEBS Letter 582:2188-2194 (2008).

(Continued)

*Primary Examiner* — Olga N Chernyshev
(74) *Attorney, Agent, or Firm* — Nixon Peabody LLP; Ronald I. Eisenstein; Srividya Subramanian

(57) ABSTRACT

Provided herein are methods of reducing and/or inhibiting A deposition or A plaque formation in the brain, and/or inhibiting or slowing the progression of disorders mediated by A deposition or A plaque formation using therapeutically effective amounts of amylin agonist compounds or pharmaceutical compositions comprising amylin agonist compounds. As demonstrated herein, amylin and amylin analog administration improves cognition, including memory. Also provided herein are non-invasive, inexpensive amylin or amylin analog challenge assays and methods and kits thereof for detecting the presence of plaques comprising A? peptide in the brain, and for identifying individuals at increased risk for Alzheimer's disease (AD) and/or amnestic mild cognitive impairment.

8 Claims, 16 Drawing Sheets

(56) References Cited

OTHER PUBLICATIONS

Progress Report on Alzheimer's Disease, National Institute on Aging/National Institute of Health (1999).
Qui et al, "Insulin-degrading enzyme regulates extracellular levels of amyloid beta-protein by degradation", J Biol Chem 273:32730-32738 (1998).
Shen et al., "Structures of human insulin-degrading enzyme reveal a new substrate recognition mechanism", Nature 443:870-874 (2006).
Young A.A., "Amylin's physiology and its role in diabetes", Curr. Opin. in Endocrinology and Diabetes 4:282-290 (1997).
Adler et al., "Neuroprotective effects of the amylin analogue pramlintide on Alzheimer's disease pathogenesis and cognition", Neurobiology of Aging, 35(4): 793-801 (2013).
Andreetto et al., "Identification of Hot Regions of the A(beta)—IAPP Interaction Interface as High-Affinity Binding Sites in both Cross- and Self-Association", Angewandte Chemie International Edition, 49(17): 3081-3085 (2010).
Andreetto et al., "Dissecting the Role of Single Regions of an IAPPC Mimic and IAPP in Inhibition of A(beta)40 Amyloid Formation and Cytotoxicity", Chembiochem, 12(9): 1313-1322 (2011).
Kapurniotu et al., "Conformational Restriction via Cyclization in sz-Amyloid Peptide Asz(1-28) Leads to an Inhibitor of Asz(1-28) Amyloidogenesis and Cytotoxicity", Current Biology, 10(2): 149-159 (2003).
Rezaei-Ghaleh et al., "Interaction between Amyloid Beta Peptide and an Aggregation Blocker Peptide Mimicking Islet Amyloid Polypeptide", PLoS One, 6(5): e20289 (2011).
Schmitz et al., "Amylin AgonistsL A Novel Approach in the Treatment of Diabetes", Diabetes, 53(3): S233-S238 (2004).
Yan et al., "IAPP Mimic Blocks A(beta) Cytotocix Self-Assembly: Cross-Suppression of Amyloid Toxicity of A9beta) And IAPP Suggests a Molecular Link between Alzheimer's Disease and Type I Diabetes", Angewandte Chemie International Edition, 46(8): 1246-1252 (2007).

\* cited by examiner

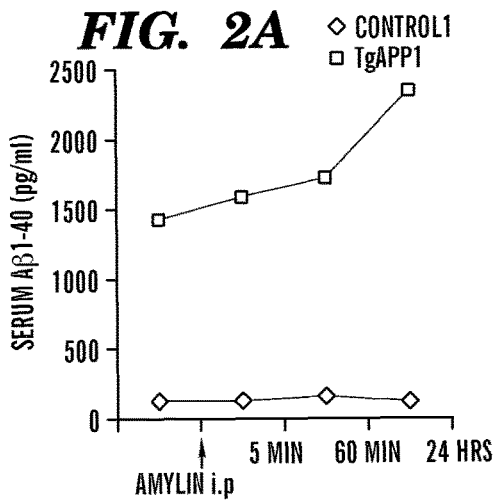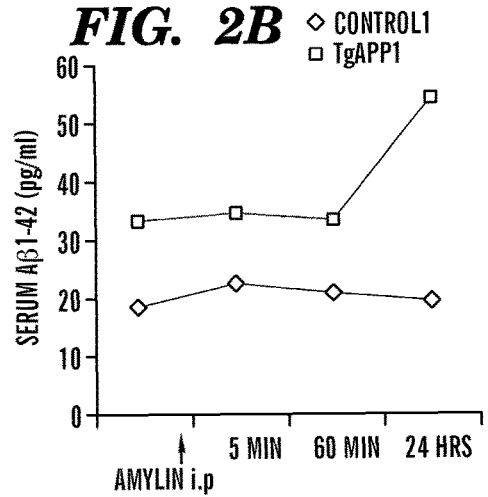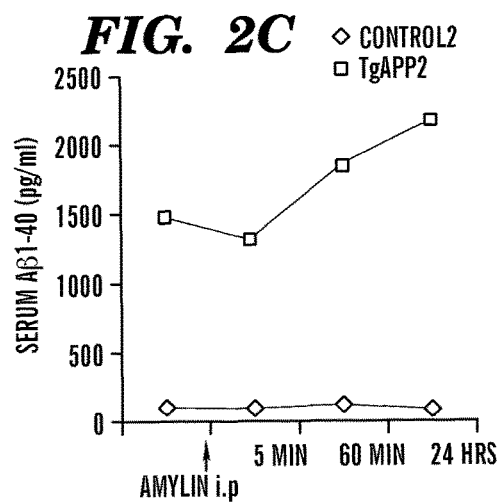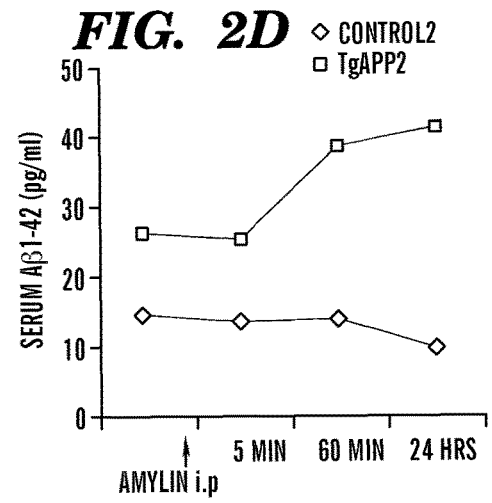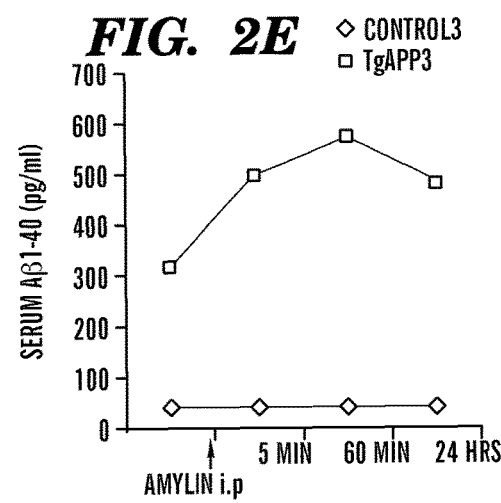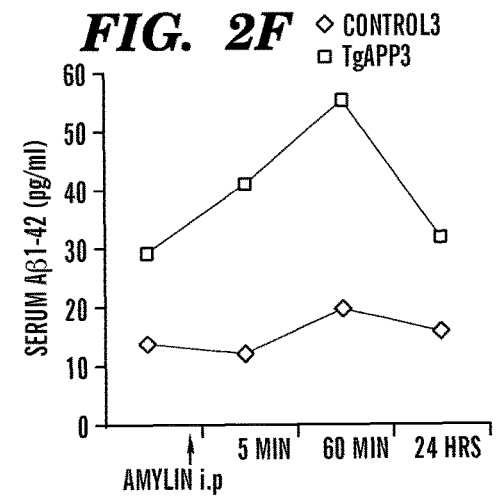

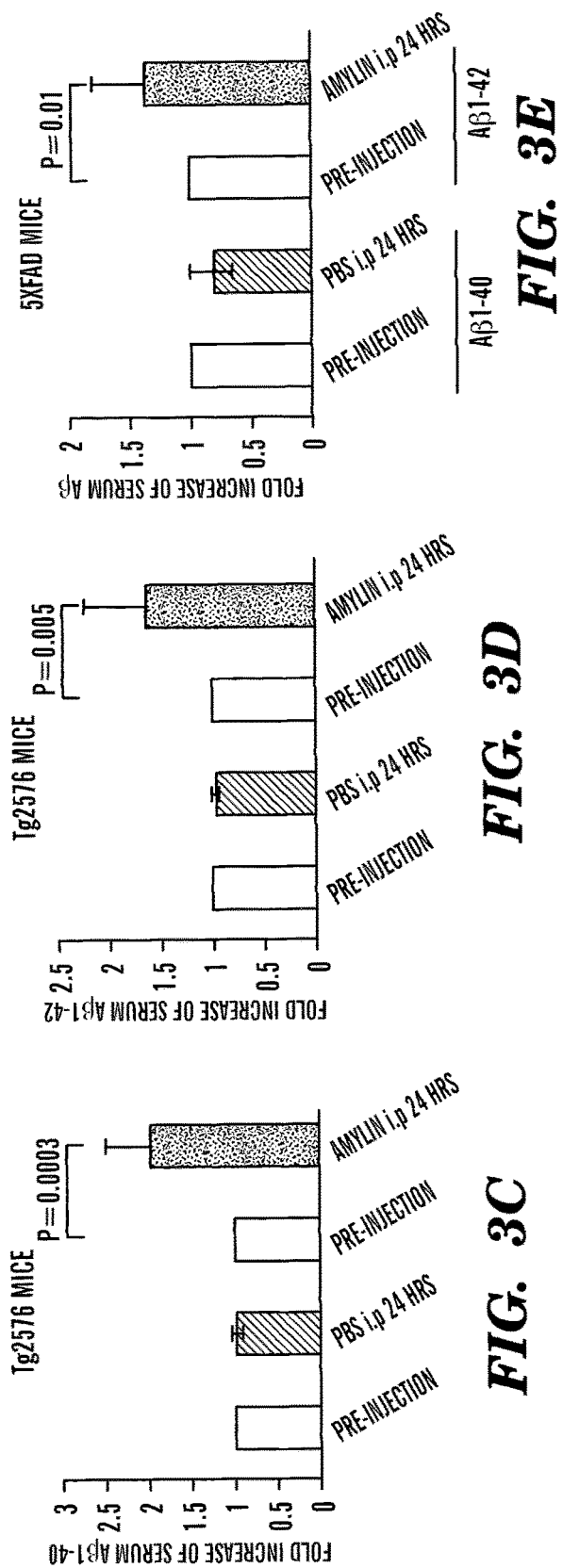

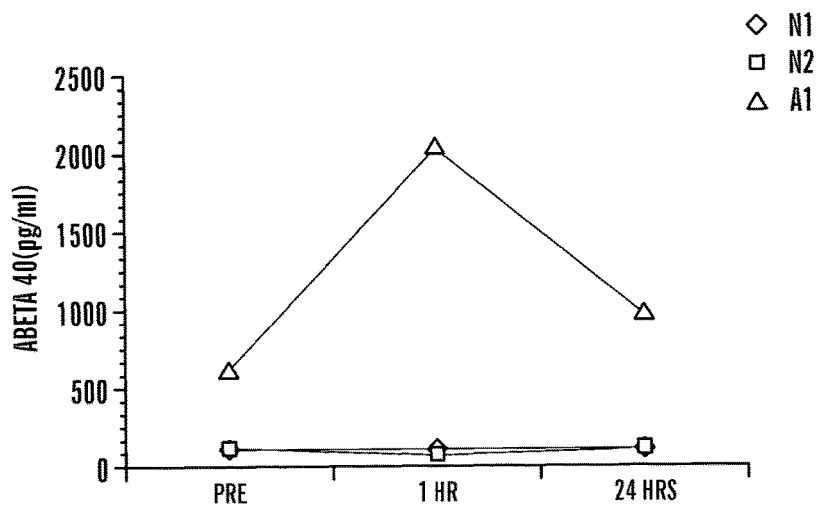
FIG. 7
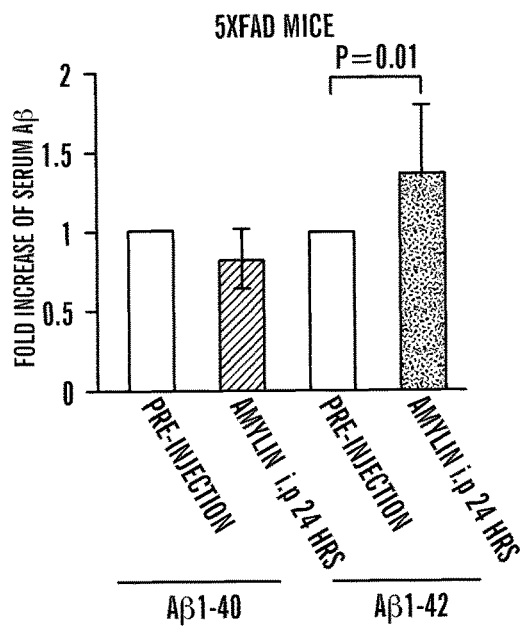 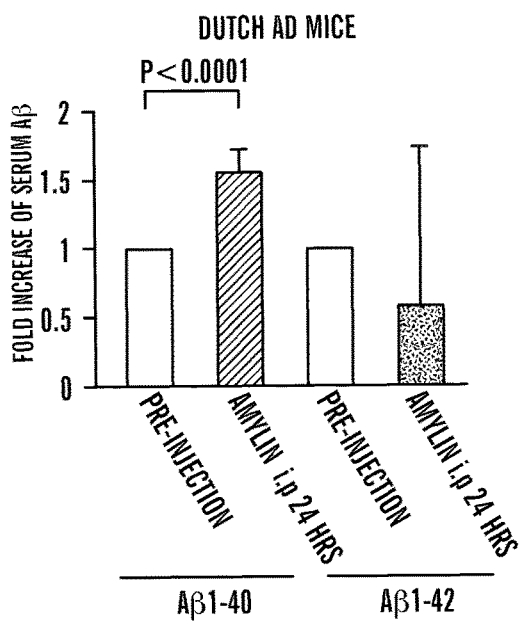
FIG. 8A  FIG. 8B

AMYLIN: KCNTATCATQRLANFLVH-SSNNFGAIL-SSTNVGSNTY

Aβ42: DAEFRHDSGYEVHHQKLVFFAEDVGSNKGAIIGLMVGGVVIA

γ SECRETASE INHIBITOR SEQUENCE
Li ET AL. 2010

SEQUENCE LISTING

```
<160> NUMBER OF SEQ ID NOS: 45

<210> SEQ ID NO 1
<211> LENGTH: 40
<212> TYPE: PRT
<213> ORGANISM: Unknown
<220> FEATURE:
<223> OTHER INFORMATION: Description of Unknown: Amyloid
      beta polypeptide

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 2
<211> LENGTH: 42
<212> TYPE: PRT
<213> ORGANISM: Unknown
<220> FEATURE:
```

<223> OTHER INFORMATION: Description of Unknown: Amyloid
      beta polypeptide

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 3
<211> LENGTH: 37
<212> TYPE: PRT
<213> ORGANISM: Homo sapiens

<400> SEQUENCE: 3

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 4
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Lys Cys Asn Thr Ala Thr Cys Ala Thr Asn Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35

<210> SEQ ID NO 5
<211> LENGTH: 37
<212> TYPE: PRT
<213> ORGANISM: Rattus sp.

<400> SEQUENCE: 5

Lys Cys Asn Thr Ala Thr Cys Ala Thr Gln Arg Leu Ala Asn Phe Leu
1               5                   10                  15

Val Arg Ser Ser Asn Asn Phe Gly Pro Val Leu Pro Pro Thr Asn Val
            20                  25                  30

Gly Ser Asn Thr Tyr
        35

<210> SEQ ID NO 6
<211> LENGTH: 37
<212> TYPE: PRT
<213> ORGANISM: Unknown
<220> FEATURE:
<223> OTHER INFORMATION: Description of Unknown: Monkey
      amylin polypeptide

<400> SEQUENCE: 6

-continued

Lys Cys Asn Thr Ala Thr Cys Ala Thr Gln Arg Leu Ala Asn Phe Leu
1               5                   10                  15

Arg His Ser Ser Asn Asn Phe Gly Thr Ile Leu Ser Thr Asn Val
            20                  25                  30

Gly Ser Asp Thr Tyr
        35

<210> SEQ ID NO 7
<211> LENGTH: 37
<212> TYPE: PRT
<213> ORGANISM: Felis sp.

<400> SEQUENCE: 7

Lys Cys Asn Thr Ala Thr Cys Ala Thr Gln Arg Leu Ala Asn Phe Leu
1               5                   10                  15

Ile Arg Ser Ser Asn Asn Leu Gly Ala Ile Leu Ser Pro Thr Asn Val
            20                  25                  30

Gly Ser Asn Thr Tyr
        35

<210> SEQ ID NO 8
<211> LENGTH: 37
<212> TYPE: PRT
<213> ORGANISM: Canis sp.

<400> SEQUENCE: 8

Lys Cys Asn Thr Ala Thr Cys Ala Thr Gln Arg Leu Ala Asn Phe Leu
1               5                   10                  15

Val Arg Thr Ser Asn Asn Leu Gly Ala Ile Leu Ser Pro Thr Asn Val
            20                  25                  30

Gly Ser Asn Thr Tyr
        35

<210> SEQ ID NO 9
<211> LENGTH: 37
<212> TYPE: PRT
<213> ORGANISM: Mus sp.

<400> SEQUENCE: 9

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Asn Val
            20                  25                  30

Gly Ser Asn Thr Tyr
        35

<210> SEQ ID NO 10
<211> LENGTH: 37
<212> TYPE: PRT
<213> ORGANISM: Unknown
<220> FEATURE:
<223> OTHER INFORMATION: Description of Unknown: Hamster
      amylin polypeptide

<400> SEQUENCE: 10

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Ser Pro Thr Asn Val
            20                  25                  30

Gly Ser Asn Thr Tyr
        35

<210> SEQ ID NO 11
<211> LENGTH: 37
<212> TYPE: PRT
<213> ORGANISM: Cavia porcellus

<400> SEQUENCE: 11

Lys Cys Asn Thr Ala Thr Cys Ala Thr Gln Arg Leu Thr Asn Phe Leu
1               5                   10                  15

Val Arg Ser Ser His Asn Leu Gly Ala Ala Leu Leu Pro Thr Asn Val
            20                  25                  30

Gly Ser Asn Thr Tyr
        35

<210> SEQ ID NO 12
<211> LENGTH: 37
<212> TYPE: PRT
<213> ORGANISM: Octodon degus

<400> SEQUENCE: 12

Lys Cys Asn Thr Ala Thr Cys Ala Thr Gln Arg Leu Thr Asn Phe Leu
1               5                   10                  15

Val Arg Ser Ser Asn Asn Leu Gly Ala Ala Leu Leu Pro Thr Lys Val
            20                  25                  30

Gly Ser Asn Thr Tyr
        35

<210> SEQ ID NO 13
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Cys Asn Thr Ala Thr Cys Ala Thr Gln Arg Leu Ala Asn Phe Leu Val
1               5                   10                  15

His Ser Ser Asn Asn Phe Gly Ala Ile Leu Ser Ser Thr Asn Val Gly
            20                  25                  30

Ser Asn Thr Tyr
        35

<210> SEQ ID NO 14
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Lys Cys Asn Thr Ala Thr Cys Ala Thr Gln Arg Leu Ala Asn Phe Leu
1               5                   10                  15

Ile Arg Ser Ser Asn Asn Leu Gly Ala Ile Leu Ser Ser Thr Asn Val
            20                  25                  30

Gly Ser Asn Thr Tyr
        35

<210> SEQ ID NO 15
<211> LENGTH: 37
<212> TYPE: PRT

<213> ORGANISM: Artificial Sequence
<220> FEATURE:
<223> OTHER INFORMATION: Description of Artificial Sequence: Synthetic
     polypeptide

<400> SEQUENCE: 15

Lys Cys Asn Thr Ala Thr Cys Ala Thr Gln Arg Leu Ala Asn Phe Leu
1               5                   10                  15

Ile Arg Ser Ser Asn Asn Leu Gly Ala Val Leu Ser Pro Thr Asn Val
            20                  25                  30

Gly Ser Asn Thr Tyr
        35

<210> SEQ ID NO 16
<211> LENGTH: 37
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 16

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Ser Ser Thr Asn Val
            20                  25                  30

Gly Ser Asn Thr Tyr
        35

<210> SEQ ID NO 17
<211> LENGTH: 37
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 17

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Pro Ser Thr Asn Val
            20                  25                  30

Gly Ser Asn Thr Tyr
        35

<210> SEQ ID NO 18
<211> LENGTH: 37
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 18

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Pro Thr Asn Val
            20                  25                  30

Gly Ser Asn Thr Tyr
        35

<210> SEQ ID NO 19
<211> LENGTH: 37

-continued

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Lys Cys Asn Thr Ala Thr Cys Ala Thr Gln Arg Leu Thr Asn Phe Leu
1               5                   10                  15

Val Arg Ser Ser His Asn Leu Gly Ala Ala Leu Ser Pro Thr Asp Val
            20                  25                  30

Gly Ser Asn Thr Tyr
        35

<210> SEQ ID NO 20
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Lys Cys Asn Thr Ala Thr Cys Ala Thr Gln Arg Leu Thr Asn Phe Leu
1               5                   10                  15

Val His Ser Ser His Asn Leu Gly Ala Ala Leu Leu Pro Thr Asp Val
            20                  25                  30

Gly Ser Asn Thr Tyr
        35

<210> SEQ ID NO 21
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Lys Cys Asn Thr Ala Thr Cys Ala Thr Gln Arg Leu Thr Asn Phe Leu
1               5                   10                  15

Val His Ser Ser His Asn Leu Gly Ala Ala Leu Ser Pro Thr Asp Val
            20                  25                  30

Gly Ser Asn Thr Tyr
        35

<210> SEQ ID NO 22
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Cys Asn Thr Ala Thr Cys Ala Thr Gln Arg Leu Thr Asn Phe Leu Val
1               5                   10                  15

His Ser Ser His Asn Leu Gly Ala Ala Leu Ser Pro Thr Asp Val Gly
            20                  25                  30

Ser Asn Thr Tyr
        35

<210> SEQ ID NO 23
```

```
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Cys Asn Thr Ala Thr Cys Ala Thr Gln Arg Leu Ala Asn Phe Leu Val
1               5                   10                  15

His Ser Ser Asn Asn Phe Gly Pro Ile Leu Pro Pro Thr Asn Val Gly
            20                  25                  30

Ser Asn Thr Tyr
        35

<210> SEQ ID NO 24
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Lys Cys Asn Thr Ala Thr Cys Ala Thr Gln Arg Leu Ala Asn Phe Leu
1               5                   10                  15

Val Arg Ser Ser Asn Asn Phe Gly Pro Ile Leu Pro Pro Thr Asn Val
            20                  25                  30

Gly Ser Asn Thr Tyr
        35

<210> SEQ ID NO 25
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Cys Asn Thr Ala Thr Cys Ala Thr Gln Arg Leu Ala Asn Phe Leu Val
1               5                   10                  15

Arg Ser Ser Asn Asn Phe Gly Pro Val Leu Pro Pro Thr Asn Val Gly
            20                  25                  30

Ser Asn Thr Tyr
        35

<210> SEQ ID NO 26
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35
```

```
<210> SEQ ID NO 27
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Lys Cys Asn Thr Ala Thr Cys Ala Thr Gln Arg Leu Ala Asn Phe Leu
1               5                   10                  15

Ile His Ser Ser Asn Asn Phe Gly Pro Ile Leu Pro Pro Thr Asn Val
            20                  25                  30

Gly Ser Asn Thr Tyr
        35

<210> SEQ ID NO 28
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Lys Cys Asn Thr Ala Thr Cys Ala Thr Gln Arg Leu Ala Asn Phe Leu
1               5                   10                  15

Val His Ser Ser Asn Asn Leu Gly Pro Val Leu Pro Pro Thr Asn Val
            20                  25                  30

Gly Ser Asn Thr Tyr
        35

<210> SEQ ID NO 29
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Lys Cys Asn Thr Ala Thr Cys Ala Thr Gln Arg Leu Ala Asn Phe Leu
1               5                   10                  15

Val Arg Ser Ser Asn Asn Leu Gly Pro Ile Leu Pro Pro Thr Asn Val
            20                  25                  30

Gly Ser Asn Thr Tyr
        35

<210> SEQ ID NO 30
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Lys Cys Asn Thr Ala Thr Cys Ala Thr Gln Arg Leu Ala Asn Phe Leu
1               5                   10                  15

Ile His Ser Ser Asn Asn Leu Gly Pro Ile Leu Pro Pro Thr Asn Val
            20                  25                  30

Gly Ser Asn Thr Tyr
        35
```

<210> SEQ ID NO 31
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Cys Asn Thr Ala Thr Cys Ala Thr Gln Arg Leu Ala Asn Phe Leu Ile
1               5                   10                  15

His Ser Ser Asn Asn Leu Gly Pro Ile Leu Pro Pro Thr Asn Val Gly
            20                  25                  30

Ser Asn Thr Tyr
        35

<210> SEQ ID NO 32
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Lys Cys Asn Thr Ala Thr Cys Ala Thr Gln Arg Leu Ala Asn Phe Leu
1               5                   10                  15

Ile Arg Ser Ser Asn Asn Arg Gly Pro Val Leu Pro Pro Thr Asn Val
            20                  25                  30

Gly Ser Asn Thr Tyr
        35

<210> SEQ ID NO 33
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Lys Cys Asn Thr Ala Thr Cys Ala Thr Gln Arg Leu Thr Asn Phe Leu
1               5                   10                  15

Val Arg Ser Ser His Asn Leu Gly Pro Ala Leu Pro Pro Thr Asp Val
            20                  25                  30

Gly Ser Asn Thr Tyr
        35

<210> SEQ ID NO 34
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Lys Cys Asn Thr Ala Thr Cys Ala Thr Gln Arg Leu Ala Asn Phe Leu
1               5                   10                  15

Val Arg Ser Ser Asn Asn Phe Gly Pro Ile Leu Pro Ser Thr Asn Val
            20                  25                  30

Gly Ser Asn Thr Tyr
        35

```
<210> SEQ ID NO 35
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Cys Asn Thr Ala Thr Cys Ala Thr Gln Arg Leu Ala Asn Phe Leu Val
1               5                   10                  15

Arg Ser Ser Asn Asn Phe Gly Pro Ile Leu Pro Ser Thr Asn Val Gly
            20                  25                  30

Ser Asn Thr Tyr
        35

<210> SEQ ID NO 36
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Lys Cys Asn Thr Ala Thr Cys Ala Thr Gln Arg Leu Ala Asn Phe Leu
1               5                   10                  15

Val Arg Ser Ser Asn Asn Leu Gly Pro Ile Leu Pro Ser Thr Asn Val
            20                  25                  30

Gly Ser Asn Thr Tyr
        35

<210> SEQ ID NO 37
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Lys Cys Asn Thr Ala Thr Cys Ala Thr Gln Arg Leu Ala Asn Phe Leu
1               5                   10                  15

Val His Ser Ser Asn Asn Leu Gly Pro Val Leu Pro Ser Thr Asn Val
            20                  25                  30

Gly Ser Asn Thr Tyr
        35

<210> SEQ ID NO 38
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Cys Asn Thr Ala Thr Cys Ala Thr Gln Arg Leu Ala Asn Phe Leu Val
1               5                   10                  15

His Ser Ser Asn Asn Leu Gly Pro Val Leu Pro Ser Thr Asn Val Gly
            20                  25                  30

Ser Asn Thr Tyr
```

```
<210> SEQ ID NO 39
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Ser Thr Asn Val
            20                  25                  30

Gly Ser Asn Thr Tyr
        35

<210> SEQ ID NO 40
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Ser Thr Asn Val
            20                  25                  30

Gly Ser Asn Thr Tyr
        35

<210> SEQ ID NO 41
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Lys Cys Asn Thr Ala Thr Cys Ala Thr Gln Arg Leu Thr Asn Phe Leu
1               5                   10                  15

Val Arg Ser Ser His Asn Leu Gly Ala Ile Leu Pro Pro Thr Asp Val
            20                  25                  30

Gly Ser Asn Thr Tyr
        35

<210> SEQ ID NO 42
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Pro Pro Thr Asn Val
            20                  25                  30
```

```
Gly Ser Asn Thr Tyr
        35

<210> SEQ ID NO 43
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Ser Pro Thr Asn Val
                20                  25                  30

Gly Ser Asn Thr Tyr
        35

<210> SEQ ID NO 44
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
                20                  25                  30

<210> SEQ ID NO 45
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala
        35                  40
```

COMPOSITIONS, METHODS AND ASSAYS COMPRISING AMYLIN OR AMLYIN ANALOGS FOR ABETA-PEPTIDE MEDIATED DISORDERS

CROSS-REFERENCE TO RELATED APPLICATIONS

This Application is a 35 U.S.C. §371 National Phase Entry Application of International Application No. PCT/US2013/031567 filed Mar. 14, 2013, which designates the U.S., and which claims benefit under 35 U.S.C. §119(e) of U.S. Provisional Patent Application Serial No. 61/619,696 filed on 3 Apr. 2012, the contents of each of which are incorporated herein by reference in their entirety.

GOVERNMENT SUPPORT

This invention was made with Government support under Grant No. AG031171 awarded by the National Institutes of Health. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Apr. 1, 2013, is named 701586-069642_US_SL.txt and is 20,846 bytes in size.

FIELD OF THE INVENTION

The invention relates to methods of treatment, amylin challenge assays and methods for detecting Aβ in the brain based on amylin or amyline analogs.

BACKGROUND OF THE INVENTION

As the population ages in the United States, it is predicted that there will be more than 15 million Alzheimer's disease (AD) patients by 2050 and it will cost billions of dollars to take care of them Unlike other disorders, there are no simple, non-invasive or minimally invasive, sensitive, specific assays for diagnosing AD and identifying individuals who are at an increased risk for AD, like the blood PSA test for prostate cancer and the blood cholesterol test for atherosclerotic diseases.

Alzheimer's disease is a leading cause of dementia in the elderly, affecting 5-10% of the population over the age of 65 years (A Guide to Understanding Alzheimer's Disease and Related Disorders, Jorm, ed., New York University Press, New York, 1987). In Alzheimer's disease, the parts of the brain essential for cognitive processes such as memory, attention, language, and reasoning degenerate, robbing victims of much that makes us human, including independence. In some forms of Alzheimer's disease, onset can first be seen in middle age, but more commonly, symptoms appear from the 65 and onwards. Alzheimer's disease today affects 4-5 million Americans, with slightly more than half of these people receiving care at home, while the others are in many different health care institutions. The prevalence of Alzheimer's disease and other dementias doubles every 5 years beyond the age of 65, and recent studies indicate that nearly 50% of all people age 85 and older have symptoms of Alzheimer's disease (1999 Progress Report on Alzheimer's Disease, National Institute on Aging/National Institute of Health). 13% (33 million people) of the total population of the United States are age 65 and older, and this percentage will climb to 20% by the year 2025 (1999 Progress Report on Alzheimer's Disease).

Alzheimer's disease also puts a heavy economic burden on society. A recent study estimated that the cost of caring for one Alzheimer's disease patient with severe cognitive impairments at home or in a nursing home, is more than $47,000 per year (A Guide to Understanding Alzheimer's Disease and Related Disorders). For a disease that can span from 2 to 20 years, the overall cost of Alzheimer's disease to families and to society is staggering. The annual economic toll of Alzheimer's disease in the United States in terms of health care expenses and lost wages of both patients and their caregivers is estimated at $80 to $100 billion (1999 Progress Report on Alzheimer's Disease).

SUMMARY OF THE INVENTION

Amylin is a peptide hormone associated with metabolism and glucose regulation, and its analog, pramlintide, is used clinically and has been shown to reduce post-prandial plasma glucose concentrations. As demonstrated herein, the inventors have discovered that amylin or an amylin analog can serve as a treatment for Alzheimer's disease and conditions relating to increased Aβ peptide in the brain, based, in part, on data from animal models. These data demonstrated that repeated administration of amylin or an amylin analog has long-term effects on acquisition and retention of memory, thus indicating that amylin or amylin analog administration can be used for the treatment of Alzheimer's disease and conditions relating to increased Aβ peptide in the brain.

The inventors have also discovered that amylin or amylin analogs can be used in assays, in vitro and ex vivo methods, and kits for detecting the presence of plaques comprising Aβ peptide in the brain, and for identifying individuals at increased risk for Alzheimer's disease (AD) and/or amnestic mild cognitive impairment. The inventors discovered that there is a significant positive correlation between the concentrations of amylin and Aβ1-40 or Aβ1-42 in plasma samples from human subjects with AD or amnestic MCI, but not in control subjects. As demonstrated herein, the inventors showed that intraperitoneal or subcutaneous injection of amylin or an amylin analog in mice and humans, respectively, results in increased blood levels of Aβ1-42 peptide in subjects with Alzheimer's disease. Until the discoveries by the inventors described herein, determination and diagnosis of amyloid associated diseases, such as Alzheimer's disease, has had little success, and has required complicated, expensive, and/or invasive tools and methods. In contrast to the standard of care determination and diagnosis of amyloid associated diseases, such as Alzheimer's disease, the assays and methods described herein are non-invasive, inexpensive, and require only an amylin or amylin analog challenge as part of a simple blood test or assay.

Accordingly, provided herein, in some aspects, are methods for reducing Aβ peptide deposition in the brain comprising administering to a subject having increased Aβ peptide deposition in the brain a therapeutically effective amount of amylin or an amylin analog.

In some aspects, provided herein are methods for inhibiting progression of Alzheimer's disease or amnestic mild cognitive impairment comprising administering to a subject having or at risk for Alzheimer's disease or amnestic mild cognitive a therapeutically effective amount of amylin or an amylin analog.

In some embodiments of these methods and all such methods described herein, the administering is at least once a week.

In some embodiments of these methods and all such methods described herein, the administering is at least twice a week.

In some embodiments of these methods and all such methods described herein, the administering is at least three times a week.

In some embodiments of these methods and all such methods described herein, the administering is at least four times a week.

In some embodiments of these methods and all such methods described herein, the administering is daily.

In some embodiments of these methods and all such methods described herein, the administering is performed by injection. In some embodiments, the injection is a systemic injection.

In some embodiments of these methods and all such methods described herein, the method further comprises determining the amount or quantity of Aβ peptide in a biological sample obtained from the subject within 72 hours of said administering. In some embodiments, the determining is within 24 hours of said administering. In some embodiments of these methods, the determining is within 4 hours of said administering.

In some embodiments of these methods and all such methods described herein, the biological sample is obtained from the subject within 24 hours of said administering.

In some embodiments of these methods and all such methods described herein, the biological sample is obtained from the subject within 4 hours of said administering.

In some embodiments of these methods and all such methods described herein, the biological sample is a blood sample, a serum sample, or a plasma sample.

In some embodiments of these methods and all such methods described herein, the Aβ peptide is Aβ42 of SEQ ID NO: 2.

In some embodiments of these methods and all such methods described herein, the amylin or amylin analog administered to the subject comprises a sequence of SEQ ID NO: 3, SEQ ID NO: 4, or SEQ ID NOs: 13-44.

In some embodiments of these methods and all such methods described herein, the amylin or amylin analog is administered as a unit dose composition.

In some embodiments of these methods and all such methods described herein, the subject having increased Aβ peptide deposition in the brain has or is at risk for Alzheimer's disease or amnestic mild cognitive impairment (aMCI).

In some embodiments of these methods and all such methods described herein, the method further comprises administering to the subject a cholinesterase inhibitor. In some embodiments of these methods, the cholinesterase inhibitor is galantamine, rivastigmine, or donepezil.

In some embodiments of these methods and all such methods described herein, the method further comprises administering to the subject an N-methyl D-aspartate (NMDA) antagonist. In some embodiments of these methods, the N-methyl D-aspartate (NMDA) antagonist is memantine.

Also provided herein, in some aspects, are assays for selecting a therapy for a subject having or at risk for Aβ peptide deposition in the brain, the assay comprising:

subjecting a biological sample, obtained from a subject administered an amylin or amylin analog challenge within 72 hours prior to collection of the biological sample, to an assay that determines the amount of Aβ peptide in the biological sample;

determining the amount of Aβ peptide in the biological sample; and selecting an amylin or amylin analog therapy for the subject when the determined amount of Aβ peptide in the biological sample is increased relative to a reference value; or not selecting an amylin or amylin analog therapy for the subject when the determined amount of Aβ peptide in the biological sample is below a reference value.

In some embodiments of these assays and all such assays described herein, the assay further comprises, when the determined amount of Aβ peptide in the biological sample is increased relative to a reference value, the step of treating the subject with amylin or an amylin analog therapy. In some embodiments of these assays, the treating is at least once a week. In some embodiments of these assays, the treating is at least twice a week. In some embodiments of these assays, the treating is at least three times a week. In some embodiments of these assays, the treating is at least four times a week. In some embodiments of these assays, the treating is daily.

In some embodiments of these assays and all such assays described herein, the biological sample is obtained from the subject within 24 hours of administration to the subject of the amylin or amylin analog challenge.

In some embodiments of these assays and all such assays described herein, the biological sample is obtained from the subject within 4 hours of administration to the subject of the amylin or amylin analog challenge.

In some embodiments of these assays and all such assays described herein, the biological sample is a blood sample, a serum sample, or a plasma sample.

In some embodiments of these assays and all such assays described herein, the Aβ peptide is Aβ42 of SEQ ID NO: 2.

In some embodiments of these assays and all such assays described herein, the amylin or amylin analog administered to the subject prior to the collection of the biological sample comprises a sequence of SEQ ID NO: 3, SEQ ID NO: 4, or SEQ ID NOs: 13-44.

In some embodiments of these assays and all such assays described herein, the subject having or at risk for Aβ peptide deposition in the brain has or is at risk for Alzheimer's disease or amnestic mild cognitive impairment (aMCI).

In some embodiments of these assays and all such assays described herein, the determined amount of Aβ peptide in the biological sample is increased by at least one standard deviation above the reference value.

In some embodiments of these assays and all such assays described herein, the determined amount of Aβ peptide in the biological sample is increased by at least two standard deviations above the reference value.

Also provided herein, in some aspects, are methods for selecting a therapy for a subject having or at risk for Aβ peptide deposition in the brain, the method comprising:

a. subjecting a biological sample, obtained from a subject administered an amylin or amylin analog challenge within 72 hours prior to collection of the biological sample, to an assay or method that determines the amount of Aβ peptide in the biological sample;

b. determining the amount of Aβ peptide in the biological sample; and c. selecting an amylin or amylin analog therapy for the subject when the determined amount of Aβ peptide in the biological sample is increased relative to a reference value; or not selecting an amylin or amylin analog therapy for the subject when the determined amount of Aβ peptide in the biological sample is below a reference value.

In some embodiments of these methods and all such methods described herein, the determined amount of Aβ peptide in the biological sample is increased by at least one standard deviation above the reference value.

In some embodiments of these methods and all such methods described herein, the determined amount of Aβ peptide in the biological sample is increased by at least two standard deviations above the reference value.

In some embodiments of these methods and all such methods described herein, the method further comprises, when the determined amount of Aβ peptide in the biological sample is increased relative to a reference value, the step of treating the subject with amylin or an amylin analog therapy. In some embodiments of these methods, the treating is at least once a week. In some embodiments of these methods, the treating is at least twice a week. In some embodiments of these methods, the treating is at least three times a week. In some embodiments of these methods, the treating is at least four times a week. In some embodiments of these methods, the treating is daily.

In some embodiments of these methods and all such methods described herein, the biological sample is obtained from the subject within 24 hours of administration to the subject of the amylin or amylin analog challenge.

In some embodiments of these methods and all such methods described herein, the biological sample is obtained from the subject within 4 hours of administration to the subject of the amylin or amylin analog challenge.

In some embodiments of these methods and all such methods described herein, the biological sample is a blood sample, a serum sample, or a plasma sample.

In some embodiments of these methods and all such methods described herein, the Aβ peptide is Aβ42 of SEQ ID NO: 2.

In some embodiments of these methods and all such methods described herein, the amylin or amylin analog administered to the subject prior to the collection of the biological sample comprises a sequence of SEQ ID NO: 3, SEQ ID NO: 4, or SEQ ID NOs: 13-44.

In some embodiments of these methods and all such methods described herein, the subject having or at risk for Aβ peptide deposition in the brain has or is at risk for Alzheimer's disease or amnestic mild cognitive impairment (aMCI).

Also provided herein, in some aspects, are radiotracer compositions comprising an amylin or amylin analog labeled with a radionuclide.

In some embodiments of these compositions and all such composition described herein, the amylin or amylin analog comprises a sequence of SEQ ID NO: 3, SEQ ID NO: 4, or SEQ ID NOs: 13-44.

In some embodiments of these compositions and all such composition described herein, the radionuclide is fluorine-18 or rubidium-82.

Provided herein, in some aspects, are assays comprising:
a. measuring or quantifying the amount of Aβ peptide in a biological sample obtained from a subject administered an amylin or amylin analog challenge within 72 hours prior to collection of the biological sample; and
b. identifying the subject as having increased Aβ peptide in the brain and selecting a therapy if the measured or quantified amount of Aβ peptide is increased relative to a reference value.

Provided herein, in some aspects, are assays comprising:
a. measuring or quantifying the amount of Aβ peptide in a first biological sample obtained from a subject prior to administration of an amylin or amylin analog challenge to the subject;
b. measuring or quantifying the amount of Aβ peptide in a second biological sample obtained from the subject within 72 hours of administration of an amylin or amylin analog challenge; and
c. identifying the subject as having increased Aβ peptide in the brain and selecting a therapy if the amount of Aβ peptide in the second biological sample is increased relative to the first biological sample.

Provided herein, in some aspects, are assays for selecting a therapy for a subject having or at risk for Alzheimer's disease or amnestic mild cognitive impairment, such assays comprising:
a. measuring or quantifying the amount of Aβ peptide in a biological sample obtained from a subject administered an amylin or amylin analog challenge within 72 hours prior to collection of the biological sample; and
b. selecting a therapy for the subject having or at risk for Alzheimer's disease or amnestic mild cognitive impairment if the amount of Aβ peptide measured or quantified is increased relative to a reference value.

Provided herein, in some aspects, are assays for selecting a therapy for a subject having or at risk for Alzheimer's disease or amnestic mild cognitive impairment comprising:
a. measuring or quantifying the amount of Aβ peptide in a first biological sample obtained from a subject prior to administration of an amylin or amylin analog challenge to the subject;
b. measuring or quantifying the amount of Aβ peptide in a second biological sample obtained from the subject within 72 hours of administration of an amylin or amylin analog challenge; and
c. identifying the subject as having increased Aβ peptide in the brain and optionally selecting a therapy if the amount of Aβ peptide in the second biological sample is increased relative to the first biological sample.

Provided herein, in some aspects, are assays for identifying the presence of plaques comprising Aβ peptide in a subject comprising:
a. measuring or quantifying the amount of Aβ peptide in a biological sample obtained from a subject administered an amylin or amylin analog challenge within 72 hours prior to collection of the biological sample; and
b. identifying the subject as having plaques comprising Aβ peptide if the amount of Aβ peptide is increased relative to a reference value.

In some embodiments of these assays, the reference value is the value of Aβ peptide in a biological sample from said subject prior to administration of the amylin or amylin analog challenge.

In some embodiments of these assays and all such assays described herein, the amount of Aβ peptide in the biological sample is increased by at least one standard deviation above the reference value or first biological sample.

In some embodiments of these assays and all such assays described herein, the amount of Aβ peptide in the biological sample is increased by at least two standard deviations above the reference value or first biological sample.

Provided herein, in some aspects, are assays for identifying the presence of plaques comprising Aβ peptide in the brain comprising:
a. measuring or quantifying the amount of Aβ peptide in a first biological sample obtained from a subject prior to administration of an amylin or amylin analog challenge to the subject;
b. measuring or quantifying the amount of Aβ peptide in a second biological sample obtained from the subject within 72 hours of administration of an amylin or amylin analog challenge; and
c. identifying the subject as having plaques comprising Aβ peptide in the brain and optionally selecting a therapy if the amount of Aβ peptide in the second biological sample is increased relative to the first biological sample.

In some embodiments of these assays and all such assays described herein, the amount of Aβ peptide in the biological sample is increased by at least one standard deviation above the first biological sample.

In some embodiments of these assays and all such assays described herein, the amount of Aβ peptide in the biological sample is increased by at least two standard deviations above the first biological sample.

In some embodiments of these assays and all such assays described herein, the biological sample is a blood sample, a serum sample, or a plasma sample.

In some embodiments of these assays and all such assays described herein, the amylin or amylin analog administered to the subject comprises a sequence of SEQ ID NO: 3, SEQ ID NO: 4, or SEQ ID NOs: 13-44.

In some embodiments of these assays and all such assays described herein, the Aβ peptide being measured or quantified is Aβ42 of SEQ ID NO: 2.

In some embodiments of these assays and all such assays described herein, the measuring or quantifying of steps (a) or (b) is within 24 hours of the amylin or amylin analog challenge.

In some embodiments of these assays and all such assays described herein, the measuring or quantifying of steps (a) or (b) is within 4 hours of the amylin or amylin analog challenge.

Provided herein, in some aspects, are assays comprising:
a. administering an amylin or amylin analog challenge to a subject;
b. obtaining a biological sample from the subject after the administration of the amylin or amylin analog challenge;
c. measuring or quantifying the amount of Aβ peptide in the biological sample obtained from the subject administered the amylin or amylin analog challenge; and
d. identifying the subject as having increased Aβ peptide in the brain if the amount of Aβ peptide is increased relative to the reference value.

Provided herein, in some aspects, are assays comprising:
a. measuring or quantifying the amount of Aβ peptide in a first biological sample obtained from a subject prior to administration of an amylin or amylin analog challenge to the subject;
b. administering an amylin or amylin analog challenge to the subject;
c. measuring or quantifying the amount of Aβ peptide in a second biological sample obtained from the subject within 72 hours of the administration of the amylin or amylin analog challenge; and
d. identifying the subject as having increased Aβ peptide in the brain if the amount of Aβ peptide in the second biological sample is increased relative to the first biological sample.

Provided herein, in some aspects, are assays for identifying a subject having or at risk for Alzheimer's disease or amnestic mild cognitive impairment comprising:
a. administering an amylin or amylin analog challenge to a subject;
b. obtaining a biological sample from the subject within 72 hours of the administration of the amylin or amylin analog challenge;
c. measuring or quantifying the amount of Aβ peptide in the biological sample obtained from the subject administered the amylin or amylin analog challenge; and
d. identifying the subject as having Alzheimer's disease or amnestic mild cognitive impairment if the measured or quantified amount of Aβ peptide is increased relative to a reference value.

Provided herein, in some aspects, are assays for identifying a subject having or at risk for Alzheimer's disease or amnestic mild cognitive impairment comprising:
a. measuring or quantifying the amount of Aβ peptide in a first biological sample obtained from a subject prior to administration of an amylin or amylin analog challenge to the subject;
b. administering an amylin or amylin analog challenge to the subject;
c. measuring or quantifying the amount of Aβ peptide in a second biological sample obtained from the subject within 72 hours of the administration of the amylin or amylin analog challenge to the subject; and
d. identifying the subject as having Alzheimer's disease or amnestic mild cognitive impairment if the amount of Aβ peptide measured or quantified in the second biological sample is increased relative to the first biological sample.

Provided herein, in some aspects, are assays for detecting the presence of plaques comprising Aβ peptide in the brain in a subject comprising:
a. administering an amylin or amylin analog challenge to a subject;
b. obtaining a biological sample from the subject within 72 hours of the administration of the amylin or amylin analog challenge;
c. measuring or quantifying the amount of Aβ peptide in the biological sample obtained from the subject administered the amylin or amylin analog challenge; and
d. identifying the subject as having plaques comprising Aβ peptide in the brain if the amount of Aβ peptide is increased relative to a reference value.

Provided herein, in some aspects, are assays for detecting the presence of plaques in the brain comprising Aβ peptide in a subject comprising
a. measuring or quantifying the amount of Aβ peptide in a first biological sample, obtained from a subject prior to administration of an amylin or amylin analog challenge to the subject;
b. administering an amylin or amylin analog challenge to the subject;
c. measuring or quantifying the amount of Aβ peptide in a second biological sample obtained from the subject within 72 hours of the administration of the amylin or amylin analog challenge; and
d. identifying the subject as having plaques in the brain comprising Aβ peptide, if the amount of Aβ peptide in the second biological sample is increased relative to the first biological sample.

In some embodiments of these assays and all such assays described herein, the amount of Aβ peptide in the biological sample is increased by at least one standard deviation above the reference value or first biological sample.

In some embodiments of these assays and all such assays described herein, the amount of Aβ peptide in the biological sample is increased by at least two standard deviations above the reference value or first biological sample.

In some embodiments of these assays and all such assays described herein, the biological sample is a blood sample, a serum sample, or a plasma sample.

In some embodiments of these assays and all such assays described herein, the amylin or amylin analog administered to the subject comprises a sequence of SEQ ID NO: 3, SEQ ID NO: 4, or SEQ ID NOs: 13-44.

In some embodiments of these assays and all such assays described herein, the Aβ peptide being measured or quantified is Aβ42 of SEQ ID NO: 2.

In some embodiments of these assays and all such assays described herein, the amylin or amylin analog challenge is administered to the subject via intravenous or subcutaneous administration.

In some embodiments of these assays and all such assays described herein, the measuring or quantifying of steps (b) or (c) is within 24 hours of the amylin or amylin analog challenge.

In some embodiments of these assays and all such assays described herein, the measuring or quantifying of steps (b) or (c) is within 4 hours of the amylin or amylin analog challenge.

Also provided herein, in some aspects, are methods for detecting Alzheimer's disease or amnestic mild cognitive impairment in a subject comprising:
  a. measuring or quantifying the amount of Aβ peptide in a biological sample obtained from a subject administered an amylin or amylin analog challenge within 72 hours prior to collection of the biological sample; and
  b. identifying the subject as having Alzheimer's disease or amnestic mild cognitive impairment if the amount of Aβ peptide is increased relative to a reference value.

Provided herein, in some aspects, are methods for detecting Alzheimer's disease or amnestic mild cognitive impairment in a subject comprising:
  a. measuring or quantifying the amount of Aβ peptide in a first biological sample obtained from a subject prior to administration of an amylin or amylin analog challenge to the subject;
  b. measuring or quantifying the amount of Aβ peptide in a second biological sample obtained from the subject within 72 hours of administration of the amylin or amylin analog challenge; and
  c. identifying the subject as having Alzheimer's disease or amnestic mild cognitive impairment if the amount of Aβ peptide in the second biological sample is increased relative to the first biological sample.

Provided herein, in some aspects, are methods for detecting the presence of plaques comprising Aβ peptide in the brain in a subject comprising using any of the assays described herein; and identifying the subject as having plaques comprising Aβ peptide in the brain, if the amount of Aβ peptide measured or quantified by the assay is increased relative to a reference value.

Provided herein, in some aspects, are methods for detecting Alzheimer's disease or amnestic mild cognitive impairment in a subject comprising:
  a. administering an amylin or amylin analog challenge to a subject;
  b. using any of the assays described herein; and
  c. identifying the subject as having Alzheimer's disease or amnestic mild cognitive impairment if the amount of Aβ peptide measured or quantified by the assay is increased relative to a reference value.

Provided herein, in some aspects, are methods for detecting the presence of plaques comprising Aβ peptide in a subject comprising:
  a. administering an amylin or amylin analog challenge to a subject;
  b. using any of the assays described herein; and
  c. identifying the subject as having plaques comprising Aβ peptide, if the amount of Aβ peptide measured or quantified by the assay is increased relative to a reference value.

In some embodiments of these methods and all such methods described herein, the biological sample is a blood sample, a serum sample, or a plasma sample.

In some embodiments of these methods and all such methods described herein, the amount of Aβ peptide in the biological sample is increased by at least one standard deviation above the reference value or first biological sample.

In some embodiments of these methods and all such methods described herein, the amount of Aβ peptide in the biological sample is increased by at least two standard deviations above the reference value or first biological sample.

In some embodiments of these methods and all such methods described herein, the amylin or amylin analog administered to the subject comprises a sequence of SEQ ID NO: 3, SEQ ID NO: 4, or SEQ ID NOs: 13-44.

In some embodiments of these methods and all such methods described herein, the Aβ peptide being measured or quantified is Aβ42 of SEQ ID NO: 2.

In some embodiments of these methods and all such methods described herein, the amylin or amylin analog challenge is administered to the subject via intravenous or subcutaneous administration.

In some embodiments of these methods and all such methods described herein, if the measured or quantified amount of Aβ peptide is increased relative to a reference value or relative to the first biological sample, the method further comprises administration of a therapeutically effective amount of amylin or an amylin analog. In some embodiments of these methods, the amylin or amylin analog administered to the subject comprises a sequence of SEQ ID NO: 3, SEQ ID NO: 4, or SEQ ID NOs: 13-44. In some embodiments of these methods and all such methods described herein, the amylin analog comprises pramlintide acetate of SEQ ID NO: 4.

In some embodiments of these methods and all such methods described herein, if the measured or quantified amount of Aβ peptide is increased relative to a reference value or relative to the first biological sample, the method further comprises administration of a therapeutically effective amount of a cholinesterase inhibitor. In some embodiments of these methods, the cholinesterase inhibitor is galantamine, rivastigmine, or donepezil.

In some embodiments of these methods and all such methods described herein, if the measured or quantified amount of Aβ peptide is increased relative to a reference value or relative to the first biological sample, the method further comprises administration of a therapeutically effective amount of an N-methyl D-aspartate (NMDA) antagonist. In some embodiments of these methods, the N-methyl D-aspartate (NMDA) antagonist is memantine.

In some embodiments of these methods and all such methods described herein, if the measured or quantified amount of Aβ peptide is increased relative to a reference value or relative to the first biological sample, the method further comprises increasing audio stimuli, visual stimuli, or a combination thereof to the subject.

In some embodiments of these methods and all such methods described herein, the step of determining, quantifying, or measuring the amount of Aβ peptide in the biological sample is performed using a non-human machine.

Also provided herein, in some aspects, are systems for obtaining data from at least one biological sample obtained from a subject within 72 hours of amylin administration, the system comprising:
a. a determination module configured to receive said at least one biological sample obtained from a subject within 72 hours of administration of amylin or an amylin analog, and perform a measurement or quantification of the amount of Aβ peptide in the at least one biological sample to generate an Aβ peptide amount output;
b. a storage device configured to store said Aβ peptide amount output from said determination module;
c. a comparison module configured to receive said Aβ peptide amount output of the biological sample sample obtained from the subject within 72 hours of administration of amylin or an amylin analog, and perform at least one comparison analysis on said Aβ peptide amount output to determine the presence or absence of one of the following conditions and produce a comparison data output:
  i. the biological sample from obtained from a subject within 72 hours of administration of amylin or an amylin analog has an increased amount of Aβ peptide relative to a reference value; or
  ii. the biological sample from obtained from a subject within 72 hours of administration of amylin or an amylin analog does not have increased amount of Aβ peptide relative to a reference value; and
d. an output or display module for displaying a content based in part on the comparison data output from said comparison module, wherein the content comprises a signal indicative that the biological sample obtained from a subject within 72 hours of administration of amylin or an amylin analog has increased amount of Aβ peptide relative to the reference value, or a signal indicative that the biological sample obtained from the subject within 72 hours of administration of amylin or an amylin analog does not have increased amount of Aβ peptide relative to the reference value.

In some embodiments of these systems and all such systems described herein, the at least one biological sample is a blood sample, a serum sample, or a plasma sample.

In some embodiments of these systems and all such systems described herein, the amount of Aβ peptide being measured or quantified by the determination module of step (a) is Aβ42 of SEQ ID NO: 2.

In some embodiments of these systems and all such systems described herein, the at least one biological sample is obtained from the subject within 24 hours of administration of amylin or an amylin analog.

In some embodiments of these systems and all such systems described herein, the at least one biological sample is obtained from the subject within 4 hours of administration of amylin or an amylin analog.

In some embodiments of these systems and all such systems described herein, the amylin or amylin analog administered to the subject comprises a sequence of SEQ ID NO: 3, SEQ ID NO: 4, or SEQ ID NOs: 13-44.

In some embodiments of these systems and all such systems described herein, the comparison output of step (c) determines whether the amount of Aβ peptide in the biological sample is increased by at least one standard deviation above the reference value.

In some embodiments of these systems and all such systems described herein, the comparison output of step (c) determines whether the amount of Aβ peptide in the biological sample is increased by at least two standard deviations above the reference value.

Also provided herein, in some aspects, is an amylin or an amylin analog for use in reducing Aβ peptide deposition in the brain of a subject.

Provided herein, in some aspects, is an amylin or an amylin analog for use in inhibiting progression of Alzheimer's disease or amnestic mild cognitive impairment in a subject.

In some embodiments of these uses and all such uses described herein, the amylin or an amylin analog is formulated for administration to a subject at least once a week.

In some embodiments of these uses and all such uses described herein, the amylin or an amylin analog is formulated for administration to a subject at least twice a week.

In some embodiments of these uses and all such uses described herein, the amylin or an amylin analog is formulated for administration to a subject at least three times a week.

In some embodiments of these uses and all such uses described herein, the amylin or an amylin analog is formulated for administration to a subject at least four times a week.

In some embodiments of these uses and all such uses described herein, the amylin or an amylin analog is formulated for administration to a subject daily.

In some embodiments of these uses and all such uses described herein, the amylin or an amylin analog is formulated for administration to a subject by injection. In some embodiments of these uses, the injection is a systemic injection.

In some embodiments of these uses and all such uses described herein, the amylin or amylin analog comprises a sequence of SEQ ID NO: 3, SEQ ID NO: 4, or SEQ ID NOs: 13-44.

In some embodiments of these uses and all such uses described herein, the amylin or amylin analog is formulated as a unit dose composition.

In some embodiments of these uses and all such uses described herein, the subject having Aβ peptide deposition in the brain has or is at risk for Alzheimer's disease or amnestic mild cognitive impairment (aMCI).

In some aspects, provided herein are assays comprising: measuring or quantifying the amount of Aβ peptide in a biological sample obtained from a subject administered an amylin or amylin analog challenge within 72 hours prior to collection of the biological sample; and comparing the measured or quantified amount of Aβ peptide with a reference value, and if the amount of Aβ peptide is increased relative to the reference value, identifying the subject as having increased Aβ peptide.

Also provided herein, in some aspects, are assays comprising: measuring or quantifying the amount of Aβ peptide in a first biological sample obtained from a subject prior to administration of an amylin or amylin analog challenge to the subject; measuring or quantifying the amount of Aβ peptide in a second biological sample obtained from the subject within 72 hours of administration of an amylin or amylin analog challenge; and comparing the measured or quantified amount of Aβ peptide in the second biological sample to the first biological sample, and if the amount of Aβ peptide in the second biological sample is increased relative to the first biological sample, identifying the subject as having increased Aβ peptide.

In other aspects, provided herein are assays for Alzheimer's disease or amnestic mild cognitive impairment comprising: measuring or quantifying the amount of Aβ peptide in a biological sample obtained from a subject administered an amylin or amylin analog challenge within 72 hours prior to collection of the biological sample; and comparing the measured or quantified amount of Aβ peptide with a reference value, and if the amount of Aβ peptide is increased relative to the reference value, identifying the subject as having Alzheimer's disease or amnestic mild cognitive impairment.

Also provided herein, in some aspects, are assays for Alzheimer's disease or amnestic mild cognitive impairment comprising: measuring or quantifying the amount of Aβ peptide in a first biological sample obtained from a subject prior to administration of an amylin or amylin analog challenge to the subject; measuring or quantifying the amount of Aβ peptide in a second biological sample obtained from the subject within 72 hours of administration of an amylin or amylin analog challenge; and comparing the measured or quantified amount of Aβ peptide in the second biological sample to the first biological sample, and if the amount of Aβ peptide in the second biological sample is increased relative to the first biological sample, identifying the subject as having Alzheimer's disease or amnestic mild cognitive impairment.

In some aspects, provided herein are assays for detecting the presence of plaques comprising Aβ peptide comprising: measuring or quantifying the amount of Aβ peptide in a biological sample obtained from a subject administered an amylin or amylin analog challenge within 72 hours prior to collection of the biological sample; and comparing the measured or quantified amount of Aβ peptide with a reference value, and if the amount of Aβ peptide is increased relative to the reference value, identifying the subject as having plaques comprising Aβ peptide.

In some embodiments of these assays and all such assays described herein, the reference value is the value of Aβ peptide in a biological sample from said subject prior to administration of the amylin or amylin analog challenge.

Also provided herein, in some aspects, are assays for detecting the presence of plaques comprising Aβ peptide comprising: measuring or quantifying the amount of Aβ peptide in a first biological sample obtained from a subject prior to administration of an amylin or amylin analog challenge to the subject; measuring or quantifying the amount of Aβ peptide in a second biological sample obtained from the subject within 72 hours of administration of an amylin or amylin analog challenge; and comparing the measured or quantified amount of Aβ peptide in the second biological sample to the first biological sample, and if the amount of Aβ peptide in the second biological sample is increased relative to the first biological sample, identifying the subject as having plaques comprising Aβ peptide.

In some embodiments of these assays and all such assays described herein, the biological sample is a blood sample, a serum sample, or a plasma sample.

In some embodiments of these assays and all such assays described herein, the amylin or amylin analog administered to the subject comprises a sequence of SEQ ID NO: 3, SEQ ID NO: 4, or SEQ ID NOs: 13-144.

In some embodiments of these assays and all such assays described herein, the Aβ peptide being measured or quantified is Aβ42 of SEQ ID NO: 2.

In some aspects, provided herein are assays comprising: administering an amylin or amylin analog challenge to a subject; obtaining a biological sample from the subject after the administration of the amylin or amylin analog challenge; measuring or quantifying the amount of Aβ peptide in the biological sample obtained from the subject administered the amylin or amylin analog challenge; and comparing the measured or quantified amount of Aβ peptide with a reference value, and if the amount of Aβ peptide is increased relative to the reference value, identifying the subject as having increased Aβ peptide.

In some aspects, provided herein are assays comprising: measuring or quantifying the amount of Aβ peptide in a first biological sample obtained from a subject prior to administration of an amylin or amylin analog challenge to the subject; administering an amylin or amylin analog challenge to the subject; measuring or quantifying the amount of Aβ peptide in a second biological sample obtained from the subject within 72 hours of the administration of the amylin or amylin analog challenge; and comparing the measured or quantified amount of Aβ peptide in the second biological sample to the first biological sample, and if the amount of Aβ peptide in the second biological sample is increased relative to the first biological sample, identifying the subject as having increased Aβ peptide.

In some aspects, provided herein are assays for Alzheimer's disease or amnestic mild cognitive impairment comprising: administering an amylin or amylin analog challenge to a subject; obtaining a biological sample from the subject within 72 hours of the administration of the amylin or amylin analog challenge; measuring or quantifying the amount of Aβ peptide in the biological sample obtained from the subject administered the amylin or amylin analog challenge; and comparing the measured or quantified amount of Aβ peptide with a reference value, and if the amount of Aβ peptide is increased relative to the reference value, identifying the subject as having Alzheimer's disease or amnestic mild cognitive impairment.

In some aspects, provided herein are assays for Alzheimer's disease or amnestic mild cognitive impairment comprising: measuring or quantifying the amount of Aβ peptide in a first biological sample obtained from a subject prior to administration of an amylin or amylin analog challenge to the subject; administering an amylin or amylin analog challenge to the subject; measuring or quantifying the amount of Aβ peptide in a second biological sample obtained from the subject within 72 hours of the administration of the amylin or amylin analog challenge to the subject; and comparing the measured or quantified amount of Aβ peptide in the second biological sample to the first biological sample, and if the amount of Aβ peptide in the second biological sample is increased relative to the first biological sample, identifying the subject as having Alzheimer's disease or amnestic mild cognitive impairment.

In some aspects, provided herein are assays for detecting the presence of plaques comprising Aβ peptide in a subject comprising: administering an amylin or amylin analog challenge to a subject; obtaining a biological sample from the subject within 72 hours of the administration of the amylin or amylin analog challenge; measuring or quantifying the amount of Aβ peptide in the biological sample obtained from the subject administered the amylin or amylin analog challenge; and comparing the measured or quantified amount of Aβ peptide with a reference value, and if the amount of Aβ peptide is increased relative to the reference value, identifying the subject as having plaques comprising Aβ peptide.

In some aspects, provided herein are assays for detecting the presence of plaques comprising Aβ peptide in a subject comprising: measuring or quantifying the amount of Aβ peptide in a first biological sample obtained from a subject prior to administration of an amylin or amylin analog challenge to the subject; administering an amylin or amylin analog challenge to the subject; measuring or quantifying the amount of Aβ peptide in a second biological sample obtained from the subject within 72 hours of the administration of the amylin or amylin analog challenge; and comparing the measured or quantified amount of Aβ peptide in the second biological sample to the first biological sample, and if the amount of Aβ peptide in the second biological sample is increased relative to the first biological sample, identifying the subject as having plaques comprising Aβ peptide.

In some embodiments of these assays and all such assays described herein, the biological sample is a blood sample, a serum sample, or a plasma sample.

In some embodiments of these assays and all such assays described herein, the amylin or amylin analog administered to the subject comprises a sequence of SEQ ID NOs: 3 or 4.

In some embodiments of these assays and all such assays described herein, the Aβ peptide being measured or quantified is Aβ42 of SEQ ID NO: 2.

In some embodiments of these assays and all such assays described herein, the amylin or amylin analog challenge is administered to the subject via intravenous or subcutaneous administration.

Also provided herein, in some aspects, are methods for detecting Alzheimer's disease or amnestic mild cognitive impairment in a subject comprising: measuring or quantifying the amount of Aβ peptide in a biological sample obtained from a subject administered an amylin or amylin analog challenge within 72 hours prior to collection of the biological sample; and comparing the measured or quantified amount of Aβ peptide with a reference value, and if the amount of Aβ peptide is increased relative to the reference value, identifying the subject as having Alzheimer's disease or amnestic mild cognitive impairment.

In some aspects, provided herein are methods for detecting Alzheimer's disease or amnestic mild cognitive impairment in a subject comprising: measuring or quantifying the amount of Aβ peptide in a first biological sample obtained from a subject prior to administration of an amylin or amylin analog challenge to the subject; measuring or quantifying the amount of Aβ peptide in a second biological sample obtained from the subject within 72 hours of administration of the amylin or amylin analog challenge; and comparing the measured or quantified amount of Aβ peptide in the second biological sample to the first biological sample, and if the amount of Aβ peptide in the second biological sample is increased relative to the first biological sample, identifying the subject as having Alzheimer's disease or amnestic mild cognitive impairment.

In some aspects, provided herein are methods for detecting the presence of plaques comprising Aβ peptide in a subject comprising: measuring or quantifying the amount of Aβ peptide in a biological sample obtained from a subject administered an amylin or amylin analog challenge within 72 hours prior to collection of the biological sample; and comparing the measured or quantified amount of Aβ peptide with a reference value, and if the amount of Aβ peptide is increased relative to the reference value, identifying the subject as having plaques comprising Aβ peptide.

In some aspects, provided herein are methods for detecting the presence of plaques comprising Aβ peptide in a subject: measuring or quantifying the amount of Aβ peptide in a first biological sample obtained from a subject prior to administration of an amylin or amylin analog challenge to the subject; measuring or quantifying the amount of Aβ peptide in a second biological sample obtained from the subject within 72 hours of administration of the amylin or amylin analog challenge; and comparing the measured or quantified amount of Aβ peptide in the second biological sample to the first biological sample, and if the amount of Aβ peptide in the second biological sample is increased relative to the first biological sample, identifying the subject as having plaques comprising Aβ peptide.

In some aspects, provided herein are methods for detecting Alzheimer's disease or amnestic mild cognitive impairment in a subject comprising: administering an amylin or amylin analog challenge to a subject; obtaining a biological sample from the subject within 72 hours of the administration of the amylin or amylin analog challenge; measuring or quantifying the amount of Aβ peptide in the biological sample obtained from the subject administered amylin; and comparing the measured or quantified amount of Aβ peptide with a reference value, and if the amount of Aβ peptide is increased relative to the reference value, identifying the subject as having Alzheimer's disease or amnestic mild cognitive impairment.

In some aspects, provided herein are methods for detecting Alzheimer's disease or amnestic mild cognitive impairment comprising:measuring or quantifying the amount of Aβ peptide in a first biological sample obtained from a subject prior to administration of an amylin or amylin analog challenge to the subject; administering an amylin or amylin analog challenge to the subject; measuring or quantifying the amount of Aβ peptide in a second biological sample obtained from the subject within 72 hours of the administration of the amylin or amylin analog challenge; and comparing the measured or quantified amount of Aβ peptide in the second biological sample to the first biological sample, and if the amount of Aβ peptide in the second biological sample is increased relative to the first biological sample, identifying the subject as having Alzheimer's disease or amnestic mild cognitive impairment.

In some aspects, provided herein are methods for detecting the presence of plaques comprising Aβ peptide in a subject comprising: administering an amylin or amylin analog challenge to a subject; obtaining a biological sample from the subject within 72 hours of the administration of the amylin or amylin analog challenge; measuring or quantifying the amount of Aβ peptide in the biological sample obtained from the subject administered amylin; and comparing the measured or quantified amount of Aβ peptide with a reference value, and if the amount of Aβ peptide is increased relative to the reference value, identifying the subject as having plaques comprising Aβ peptide.

In some aspects, provided herein are methods for detecting the presence of plaques comprising Aβ peptide in a subject comprising: measuring or quantifying the amount of Aβ peptide in a first biological sample obtained from a subject prior to administration of an amylin or amylin analog challenge to the subject; administering an amylin or amylin analog challenge to the subject; measuring or quantifying the amount of Aβ peptide in a second biological sample obtained from the subject within 72 hours of the administration of the amylin or amylin analog challenge; and comparing the measured or quantified amount of Aβ peptide in the second biological sample to the first biological sample, and if the amount of Aβ peptide in the second biological sample is increased relative to the first biological sample, identifying the subject as having plaques comprising Aβ peptide.

In some embodiments of these methods and all such methods described herein, the biological sample is a blood sample, a serum sample, or a plasma sample.

In some embodiments of these methods and all such methods described herein, the amylin or amylin analog administered to the subject comprises a sequence of SEQ ID NOs: 3 or 4.

In some embodiments of these methods and all such methods described herein, the Aβ peptide being measured or quantified is Aβ42 of SEQ ID NO: 2.

In some embodiments of these methods and all such methods described herein, the amylin or amylin analog challenge is administered to the subject via intravenous or subcutaneous administration.

In some embodiments of these methods and all such methods described herein, if the measured or quantified amount of Aβ peptide is increased relative to the reference value or relative to the first biological sample, the method further comprises administration of a cholinesterase inhibitor. In some such embodiments, the cholinesterase inhibitor is galantamine, rivastigmine, or donepezil.

In some embodiments of these methods and all such methods described herein, if the measured or quantified amount of Aβ peptide is increased relative to the reference value or relative to the first biological sample, the method further comprises administration of an N-methyl D-aspartate (NMDA) antagonist. In some such embodiments, the N-methyl D-aspartate (NMDA) antagonist is memantine.

In some embodiments of these methods and all such methods described herein, if the measured or quantified amount of Aβ peptide is increased relative to the reference value or relative to the first biological sample, the method further comprises administration of amylin or an amylin analog. In some such embodiments, the amylin analog comprises pramlintide acetate of SEQ ID NO: 4.

In some embodiments of these methods and all such methods described herein, if the measured or quantified amount of Aβ peptide is increased relative to the reference value or relative to the first biological sample, the method further comprises increasing audio stimuli, visual stimuli, or a combination thereof to the subject.

In some embodiments of these assays and methods and all such assays and methods described herein, the step of comparing the measured or quantified amount of Aβ peptide in the biological sample is performed using a non-human machine.

Also provided herein, in some aspects, are systems for obtaining data from at least one biological sample obtained from a subject within 72 hours of amylin administration, the system comprising:

a determination module configured to receive said at least one biological sample obtained from a subject within 72 hours of administration of amylin or an amylin analog, and perform a measurement or quantification of the amount of Aβ peptide in the at least one biological sample to generate an Aβ peptide amount output;

a storage device configured to store said Aβ peptide amount output from said determination module;

a comparison module configured to receive said Aβ peptide amount output of the biological sample sample obtained from the subject within 72 hours of administration of amylin or an amylin analog, and perform at least one comparison analysis on said Aβ peptide amount output to determine the presence or absence of one of the following conditions and produce a comparison data output:

the biological sample from obtained from a subject within 72 hours of administration of amylin or an amylin analog has an increased amount of Aβ peptide relative to a reference value; or the biological sample from obtained from a subject within 72 hours of administration of amylin or an amylin analog does not have increased amount of Aβ peptide relative to a reference value; and an output or display module for displaying a content based in part on the comparison data output from said comparison module, wherein the content comprises a signal indicative that the biological sample from obtained from a subject within 72 hours of administration of amylin or an amylin analog has increased amount of Aβ peptide relative to the reference value, or a signal indicative that the biological sample from obtained from a subject within 72 hours of administration of amylin or an amylin analog does not have increased does not have increased amount of Aβ peptide relative to the reference value.

In some embodiments of these systems and all such systems described herein, the at least one biological sample is a blood sample, a serum sample, or a plasma sample.

In some embodiments of these systems and all such systems described herein, the amount of Aβ peptide being measured or quantified by the determination module of step (a) is Aβ42 of SEQ ID NO: 2.

Definitions

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

"Amyloidosis," as used herein, refers to a condition found in a variety of diseases that is characterized by an accumulation of amyloid material in the organs or tissues of the body.

As used herein, the terms "Aβ peptide" or "Aβ" refer to the peptides generated by the successive action of the β and γ secretases, such as Aβ40 and Aβ42. The most common isoforms are Aβ40 and Aβ42.

Amnestic mild cognitive impairment" ("aMCI") refers to a prodromal phase of Alzheimer's that has a fairly high rate of conversion to Alzheimer's disease.

By "amylin" or "Insulin Amyloid Polypeptide (IAP or IAPP)," is meant the human peptide hormone of 37 amino acids referred to as amylin, which is co-secreted with insulin from β-cells of the pancreas, and polymorphic and species variations thereof. The term "amylin" also includes variants of amylin as present in, and in isolatable form, other mammalian species.

As used herein, an "amylin analog" or "amylin agonist compound" is a molecule that has properties that are as good as or better than the parent amylin compound. The amylin analog has the same physiological effects as amylin, including, for example, glucose regulation and having the ability to traverse the blood brain area, but having, for example, one or more amino acid variations that, for example, enhance its effectiveness as a drug or increases solubility, or otherwise increases its therapeutic properties, such as superior stability, solubility, efficacy, half-life, and the like.

The term "unit dose," as used herein, refers to physically discrete units suitable as unitary dosage for the subject, each unit containing a predetermined quantity of active material, such as an amylin analog of any of SEQ ID NO: 3, SEQ ID NO: 4 or SEQ ID NOs: 13-44, calculated to produce the desired therapeutic effect in association with the required physiologically acceptable diluent, i.e., carrier, or vehicle.

The terms "treatment" and "treating" as used herein, with respect to treatment of a disease, means preventing the progression of the disease, or altering the course of the disorder (for example, but are not limited to, slowing the progression of the disorder), or reversing a symptom of the disorder or reducing one or more symptoms and/or one or more biochemical markers in a subject, preventing one or more symptoms from worsening or progressing, promoting recovery or improving prognosis.

As used herein, "effective treatment" includes any statistically significant improvement in one or more indicia of the disease or disorder.

As used herein, "an amylin or amylin analog challenge" refers to administration of a dose of amylin or an amylin analog to a subject in an amount sufficient to measure or quantify a subject's response to the amylin via measurement or quantification of Aβ peptide in a biological sample obtained from the subject.

As used herein, "determining the amount of Aβ peptide," or "measuring or quantifying the amount of Aβ peptide," refers to any method or assay that can be used to obtain a qualitative or quantitative measurement of the expression of Aβ peptide in a biological sample obtained from a subject.

The terms "increased," "increase" or "enhance" in connection with the amount of Aβ peptide in a biological sample obtained from a subject following administration of amylin are all used herein to generally mean an increase by a statically significant amount. For the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference value or level, or at least about a 1.5-fold, at least about a 1.6-fold, at least about a 1.7-fold, at least about a 1.8-fold, at least about a 1.9-fold, at least about a 2-fold, at least about a 3-fold, or at least about a 4-fold, or at least about a 5-fold, at least about a 10-fold increase, any increase between 2-fold and 10-fold, at least about a 25-fold increase, or greater as compared to a reference level. In some embodiments, an increase is at least one standard deviation greater than, or at least two standard deviations, or more, greater than a median or mean reference level. Such median or mean reference levels can be obtained, for example, from five or more samples obtained from subjects not having Alzheimer's disease or aMCI, or from five or more samples obtained from the same subject at different timepoints.

The reference level is obtained or measured in a reference biological sample, such as a reference sample obtained from an age-matched normal control (e.g., an age-matched subject not having Alzheimer's disease), or a reference sample from the same subject prior to administration of amylin or an amylin analog, for example, a "first biological sample." A "reference value" is thus, in some embodiments, a predetermined reference level, such as an average or median amount or level of Aβ peptide obtained from, for example, biological samples from a population of healthy subjects that are in the chronological age group matched with the chronological age of the tested subject.

As used herein, the terms "biological sample" or "subject sample" or "sample" refer to a quantity of tissue or fluid, or a cell or population of cells obtained from a subject. In some embodiments, the biological sample is a blood sample, including, for example, a serum sample, or a plasma sample. Most often, the sample has been removed from a subject, but the term "biological sample" can also, in some embodiments, refer to cells or tissue or a quantity of tissue or fluid analyzed in vivo, i.e. without removal from the subject. A biological sample or tissue sample includes, but is not limited to, blood, plasma, serum, cerebrospinal fluid, lymph fluid, bone marrow, tumor biopsy, urine, stool, sputum, pleural fluid, nipple aspirates, lymph fluid, the external sections of the skin, lung tissue, adipose tissue, connective tissue, sub-epithelial tissue, epithelial tissue, liver tissue, kidney tissue, uterine tissue, respiratory tissues, breast tissue, gastrointestinal tissue, and genitourinary tract tissue, tears, saliva, milk, cells (including, but not limited to, blood cells), biopsies, scrapes (e.g., buccal scrapes), tumors, organs, and also samples of an in vitro cell culture constituent. Often, a "biological sample" can comprise cells from the subject, but the term can also refer to non-cellular biological material, such as non-cellular fractions of blood, saliva, or urine.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with percentages can mean±1%.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9);

and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006. Definitions of common terms in molecular biology are found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol.152, S. L. Berger and A. R. Kimmerl Eds., Academic Press Inc., San Diego, USA (1987); Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.) and Current Protocols in Immunology (CPI) (John E. Coligan, et. al., ed. John Wiley and Sons, Inc.), which are all incorporated by reference herein in their entireties.

It is understood that the following detailed description and examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

BRIEF DESCRIPTION OF THE DRAWINGS

FIGS. 2A-2J demonstrate that amylin challenge blood assays can be used to detect A$\beta$ deposits in the brain. TgAPP2576 mice (n=5) and control mice (n=5) were used. Intraperitoneal injection of amylin (20 mg/kg) was performed, and blood was drawn and collected at pre-injection, after injection at 5 minutes, 1 hr and 24 hrs. Serum A$\beta$1-40 and A$\beta$1-42 were measured using ELISA assay. The results of serum A$\beta$1-40 and A$\beta$1-42 for each individual mouse are shown. This experiment has been repeated twice for each mouse and similar results were obtained.

FIGS. 3A-3E demonstrate that amylin injection removes A$\beta$ from the brain into blood in APP transgenic mice. Both the Tg2576 and wild type (WT) mice were used for the amylin challenge test. FIGS. 3A-3B. Amylin (20 mg/kg) was intraperitoneally injected (i.p), and blood was drawn and collected at the time points of pre-injection (the control n=7; Tg2576 n=11), after injection 5 minutes (the control n=7; Tg2576 n=6), 1 hr (the control n=7; Tg2576 n=10) and 24 hrs (the control n=7; Tg2576 n=11). Serum A$\beta$1-40 and A$\beta$1-42 were measured by using the ELISA assays. FIGS. 3C-3E. The levels of serum A$\beta$1-40 and A$\beta$1-42 at pre-injection of amylin were treated as 1 s, and the relative fold increase after amylin injection at each time point was shown and compared with the pre-injection level by using two-way ANOVA. *$p<0.01$; $p<0.05$ and *$p<0.10$.

FIGS. 6A-6D further show the group differences at different time points, demonstrating that the peripheral amylin injection can induce increases of both blood A$\beta$40 and A$\beta$42 specifically in Tg2576 mice.

FIG. 7 shows results of i.p injection of pramlintide, an analog of amylin, into one Tg2576 mouse (A1) and two wild type mice (N1 and N2) and comparison of their serum A$\beta$40 level before and after the injection. Again, one pramlintide injection induced the surge of serum A$\beta$40 in the Tg2576 mouse, but not in those wild type mice, indicating that pramlintide can have the same effect as amylin.

FIGS. 8A-8B demonstrate that increased blood A$\beta$ induced by the amylin injection reflecting the brain pathology: To further prove that the surge of A$\beta$ in serum provoked by the amylin challenge correlates with Aβ pathology in the brain, another type of APP transgenic mice, 5XFAD, was used, which have abundant Aβ42, but very little or no Aβ40, in the brain when the animals are young. FIG. 8A shows that the i.p injection of amylin into 5XFAD mice aged 3 months resulted in an increased level of Aβ1-42, but not Aβ1-40, in serum. Using another APP mouse line which carries the APP Dutch mutation and mainly produces Aβ40, but not Aβ42, the amylin challenge provoked only a surge of Aβ1-40, but not Aβ1-42, in blood (FIG. 8B).

FIG. 12 shows a significant increase of Aβ1-42/Aβ1-40 ratio in the AD subject, whereas a decrease of the ratio was observed in the control subject, at 3 hours post-injection, after the challenge of pramlintide. A broad range of pramlintide doses (30 to 300 mcg tid) are used clinically and shown to reduce postprandial plasma glucose concentrations safely (NDA21-332). The human results provided herein are encouraging, in part, because the dose of pramlintide (60 mcg) used was only moderate.

FIG. 16 discloses SEQ ID NOs 3 and 45, respectively, in order of appearance.

DETAILED DESCRIPTION OF THE INVENTION

Figure 1:
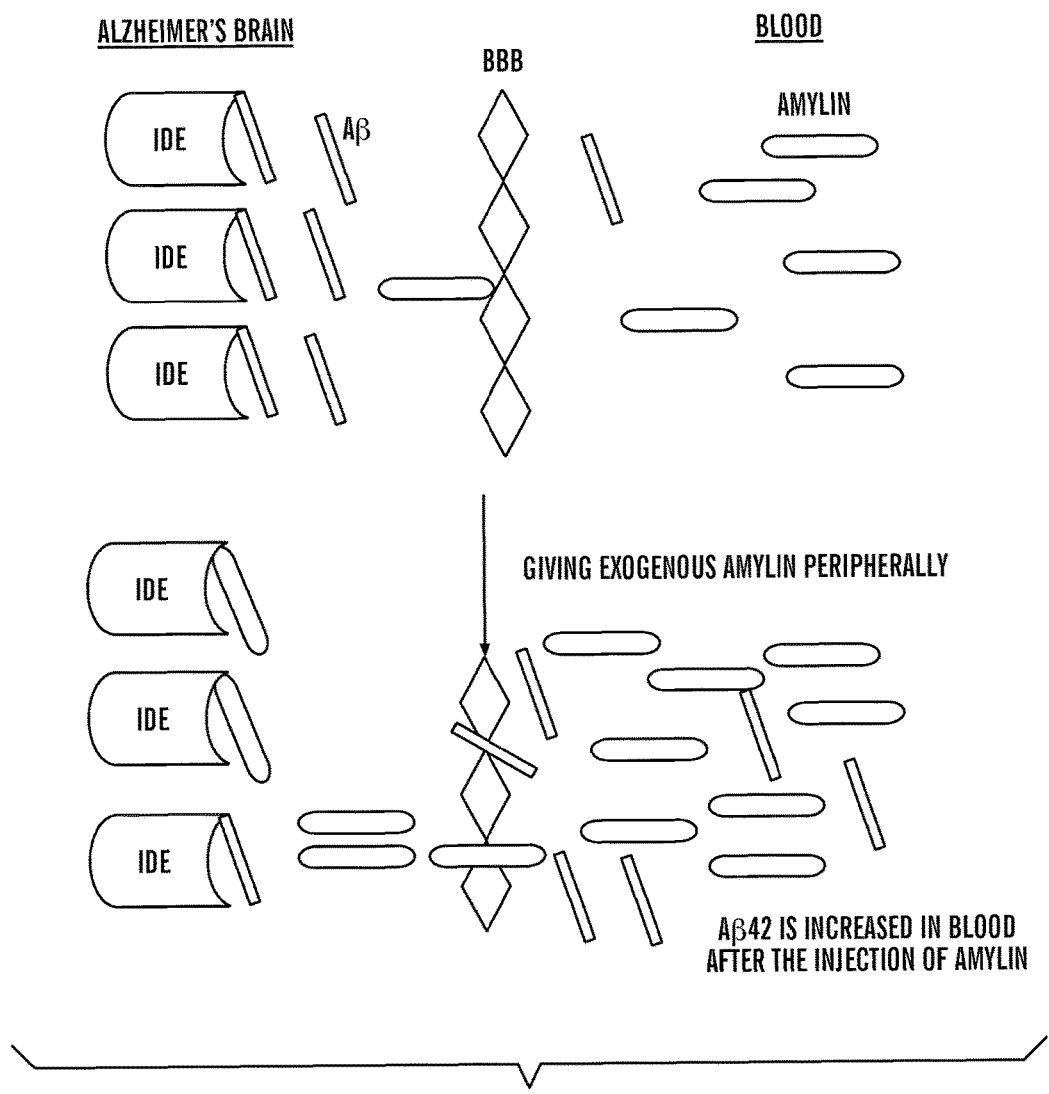
FIG. 1 demonstrates that amylin injection increases the level of A$\beta$ in blood because, without wishing to be bound or limited by theory, elevated amylin can traverse the blood brain barrier and competes with A$\beta$ for IDE (insulin degrading enzyme). This results in a relative deficiency of IDE to bind A$\beta$ and A$\beta$ and efflux into blood.
Figure 2G:
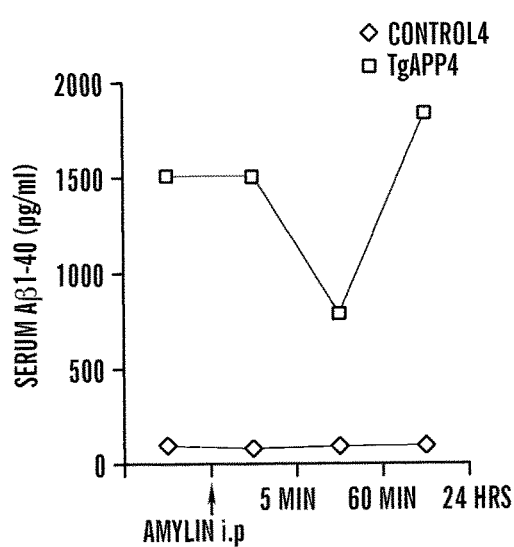
Figure 2H:
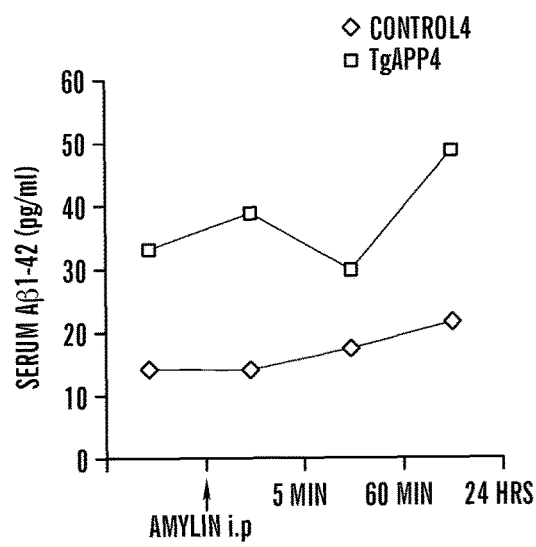
Figure 2I:
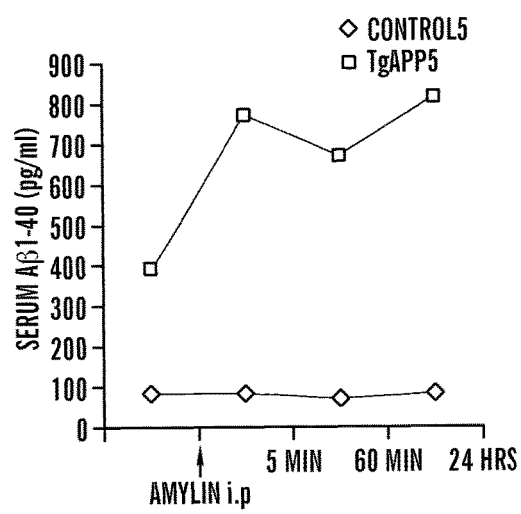
Figure 2J:
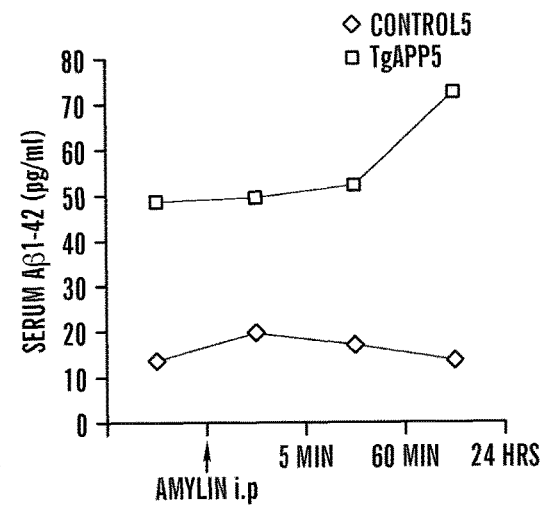

Amylin is a peptide hormone associated with metabolism and glucose regulation, and its analog, pramlintide, is used clinically and has been shown to reduce post-prandial plasma glucose concentrations. The data provided herein demonstrate the discovery that amylin or an amylin analog can serve as a treatment for Alzheimer's disease and other conditions relating to increased Aβ peptide in the brain. These data demonstrate that repeated administration of amylin or an amylin analog has long-term effects on acquisition and retention of memory, thus indicating that amylin or amylin analog administration can be used for the treatment of Alzheimer's disease and conditions relating to increased Aβ peptide in the brain.

In particular, the inventors have determined using amyloid precursor protein (APP) transgenic mice that peripheral injection of amylin can remove Aβ from the brain into blood in APP transgenic mice, and that this activity is through the amylin receptor. It was also determined that the higher the levels of Aβ in the brain, the higher the fold-increase in serum Aβ levels following amylin or amylin analog injection, and thus the surge of Aβ in serum provoked by amylin injection correlates with Aβ pathology in the brain. The inventors have also determined that amylin treatment for 8 weeks improved memory impairment in murine models of Alzheimer's, including the acquisition and learning aspects of memory. These findings have been substantiated in humans in a cross-sectional study, where plasma amylin concentration was significantly correlated with Aβ only among the elderly with AD or amnestic mild cognitive impairment (amnestic MCI), but not in those with normal cognition or other types of dementia. In addition, the surge in serum Aβ following amylin injection was also observed in human subjects, indicating that the results obtained in animal models are predictive, and that administration of amylin or an amylin analog can be used for the treatment or delay in progression of Alzheimer's disease.

Accordingly, provided herein, in some aspects, are methods of reducing and/or inhibiting Aβ deposition or Aβ plaque formation in the brain, and/or inhibiting or slowing the progression of disorders mediated by Aβ deposition or Aβ plaque formation, such as Alzheimer's disease, in a subject in need thereof by administering to subjects known or predisposed to have Aβ deposition or Aβ plaque formation in the brain therapeutically effective amounts of amylin agonist compounds or pharmaceutical compositions comprising amylin agonist compounds. The therapeutically effective amounts preferably provide at least a minimum therapeutically effective plasma level of the amylin agonist compounds in the mammals. These methods of reducing and/or inhibiting Aβ deposition or Aβ plaque formation in the brain, and/or inhibiting or slowing the progression of disorders mediated by Aβ deposition or Aβ plaque formation can further be combined with the diagnostic assays and methods described herein, where amylin or an amylin agonist compound is administered to a subject suspected or at risk for Aβ deposition in the brain, and, if a surge is detected following such administration, treatment can be commenced with administration of amylin or an amylin agonist compound at regular intervals.

Until the discoveries described herein, determination and diagnosis of amyloid associated diseases, such as Alzheimer's disease, has had little success, and has required complicated, expensive, and/or invasive tools and methods. In contrast to the standard of care methods and assays for determination and diagnosis of amyloid associated diseases, the assays and methods described herein are minimally invasive, inexpensive, and require only an amylin or amylin analog challenge as part of a simple blood test or assay. The data provided herein also demonstrate the finding that amylin or amylin analogs can be used in assays, in vitro and ex vivo methods, and kits for detecting the presence of plaques comprising Aβ peptide in the brain, and for identifying individuals at increased risk for Alzheimer's disease (AD) and/or amnestic mild cognitive impairment. As described herein, a significant positive correlation between the concentrations of amylin and Aβ1-40 or Aβ1-42 in plasma samples from human subjects with AD or amnestic MCI, but not in control subjects was found. In addition, as demonstrated herein, the inventors showed that intraperitoneal or subcutaneous injection of amylin or an amylin analog in mice and humans, respectively, results in increased blood levels of Aβ peptide in subjects with Alzheimer's disease.

More specifically, as demonstrated herein challenge administration of amylin or an amylin analog, subcutaneously or intravenously, and drawing blood before and after administering amylin to measure the level or amount of Aβ peptide, such as Aβ42 peptide, can be used in assays, methods, and kits to detect the presence of plaques comprising Aβ peptide, such as Aβ42 in the brain, and diagnose AD and amnestic MCI. As described herein, the inventors used APP transgenic mice (Tg2576) to conduct amylin challenge tests (FIGS. 2A-2J). Tg2576 mice have Aβ deposits in the brain, similar to the AD pathology observed in humans. After introperitoneal injection of amylin (20 mg/kg), the Tg2576 mice presented with an increase of serum Aβ40 and Aβ42 at 5 minutes, 1 hour and at 24 hours compared to the pre-injection levels of serum Aβ40 and Aβ42. However, control mice did not have these surges of serum Aβ40 and Aβ42 after the amylin challenge. Accordingly, using the assays, methods and kits described herein, AD patients or prodromal AD patients (amnestic MCI) with plaques comprising Aβ peptide, such as Aβ42, or having increased Aβ peptide, such as Aβ42, in the brain will generate an elevated level of Aβ peptide, e.g., Aβ42, in their blood or plasma after an amylin challenge injection compared to a baseline reference value, such as prior to injection with amylin. Patients with other types of dementia or no AD will not have a rise in Aβ peptide in their blood after the amylin injection because there is little or no Aβ peptide in their brains.

Also provided herein, in some aspects, are amylin and amylin analogs for neural imaging purposes. As described herein, the inventors have determined that amylin can traverse the blood brain barrier, and interacts with the amylin receptor (calcitonin receptor (CTR) and receptor activity modifying protein 3 (RAMP3) or CTR/RAMP3) and IDE (insulin degrading enzyme in the brain). Thus, compositions comprising amylin and amylin analogs can be used for neural imaging purposes if suitably labeled, for example, and in assays thereof.

Thus, the assays, methods, and kits described herein provide similar platforms for the diagnosis of Alzheimer's and amnestic MCI to those used in glucose tolerance tests, in which only patients having diabetes show abnormalities after a challenge with glucose is given, but not non-diabetic subjects. Further, amylin and amylin analogs are already safely used in the treatment of Type 2 diabetes, as explained elsewhere herein. Accordingly, the assays, methods, and tests described herein can be used to reduce the cost to screen for risk for AD, and are less invasive and more acceptable to AD patients than, for example, the lumbar puncture test currently used to obtain cerebral spinal fluid (CSF) or PET imaging. These assays and methods for diagnosis of Aβ peptide related conditions can further be combined with the treatment methods described herein to provide theranostic methods for the diagnosis and inhibition or improvement of patients suffering from Aβ peptide-mediated disorders, like Alzheimer's.

Amyloid Diseases and Alzheimer's Disease

The compositions, methods and assays described herein are useful for the treatment and diagnosis of amyloid diseases mediated by Aβ peptide. "Amyloidosis," as used herein, refers to a condition found in a variety of diseases that is characterized by an accumulation of amyloid material in the organs or tissues of the body. This accumulation can impair vital functions. "Amyloid," as used herein, is a term referring to a group of diverse but specific extracellular protein deposits that all have common morphological properties, staining characteristics, and X-ray diffraction spectra. Regardless of the nature of the amyloid protein deposited, amyloids have the following characteristics: 1) showing an amorphous appearance at the light microscopic level, appearing eosinophilic using hematoxylin and eosin stains; 2) staining with Congo red and demonstrating a red/green birefringence as viewed under polarized light (Puchtler et al., J. Histochem. Cytochem. 10:355-364, 1962); 3) containing a predominant beta-pleated sheet secondary structure; and 4) ultrastructurally comprising non-branching fibrils of indefinite length and with a diameter of 7-10 nm.

Amyloidoses are classified according to the specific amyloid protein deposited. The amyloids include, but are not limited to, "beta-amyloid protein" or "Aβ," the amyloid associated with Alzheimer's disease, Down's syndrome and hereditary cerebral hemorrhage with amyloidosis of the Dutch type; "AA amyloid" or "inflammation-associated amyloid," the amyloid associated with chronic inflammation, various forms of malignancy and familial Mediterranean fever; "AL amyloid," the amyloid associated with multiple myeloma and other B-cell dyscrasias; "amylin" or "islet amyloid," the amyloid associated with type II diabetes; "PrP amyloid," the amyloid associated with the prion diseases including Creutzfeldt-Jakob disease, Gerstmann-Straussler syndrome, kuru, and scrapie; "β2-microglobulin amyloid," the amyloid associated with long-term hemodialysis and carpal tunnel syndrome; "prealbumin" or "transthyretin amyloid," the amyloid associated with senile cardiac amyloid and familial amyloidotic polyneuropathy; variants of "procalcitonin," the amyloid associated with endocrine tumors such as medullary carcinoma of the thyroid; and the amyloid associated with progressive supranuclear palsy and multiple sclerosis.

Although amyloid deposits in clinical conditions share common physical properties relating to the presence of a beta-pleated sheet conformation, it is clear that many different chemical types exist and additional ones are likely to be described in the future. It is currently thought that there are several common pathogenetic mechanisms that can be operating in amyloidosis in general. In many cases, a circulating precursor protein can result from overproduction of either intact or aberrant molecules (for example, in plasma cell dyscrasias), reduced degradation or excretion (serum amyloid A in some secondary amyloid syndromes and β2 microglobulin in long-term hemodialysis), or genetic abnormalities associated with variant proteins (for example, familial amyloidotic polyneuropathy). Proteolysis of a larger protein precursor molecule occurs in many types of amyloidosis, resulting in the production of lower molecular weight fragments that polymerize and assume a beta-pleated sheet conformation as tissue deposits, usually in an extracellular location.

Systemic amyloids, which include the amyloid associated with chronic inflammation, various forms of malignancy and familial Mediterranean fever (i.e., AA amyloid or inflammation-associated amyloidosis) (Benson and Cohen, Arth. Rheum. 22:36-42, 1979; Kamei et al, Acta Path. Jpn. 32:123-133, 1982; McAdam et al., Lancet 2:572-573, 1975; Metaxas, Kidney Int. 20:676-685, 1981), and the amyloid associated with multiple myeloma and other B-cell dyscrasias (i.e. AI. amyloid) (Harada et al., J. Histochem. Cytochem. 19:1-15, 1971), as examples, are known to involve amyloid deposition in a variety of different organs and tissues generally lying outside the central nervous system. Amyloid deposition in these diseases may occur, for example, in liver, heart, spleen, gastrointestinal tract, kidney, skin, and/or lungs (Johnson et al, N. Engl. J. Med. 321:513-518, 1989). For most amyloidoses, there is no apparent cure or effective treatment and the consequences of amyloid deposition can be detrimental to the patient. For example, amyloid deposition in the kidney can lead to renal failure, whereas amyloid deposition in the heart can lead to heart failure. For these patients, amyloid accumulation in systemic organs leads to eventual death generally within 3-5 years.

Other amyloidoses can affect a single organ or tissue such as observed with the Aβ amyloid deposits found in the brains of patients with Alzheimer's disease and Down's syndrome: the PrP amyloid deposits found in the brains of patients with Creutzfeldt-Jakob disease, Gerstmann-Straussler syndrome, and kuru; the islet amyloid (amylin) deposits found in the islets of Langerhans in the pancreas of 90% of patients with type II diabetes (Johnson et al, N. Engl. J. Med. 321:513-518, 1989; Lab. Invest. 66:522 535, 1992); β2-microglobulin amyloid deposits in the medial nerve leading to carpal tunnel syndrome as observed in patients undergoing long-term hemodialysis (Geyjo et al, Biochem. Biophys. Res. Comm. 129:701-706, 1985; Kidney Int. 30:385-390, 1986); the prealbumin/transthyretin amyloid observed in the hearts of patients with senile cardiac amyloid; and the prealbumin/transthyretin amyloid observed in peripheral nerves of patients who have familial amyloidotic polyneuropathy (Skinner and Cohen, Biochem. Biophys. Res. Comm. 99:1326-1332, 1981; Saraiva et al, J. Lab. Clin. Med. 102:590-603, 1983; J. Clin. Invest. 74:104-119, 1984; Tawara et al, J. Lab. Clin. Med. 98:811-822, 1989).

A number of impairments specific to amyloid deposits in the brain are linked with the deposition of the peptide, Aβ peptide (amyloid-β peptide), a 4 kD protein, 39-43 amino acids long. Aβ peptide is expressed by a gene located on chromosome 21. Aβ is formed after sequential cleavage of the amyloid precursor protein (APP), a transmembrane glycoprotein that is much larger (770 amino acid residues). APP can be processed by α-, β- and γ-secretases; Aβ protein is generated by successive action of the β and γ secretases. The γ secretase, which produces the C-terminal end of the Aβ peptide, cleaves within the transmembrane region of APP and can generate a number of isoforms of 36-43 amino acid residues in length. As used herein, the terms "Aβ peptide" or "Aβ" refer to the peptides generated by the successive action of the β and γ secretases, such as Aβ40 and Aβ42. The most common isoforms are Aβ40 and Aβ42. The shorter form, Aβ40 (DAEFRHDSGYEVHHQKLVFFAED-VGSNKGAIIGLMVGGVV; SEQ ID NO: 1) is typically produced by cleavage that occurs in the endoplasmic reticulum. The the longer form, Aβ42, (DAEFRHDSGYEVH-HQKLVFFAEDVGSNKGAIIGLMVGGVVIA; SEQ ID NO: 2) is produced by cleavage in the trans-Golgi network. The Aβ40 form is the more common of the two, but Aβ42 is the more fibrillogenic and is thus associated with disease states. Mutations in APP associated with early-onset Alzheimer's have been noted to increase the relative production of Aβ42. Neurological diseases associated with Aβ peptide deposition, amenable for treatment with the methods and diagnostic assays described herein, include Alzheimer's, Lewy body dementia, Down's Syndrome, hereditary cerebral hemorrhage with amyloidosis (Dutch type), and the Guamanian Parkinsonism-Dementia. Aβ peptide plaques also occur in persons who have experienced head trauma and critical coronary disease.

The most common disease related to cognitive decline or dementia is Alzheimer's Disease (AD). This condition is characterized by neuronal loss, neurofibrillary tangles, and neuritic plaques comprised of Aβ peptide. After excision, Aβ peptide is polymerized into amyloid filaments, which in turn aggregate into amyloid plaque deposits. In the brain, these filaments and aggregates, or possibly intermediate protofilaments, are toxic to neurons and are believed to lead to neurofibrillary tangles, synapse loss, and neurodegeneration that underlie the decline of cognitive functions in Alzheimer's patients.

Due to the nature of cerebral amyloidosis, diagnosis or determination of Alzheimer's before death is difficult and the development of therapies or other treatments for Alzheimer's have been elusive. Many therapies are unable to cross the blood-brain barrier in amounts necessary for effective treatment. The inability to examine amyloid deposition of AD in patients before death impedes the ability of researchers to study AD and develop effective therapies targeted at preventing or reversing amyloid plaque formation on the brain. Damage to CNS neurons due to AD begins years before clinical symptoms are evident. Non-invasive and reliable methods to determine whether a subject is at risk for or has Alzheimer's disease, as provided in the methods and assays described herein, are useful for early and preventative and inhibitory therapeutic interventions. In addition, prevention or reduction of amyloidosis in the brain, as demonstrated herein using amylin or amylin analog injections, can prevent or inhibit or slow the development of AD.

By definition, AD is currently diagnosed through the examination of brain tissue, usually at autopsy. The currently recommended "minimum microscopic criteria" for AD diagnosis is based on the number of neuritic plaques found in the brain. The amyloid cores of these neuritic plaques are composed of β-amyloid protein, also referred to herein as amyloid-β or Aβ peptide, that is arranged in a predominately beta-pleated sheet configuration. Brain amyloid plaques are demonstrated by staining brain sections with thioflavin S or Congo red. Congo red-stained amyloid is characterized by a dichroic appearance, exhibiting a yellow-green polarization color. The dichroic binding is the result of the beta-pleated sheet structure of the amyloid proteins.

In addition to Alzheimer's, the compositions, methods, and assays described herein can also be used for patients having "amnestic mild cognitive impairment" ("aMCI"), which is a prodromal phase of Alzheimer's that has a fairly high rate of conversion to Alzheimer's disease. People with aMCI experience significant memory impairment; however, they tend to retain their other cognitive functions. This allows them to keep their independence and live day-to-day without major disruption. aMCI patients also typically respond well to rehabilitation and cognitive aids to restore their memory breakdown.

Amylin or Insulin Amyloid Polypeptide and Agonist Peptides Thereof

As demonstrated herein, the inventors have discovered that the glucoregulatory hormone amylin and its analogs are useful in the treatment and diagnosis of Alzheimer's disease and other disorders that are mediated by deposition of Aβ peptide. Amylin, which is also referred to herein as "Insulin Amyloid Polypeptide" (IAP), is a hormone that is co-secreted with insulin from pancreatic β cells and has been shown to have numerous metabolic effects, including glucoregulatory actions. The glucoregulatory actions of amylin are related to its effects on gastric emptying, suppression of inappropriately elevated postprandial glucagon secretion, and inhibition of food intake (Young (1997) Curr. Opin. in Endocrinology and Diabetes 4:282-290). Amylin is believed to aid in limiting glycemic excursions by slowing gastric emptying, promoting satiety, and inhibiting inappropriate secretion of glucagon, a catabolic hormone that opposes the effects of insulin and amylin. SYMLIN™ (pramlintide acetate) is a synthetic analog of Amylin that has been approved by the FDA for use in the the treatment of type 1 and 2 diabetes (Baron et al. (2002) Curr. Drug Targets Immune Endocr. Metabol. Disord. 2:63-82). Amylin agonists include amylin agonist analogs, examples of which are described in U.S. Pat. Nos. 5,686,411; 6,610,824; 5,998,367; 6,087,334; PCT Application No. PCT/US2005/004631, US Publication No. 2008/0176804,US Publication No. 20120071401, and US Publication No. 20120197796, the contents of each of which are incorporated herein by reference in their entireties, and as described herein.

Accordingly, as used herein, by "amylin" or "Insulin Amyloid Polypeptide (IAP or IAPP)," is meant the human peptide hormone of 37 amino acids referred to as amylin, which is co-secreted with insulin from β-cells of the pancreas, and polymorphic and species variations thereof, examples of which are described in U.S. Pat. No. 5,234,906, the contents of which are hereby incorporated by reference in their entireties. Human amylin has the following amino acid sequence: Lys-Cys-Asn-Thr-Ala-Thr-Cys-Ala-Thr-Gln-Arg-Leu-Ala-Asn-Phe-Leu-Val-His-Ser-Ser-Asn-Asn-Phe-Gly-Ala-Ile-Leu-Ser-Ser-Thr-Asn-Val-Gly-Ser-Asn-Thr-Tyr or KCNTATCATQRLANFLVHSSNNFGAILSSTNVGSNTY —(NH2) (SEQ ID NO: 3), and comprises a disulfidebridge between the two Cys residues and an amide group attached to the C-terminal amino acid via a peptide bond. The term "amylin" also includes variants of amylin as present in, and in isolatable form, other mammalian species, such as rat amylin (KCNTATCATQRLANFLVRSSNNFGPVLPPTNVGSNTY —(NH2); SEQ ID NO: 5), monkey amylin (Lys Cys Asn Thr Ala Thr Cys Ala Thr Gln Arg Leu Ala Asn Phe Leu Arg His Ser Ser Asn Asn Phe Gly Thr Ile Leu Ser Ser Thr Asn Val Gly Ser Asp Thr Tyr; SEQ ID NO: 6); cat amylin (Lys Cys Asn Thr Ala Thr Cys Ala Thr Gln Arg Leu Ala Asn Phe Leu Ile Arg Ser Ser Asn Asn Leu Gly Ala Ile Leu Ser Pro Thr Asn Val Gly Ser Asn Thr Tyr; SEQ ID NO: 7); dog amylin (Lys Cys Asn Thr Ala Thr Cys Ala Thr Gln Arg Leu Ala Asn Phe Leu Val Arg Thr Ser Asn Asn Leu Gly Ala Ile Leu Ser Pro Thr Asn Val Gly Ser Asn Thr Tyr; SEQ ID NO: 8); mouse amylin (Lys Cys Asn Thr Ala Thr Cys Ala Thr Gln Arg Leu Ala Asn Phe Leu Val Arg Ser Ser Asn Asn Leu Gly Pro Val Leu Pro Pro Thr Asn Val Gly Ser Asn Thr Tyr; SEQ ID NO: 9); hamster amylin (Lys Cys Asn Thr Ala Thr Cys Ala Thr Gln Arg Leu Ala Asn Phe Leu Val Arg Ser Ser Asn Asn Leu Gly Pro Val Leu Ser Pro Thr Asn Val Gly Ser Asn Thr Tyr; SEQ ID NO: 10); guinea pig amylin (Lys Cys Asn Thr Ala Thr Cys Ala Thr Gln Arg Leu Thr Asn Phe Leu Val Arg Ser Ser His Asn Leu Gly Ala Ala Leu Leu Pro Thr Asn Val Gly Ser Asn Thr Tyr; SEQ ID NO: 11); and degu amylin (Lys Cys Asn Thr Ala Thr Cys Ala Thr Gln Arg Leu Thr Asn Phe Leu Val Arg Ser Ser Asn Asn Leu Gly Ala Ala Leu Pro Thr Lys Val Gly Ser Asn Thr Tyr; SEQ ID NO: 12); and pharmaceutically acceptable salts of any of these compounds. With respect to a naturally occurring amylin compound, the term includes such a compound in an isolated, purified, or other form that is otherwise not found in nature.

The 37 amino acid long natural human amylin peptide has physico-chemical properties that make its use as a drug challenging. In particular, it has a tendency to fibrillate ex vivo and become ineffective due to precipitation. Accordingly, also provided herein for use in the compositions, methods, and assays described herein, are amylin analogs. As used herein, an "amylin analog" or "amylin agonist compound" is a molecule that has properties that are as good as or better than the parent amylin compound. The amylin analog has the same physiological effects as amylin, including, for example, glucose regulation and having the ability to traverse the blood brain area, but having, for example, one or more amino acid variations that, for example, enhance its effectiveness as a drug or increases solubility, or otherwise increases its therapeutic properties, such as superior stability, solubility, efficacy, half-life, and the like. In some embodiments of the aspects described herein, an analog is a compound that has at least 75% sequence identity to the parent compound, at least 80% sequence identity, at least 85% sequence identity, at least 90% sequence identity, or at least 95% sequence identity to the parent compound.

Amylin agonist compounds include amylin analog peptides, and other compounds (e.g., small molecules) that have amylin agonist activity. The "amylin agonist compounds" can be derived from natural sources, can be synthetic, or can be derived from recombinant DNA techniques. Amylin agonist peptides have amylin agonist receptor binding activity and can comprise amino acids (e.g., natural, unnatural, or a combination thereof), peptide mimetics, chemical moieties, and the like. The skilled artisan can recognize amylin agonist compounds using amylin receptor binding assays or by measuring amylin agonist activity in soleus muscle assays. In some embodiments, amylin agonist compounds have an $IC_{50}$ of about 200 or less, about 100 or less, or about 50 or less, in an amylin receptor binding assay, such as that described in U.S. Pat. No. 5,686,411, US Publication No. 2008/0176804, and US Publication No. 20120071401, the contents of which are incorporated by reference herein. In some embodiments, amylin agonist compounds have an $IC_{50}$ of about 20 or less, about 15 or less, about 10 or less, or about 5 or less in a soleus muscle assay, such as that described in U.S. Pat. No. 5,686,411 and and US Publication No. 20120071401, the contents of which are incorporated by reference herein. In some embodiments of the aspects described herein, the amylin agonist compound has at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 3 or SEQ ID NO: 4. In some embodiments of the aspects described herein, the amylin agonist compound is a peptide chimera of amylin (e.g., human amylin (SEQ ID NO: 3), rat amylin (SEQ ID NO: 5), and the like) and another molecule, such as one that can enhance the ability to traverse the blood brain barrier, for example. Unless otherwise stated, reference to "amylin" includes amylin and amylin analogs having similar function and structure that can be used in the assays and methods described herein.

The nomenclature for the compounds described herein is used to indicate (1) the peptide that the amino acid sequence is based on and (2) the modifications that have been made to that amino acid sequence. An amino acid preceded by a superscript number indicates that the named amino acid replaces the amino acid normally present at that particular amino acid position in the amino acid sequence. For example, $^{18}$Arg$^{25,28}$Pro-human amylin refers to a peptide based on the amino acid sequence of human amylin (i.e., SEQ ID NO: 3) and which has the following substitutions: Arg replaces His at position 18 in human amylin; Pro replaces Ala at position 25 in human amylin; and Pro replaces Ser at position 28 in human amylin. Similarly, del-$^1$Lys-human amylin refers to a peptide based on the amino acid sequence of human amylin except that the Lys at position 1 (i.e., $^1$Lys) is deleted (i.e., del) from the amino acid sequence.

In some embodiments of the methods and assays described herein, the amylin analog is pramlintide or SEQ ID NO: 4. SYMLIN™ is currently on the market and is an analog of human amylin (generic name: pramlintide), in which the three amino acids at positions 25, 28 and 29 each are substituted to proline (KCNTATCATNRLAN-FLVHSSNNFGPILPPTNVGSNTY —(NH2), SEQ ID NO: 4), and which has substantially decreased fibrillating tendency. However, even pramlintide can be difficult to keep in solution at neutral pH and it is therefore provided in an acidic solution.

Other amylin analogs contemplated for use in the compositions, treatment methods, and assays described herein include, for example:

CNTATCATQRLANFLVHSSNNFGAILSSTNVGSNTY (SEQ ID NO: 13), where $^1$C and $^6$C are optionally linked by a disulfide bond and $^{36}$Y is optionally amidated;

KCNTATCATQRLANFLIRSSNNLGAILSSTNVGSNTY (SEQ ID NO: 14), where $^2$C and $^7$C are optionally linked by a disulfide bond; and $^{37}$Y is optionally amidated;

KCNTATCATQRLANFLIRSSNNLGAVLSPTNVGSNTY (SEQ ID NO: 15), where $^2$C and $^7$C are optionally linked by a disulfide bond; and $^{37}$Y is optionally amidated;

KCNTATCATQRLANFLVHSSNNFGPILSSTNVGSNTY (SEQ ID NO: 16), where $^2$C and $^7$C are optionally linked by a disulfide bond; and $^{37}$Y is optionally amidated;

KCNTATCATQRLANFLVHSSNNFGAILPSTNVGSNTY (SEQ ID NO: 17), where $^2$C and $^7$C are optionally linked by a disulfide bond; and $^{37}$Y is optionally amidated;

KCNTATCATQRLANFLVHSSNNFGAILSPTNVGSNTY (SEQ ID NO: 18), where $^2$C and $^7$C are optionally linked by a disulfide bond; and $^{37}$Y is optionally amidated;

KCNTATCATQRLTNFLVRSSHNLGAALSPTDVGSNTY (SEQ ID NO: 19), where $^2$C and $^7$C are optionally linked by a disulfide bond; and $^{37}$Y is optionally amidated;

KCNTATCATQRLTNFLVHSSHNLGAALLPTDVG-SNTY (SEQ ID NO: 20), where $^2$C and $^7$C are optionally linked by a disulfide bond; and $^{37}$Y is optionally amidated;

KCNTATCATQRLTNFLVHSSHNLGAALSPTDVGSNTY (SEQ ID NO: 21), where $^2$C and $^7$C are optionally linked by a disulfide bond; and $^{37}$Y is optionally amidated;

CNTATCATQRLTNFLVHSSHNLGAALSPTDVGSNTY (SEQ ID NO: 22), where $^1$C and $^6$C are optionally linked by a disulfide bond; and $^{36}$Y is optionally amidated;

CNTATCATQRLANFLVHSSNNFGPILPPTNVGSNTY (SEQ ID NO: 23), where C and $^6$C are optionally linked by a disulfide bond; and $^{36}$Y is optionally amidated;

KCNTATCATQRLANFLVRSSNNFGPILPPTNVGSNTY (SEQ ID NO: 24), where $^2$C and $^7$C are optionally linked by a disulfide bond; and $^{37}$Y is optionally amidated;
CNTATCATQRLANFLVRSSNNFGPVLPPTNVGSNTY (SEQ ID NO: 25), where $^1$C and $^6$C are optionally linked by a disulfide bond; and $^{36}$Y is optionally amidated;
KCNTATCATQRLANFLVHSSNNFGPILPPTNVGSNTY (SEQ ID NO: 26), where $^2$C and $^7$C are optionally linked by a disulfide bond; and $^{37}$Y is optionally amidated;
KCNTATCATQRLANFLIHSSNNFGPILPPTNVGSNTY (SEQ ID NO: 27), where $^2$C and $^7$C are optionally linked by a disulfide bond; and $^{37}$Y is optionally amidated;
KCNTATCATQRLANFLVHSSNNLGPVLPPTNVGSNTY (SEQ ID NO: 28), where $^2$C and $^7$C are optionally linked by a disulfide bond; and $^{37}$Y is optionally amidated;
KCNTATCATQRLANFLVRSSNNLGPILPPTNVGSNTY (SEQ ID NO: 29), where $^2$C and $^7$C are optionally linked by a disulfide bond; and $^{37}$Y is optionally amidated;
KCNTATCATQRLANFLIHSSNNLGPILPPTNVGSNTY (SEQ ID NO: 30), where $^2$C and $^7$C are optionally linked by a disulfide bond; and $^{37}$Y is optionally amidated;
CNTATCATQRLANFLIHSSNNLGPILPPTNVGSNTY (SEQ ID NO: 31), where $^1$C and $^6$C are optionally linked by a disulfide bond; and $^{36}$Y is optionally amidated;
KCNTATCATQRLANFLIRSSNNRGPVLPPTNVGSNTY (SEQ ID NO: 32), where $^2$C and $^7$C are optionally linked by a disulfide bond; and $^{37}$Y is optionally amidated;
KCNTATCATQRLTNFLVRSSHNLGPALPPTDVGSNTY (SEQ ID NO: 33), where $^2$C and $^7$C are optionally linked by a disulfide bond; and $^{37}$Y is optionally amidated;
KCNTATCATQRLANFLVRSSNNFGPILPSTNVGSNTY (SEQ ID NO: 34), where $^2$C and $^7$C are optionally linked by a disulfide bond; and $^{37}$Y is optionally amidated;
CNTATCATQRLANFLVRSSNNFGPILPSTNVGSNTY (SEQ ID NO: 35), where $^1$C and $^6$C are optionally linked by a disulfide bond; and $^{36}$Y is optionally amidated;
KCNTATCATQRLANFLVRSSNNLGPILPSTNVGSNTY (SEQ ID NO: 36), where $^2$C and $^7$C are optionally linked by a disulfide bond; and $^{37}$Y is optionally amidated;
KCNTATCATQRLANFLVHSSNNLGPVLPSTNVGSNTY (SEQ ID NO: 37), where $^2$C and $^7$C are optionally linked by a disulfide bond; and $^{37}$Y is optionally amidated;
CNTATCATQRLANFLVHSSNNLGPVLPSTNVGSNTY (SEQ ID NO: 38), where $^1$C and $^6$C are optionally linked by a disulfide bond; and $^{36}$Y is optionally amidated;
KCNTATCATQRLANFLVRSSNNLGPVLPSTNVGSNTY (SEQ ID NO: 39), where $^2$C and $^7$C are optionally linked by a disulfide bond; and $^{37}$Y is optionally amidated;
KCNTATCATQRLANFLVHSSNNFGPILPSTNVGSNTY (SEQ ID NO: 40), where $^2$C and $^7$C are optionally linked by a disulfide bond; and $^{37}$Y is optionally amidated;
KCNTATCATQRLTNFLVRSSHNLGAILPPTDVGSNTY (SEQ ID NO: 41), where $^2$C and $^7$C are optionally linked by a disulfide bond; and $^{37}$Y is optionally amidated;
KCNTATCATQRLANFLVHSSNNFGAILPPTNVGSNTY (SEQ ID NO: 42), where $^2$C and $^7$C are optionally linked by a disulfide bond; and $^{37}$Y is optionally amidated;
KCNTATCATQRLANFLVHSSNNFGPILSPTNVGSNTY (SEQ ID NO: 43), where $^2$C and $^7$C are optionally linked by a disulfide bond; and $^{37}$Y is optionally amidated;
KCNTATCVLGRLSQELHRLQTYPRTNTGSNTY (SEQ ID NO: 44), where $^2$C and $^7$C are optionally linked by a disulfide bond; and $^{32}$Y is optionally amidated; and pharmaceutically acceptable salts of any of these peptides and variants thereof. Other amylin analogs contemplated for use in the compositions, methods, and assays described herein can be found in US Patent Publications US 2012/0071401 and US 2012/0196796, the contents of which are herein incorporated by reference in their entireties.

In some embodiments, amylin or the amylin analog peptides described herein can be further modified. In some such embodiments, the amylin or analog peptide being modified comprises SEQ ID NO: 3 or SEQ ID NO: 4. In general, with respect to an amino acid sequence, the term "modification" includes substitutions, insertions, elongations deletions, and derivatizations, alone or in combination. Amylin or the amylin analog peptides described herein can include one or more modifications of a "non-essential" amino acid residue. As used herein, a "non-essential" amino acid residue is a residue that can be altered, i.e., deleted or substituted, in the amino acid sequence without abolishing or substantially reducing the agonist activity of the analog peptide.

Substitutions include conservative amino acid substitutions. As used herein, a "conservative amino acid substitution" is one in which the amino acid residue is replaced with an amino acid residue having a similar side chain, or physicochemical characteristics (e.g., electrostatic, hydrogen bonding, isosteric, hydrophobic features). The amino acids can be naturally occurring or nonnatural (unnatural). Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, methionine, cysteine), nonpolar side chains (e.g., alanine, valine, leucine, isoleucine, proline, phenylalanine, tryptophan), β-branched side chains (e.g., threonine, valine, isoleucine) and aromatic side chains (e.g., tyrosine, phenylalanine, tryptophan, histidine). Substitutions may also include non-conservative changes.

By "amino acid" and "amino acid residue" is meant natural amino acids, unnatural amino acids, and modified amino acid. Unless stated to the contrary, any reference to an amino acid, generally or specifically by name, includes reference to both the D and the L stereoisomers if their structure allow such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to homolysine, homoarginine, homoserine azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline. Additional unnatural amino acids include modified amino acid residues which are chemically blocked, reversibly or irreversibly, or chemically modified on their N-terminal amino group or their side chain groups, as for example, N-methylated D and L amino acids or residues wherein the side chain functional groups are chemically modified to another functional group. For example, modified amino acids include methionine sulfoxide; methionine sulfone; aspartic acid-(beta-methyl ester), a modified amino acid of aspartic acid; N-ethylglycine, a modified amino acid of glycine; or alanine carboxamide, a modified amino acid of alanine Additional residues that can be incorporated are described in Sandberg et al., J. Med. Chem. 41: 2481-91, 1998.

In some embodiments of the methods and assays described herein, the amylin analog compounds and variants thereof can comprise other chemical modifications that can involve adding chemical moieties, creating new bonds, and removing chemical moieties, such as amidation, glycosylation, acylation, sulfation, phosphorylation, acetylation, and cyclization. Exemplary modifications at amino acid side groups include acylation of lysine E-amino groups, N-alkylation of arginine, histidine, or lysine, alkylation of glutamic or aspartic carboxylic acid groups, and deamidation of glutamine or asparagine. Exemplary modifications of the terminal amino group include the desamino, N-lower alkyl, N-di-lower alkyl, and N-acyl modifications, such as alkyl acyls, branched alkylacyls, alkylaryl-acyls. Exemplary modifications of the terminal carboxy group include the amide, lower alkyl amide, dialkyl amide, arylamide, alkylarylamide and lower alkyl ester modifications. Lower alkyl is $C_{1-4}$ alkyl. Furthermore, one or more side groups, or terminal groups, can be protected by protective groups known to the skilled artisan. The α-carbon of an amino acid can be mono- or dimethylated.

The amylin peptides and amylin analogs described herein can, in some embodiments of the methods and assays described herein, form pharmaceutically acceptable salts with various inorganic acids, organic acids, and bases. Exemplary salts prepared with organic and inorganic acids include HCl, HBr, $H_2SO_4$, $H_3PO_4$, trifluoroacetic acid, acetic acid, formic acid, methanesulfonic acid, toluenesulfonic acid, maleic acid, fumaric acid, camphorsulfonic acid, and the like. Exemplary salts prepared with bases include ammonium salts, alkali metal salts (such as sodium and potassium salts) and alkali earth salts (such as calcium and magnesium salts). In some embodiments, the pharmaceutically acceptable salt is an acetate salt, a hydrochloride salt, or a trifluoroacetate salt. The pharmaceutically acceptable salts can be formed by conventional means, as by reacting the free acid or base forms of the compounds with one or more equivalents of the appropriate base or acid in a solvent or medium in which the salt is insoluble, or in a solvent such as water, which is then removed in vacuo or by freeze-drying, or by exchanging the ions of an existing salt for another ion on a suitable ion exchange resin.

In some embodiments of the aspects described herein, the amylin peptides and amylin analogs described herein can be linked to one or more polymers to provide additional beneficial biological properties. Such additional beneficial biological properties may include, e.g., providing additional therapeutic activity to the compound; increasing the ability to traverse the blood brain barrier, increasing the in vivo half life of the compound, decreasing the rate of clearance of the compound by the kidney, decreasing the immunogenicity of the compound, decreasing the proteolysis rate of the compound, or increasing the stability of the compound. Exemplary polymers that can be linked to the amylin agonist compounds include, but are not limited to, peptides, saccharides, polyethylene glycols, albumin, fatty acids, polyamino acids, dextran, gelatin, polyvinyl pyrrolidone, polyvinyl alcohol, N-(2-hydroxypropyl)-methacrylamide, and the like. In one embodiment, the amylin agonist compounds are linked to peptides, saccharides, polyethylene glycols, albumin, fatty acids, and polyamino acids.

When the amylin analog compounds described herein are linked to one or more polymers, in some embodiments, any linking group known in the art can be used. The linking group can comprise any chemical group(s) suitable for linking the compound to the polymer. Exemplary linking groups include amino acids, maleimido groups, dicarboxylic acid groups, succinimide groups, or a combination of two or more thereof. Alternatively, in some embodiments, the amylin analog compound can be directly attached to the polymer without any linking group. Methods for linking compounds to one or more polymers are known in the art and described, for example, in U.S. Pat. Nos. 6,329,336; 6,423,685; 6,924,264; WO 2007/022123; WO 2007/053946; WO 2008/058461; and WO 2008/082274, the contents of which are incorporated by reference in their entireties herein.

Amylin or Amylin Analog Pharmaceutical Compositions, Methods, and Uses Thereof

Provided herein, in some aspects, are pharmaceutical compositions comprising amylin or amylin analogs for use in the methods of methods of reducing and/or inhibiting Aβ deposition or Aβ plaque formation in the brain, and/or inhibiting or slowing the progression of disorders mediated by Aβ deposition or Aβ plaque formation, such as Alzheimer's disease described herein.

Accordingly, in some aspects, provided herein is an amylin or an amylin analog for use in reducing Aβ peptide deposition in the brain of a subject. Provided herein, in some aspects, is an amylin or an amylin analog for use in inhibiting progression of Alzheimer's disease or amnestic mild cognitive impairment in a subject.

In some embodiments of these uses and all such uses described herein, the amylin or an amylin analog is formulated for administration to a subject at least once a week.

In some embodiments of these uses and all such uses described herein, the amylin or an amylin analog is formulated for administration to a subject at least twice a week.

In some embodiments of these uses and all such uses described herein, the amylin or an amylin analog is formulated for administration to a subject at least three times a week.

In some embodiments of these uses and all such uses described herein, the amylin or an amylin analog is formulated for administration to a subject at least four times a week.

In some embodiments of these uses and all such uses described herein, the amylin or an amylin analog is formulated for administration to a subject daily.

In some embodiments of these uses and all such uses described herein, the amylin or an amylin analog is formulated for administration to a subject by injection. In some embodiments of these uses, the injection is a systemic injection.

In some embodiments of these uses and all such uses described herein, the amylin or amylin analog comprises a sequence of SEQ ID NO: 3, SEQ ID NO: 4, or SEQ ID NOs: 13-44.

In some embodiments of these uses and all such uses described herein, the amylin or amylin analog is formulated as a unit dose composition.

In some embodiments of these uses and all such uses described herein, the subject having Aβ peptide deposition in the brain has or is at risk for Alzheimer's disease or amnestic mild cognitive impairment (aMCI).

Also provided herein, in some aspects, are pharmaceutical compositions comprising a therapeutically or prophylactically effective amount of amylin or an amylin analog, or a pharmaceutically acceptable salt thereof, together with pharmaceutically acceptable diluents, preservatives, solubilizers, emulsifiers, adjuvants and/or carriers useful in the delivery of the of amylin or amylin analog. Such compositions can include diluents of various buffer content (e.g., acetate, citrate, tartrate, phosphate, TRIS), pH and ionic strength; additives such as surfactants and solubilizing agents (e.g., sorbitan monooleate, lecithin, Pluronics, Tween 20 & 80, Polysorbate 20 & 80, propylene glycol, ethanol, PEG-40, sodium dodecyl sulfate), anti-oxidants (e.g., monothioglyercol, ascorbic acid, acetylcysteine, sulfurous acid salts (bisulfise and metabisulfite), preservatives (e.g., phenol, meta-cresol, benzyl alcohol, parabens (methyl, propyl, butyl), benzalkonium chloride, chlorobutanol, thimersol, phenylmercuric salts, (acetate, borate, nitrate), and tonicity/ bulking agents (glycerine, sodium chloride, mannitol, sucrose, trehalose, dextrose) incorporation of the material into particulate preparations of polymeric compounds, such as polylactic acid, polyglycolic acid, etc., or in association with liposomes. Such compositions will influence the physical state, stability, rate of in vivo release, and rate of in vivo clearance of the present compounds. See, e.g., Remington's Pharmaceutical Sciences 1435-712, 18th ed., Mack Publishing Co., Easton, Pa. (1990).

The pharmaceutical formulations can be stabilized at neutral pH. Since the amylin agonist compounds are amphoteric they may be utilized as free bases, as acid addition salts, or as metal salts. A wide variety of pharmaceutically acceptable acid addition salts are available, as described above. These include those prepared from both organic and inorganic acids, preferably mineral acids. Typical acids which may be mentioned by way of example include acetic, citric, succinic, lactic, hydrochloric and hydrobromic acids. Such products are readily prepared by procedures well known in the art.

The pharmaceutical compositions comprising amylin or amylin analogs described herein can, in some embodiments, be formulated for peripheral administration, including formulation for injection or other types of administration as one skilled in the art will recognize. Examples of formulations can be found in U.S. Pat. No. 6,410,511 and patent application Ser. No. 10/159,779, the contents of which are incorporated herein by reference in their entireties. Administration of the pharmaceutical compositions comprising amylin or amylin analogs can be via any common route so long as the target tissue or organ, e.g., the brain, can be accessed via that route. The treatment can consist of a single dose or, in some embodiments, a plurality of doses over a period of time. Controlled continual release of the compositions of the present invention is also contemplated, as described herein. Examples of microsphere technology can be found in U.S. Pat. Nos. 6,458,387 and 5,578,708, incorporated herein by reference in their entirety.

The formulation of the pharmaceutical compositions comprising amylin or amylin analogs can, in some embodiments, be liquid or can be solid, such as lyophilized, for reconstitution. Aqueous pharmaceutical compositions comprise an effective amount of the amylin or amylin analogs, dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in therapeutic compositions is contemplated. Supplementary active ingredients also can be incorporated into the compositions. For example, in some embodiments, the amylin or amylin analog can be provided along with another therapeutic agent known to have effects on disorders mediated by Aβ deposition or Aβ plaque formation, such as Alzheimer's disease, in a single composition or solution for administration together. In other embodiments, it can be more advantageous to administer the additional therapeutic agent separately from the the amylin or amylin analog.

The pharmaceutical compositions comprising amylin or amylin analogs described herein can, in some embodiments, be prepared for administration as solutions of free base, or pharmacologically acceptable salts in water suitably mixed with a surfactant, such as hydroxypropylcellulose. As used herein, the phrase "pharmaceutically acceptable salts" refers to salts prepared from pharmaceutically acceptable, preferably nontoxic, acids and bases, including inorganic and organic acids and bases, including but not limited to, sulfuric, citric, maleic, acetic, oxalic, hydrochloride, hydro bromide, hydro iodide, nitrate, sulfate, bisulfite, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-nap-hthoate)) salts. Pharmaceutically acceptable salts include those formed with free amino groups such as, but not limited to, those derived from hydrochloric, phosphoric, acetic, oxalic, and tartaric acids. Pharmaceutically acceptable salts also include those formed with free carboxyl groups such as, but not limited to, those derived from sodium, potassium, ammonium, sodium lithium, calcium, ferric hydroxides, isopropylamine, triethylamine, 2-ethylamino ethanol, histidine, and procaine. Under ordinary conditions of storage and use, these preparations contain a preservative to prevent the growth of microorganisms.

In some embodiments of the aspects described herein, the pharmaceutical compositions comprising amylin or amylin analogs described herein are formulated so as to be suitable for parenteral administration, e.g., via injection or infusion. Preferably, the amylin or amylin analog described herein is suspended in an aqueous carrier, for example, in an isotonic buffer solution at a pH of about 3.0 to about 8.0, preferably at a pH of about 3.0 to about 7.4, 3.5 to 6.0, or 3.5 to about 5.0. Useful buffers include sodium acetate/acetic acid, sodium lactate/lactic acid, ascorbic acid, sodium citrate-citric acid, sodium bicarbonate/carbonic acid, sodium succinate/succinic acid, histidine, Sodium benzoate/benzoic acid, and sodium phosphates, and Tris(hydroxymethyl)aminomethane. A form of repository or "depot" slow release preparation can be used, in some embodiments, so that therapeutically effective amounts of the preparation are delivered into the bloodstream over many hours or days following parenteral injection or delivery.

The pharmaceutical compositions comprising amylin or amylin analogs suitable for injectable use include sterile aqueous solutions or dispersions and sterile powders for the extemporaneous preparation of sterile injectable solutions or dispersions. In all cases, the form should be sterile and should be fluid that is easily syringable. It is also desirable for the compositions comprising amylin or amylin analogs to be stable under the conditions of manufacture and storage and must be preserved against the contaminating action of microorganisms, such as bacteria and fungi. The carrier can be a solvent or dispersion medium containing, for example, water, ethanol, polyol (e.g., sorbitol, glycerol, propylene glycol, and liquid polyethylene glycol, and the like), dimethylacetamide, cremorphor EL, suitable mixtures thereof, and oils (e.g., soybean, sesame, castor, cottonseed, ethyl oleate, isopropyl myristate, glycofurol, corn). The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, meta-cresol, benzyl alcohol, parabens (methyl, propyl, butyl), chlorobutanol, phenol, phenylmercuric salts (acetate, borate, nitrate), sorbic acid, thimerosal, and the like. In many cases, it will be preferable to include tonicity agents (for example, sugars, sodium chloride). Prolonged absorption of the injectable compositions can be brought about by the use in the compositions of agents delaying absorption (for example, aluminum monostearate and gelatin). An exemplary pharmaceutical composition can be 0.1 to 5% of the amylin or amylin analog in an aqueous system along with approximately 0.02 to about 0.5% (w/v) of an acetate, phosphate, citrate, or glutamate buffer to a pH of the final composition of approximately 3.0 to about 6.0 as well as approximately 1.0 to 10% (w/v) of a carbohydrate or polyhydric alcohol tonicifier; and, optionally, approximately 0.005 to 1.0% (w/v) of a preservative selected from the group consisting of m-cresol, benzyl alcohol, parabens and phenol.

In some embodiments, sterile injectable solutions comprising amylin or amylin analogs can be prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and the required other ingredients from those enumerated above. In the case of sterile powders for the preparation of sterile injectable solutions, the preferred methods of preparation are vacuum-drying and freeze-drying techniques that yield a powder of the active ingredient plus any additional desired ingredient from a previously sterile-filtered solution thereof.

Generally, a therapeutically or prophylactically effective amount of the pharmaceutical compositions comprising amylin or amylin analogs described herein will be determined by the age, weight, and condition or severity of the Aβ deposition or plaques of the subject, which can be determined, for example, using the methods described herein. See, e.g., Remington's Pharmaceutical Sciences 697-773. See also Wang and Hanson, Parenteral Formulations of Proteins and Peptides: Stability and Stabilizers, Journal of Parenteral Science and Technology, Technical Report No. 10, Supp. 42:2 S (1988). Typically, a dosage of between about 0.001 µg/kg body weight/day to about 1000 µg/kg body weight/day, can be used, but more or less, as a skilled practitioner will recognize, can be used. Dosing can be one or more times daily, or less frequently, and can be in conjunction with other compositions as described herein. It should be noted that the compositions and methods described herein are not limited to the dosages recited herein. The final dosage regimen will be determined by the attending physician, considering factors that modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment using the amylin or amylin analogs described herein for the reduction or inhibition of Aβ deposition or plaque formation in the brain.

An effective dose will typically be in the range of about 1 to 30 µg to about 5 mg/day, preferably about 10 to 30 µg to about 2 mg/day and more preferably about 5 to 100 µg to about 1 mg/day, most preferably about 5 µg to about 500 µg/day, administered in a single or divided doses. The dosages can be between about 0.01 to about 500 µg/dose. It is contemplated that the amylin or amylin analog compounds described herein can be administered 1, 2, 3, 4 or more times a day. Accordingly, exemplary doses can be derived from the total amount of drug to be given a day and the number doses administered a day. For example, exemplary doses can range from about 0.125 µg/dose (0.5 µg given four times a day) to about 5 mg/dose (5 mg given once a day). Other dosages can be between about 0.01 to about 100 µg/kg/dose. Still other exemplary doses may be 20, 30, 40, 50, 60, 70, 80, 90, 100, 110, 120, 130, 140, 150, 160, 170, 180, 190, or 200 µg/dose. The exact dose to be administered can be determined by one of skill in the art and is dependent upon the potency of the particular compound, as well as upon the age, weight and condition of the individual. Administration should begin whenever the reduction or inhibit of Aβ deposition or plaque formation in the brains desired, for example, at the first sign of symptoms or shortly after diagnosis of Alzheimer's disease or amnestic MCI. Administration can be by any route, e.g., injection, preferably subcutaneous, intravenous or intramuscular, etc. Dosages for certain routes can be increased to account for decreased bioavailablity, for example, by about 5-100 fold.

In some embodiments, where the pharmaceutical composition comprising amylin or an amylin analog is to be administered parenterally, the composition is formulated so as to deliver a dose of the compounds ranging from 0.1 µg/kg to 100 mg/kg body weight/day, preferably at doses ranging from 10 µg/kg to about 50 mg/kg body weight/day. Parenteral administration can be carried out with an initial bolus followed by continuous infusion to maintain therapeutic circulating levels of drug product. Those of ordinary skill in the art can readily optimize effective dosages and administration regimens as determined by good medical practice and the clinical condition of the individual patient.

The frequency of dosing will depend on the pharmacokinetic parameters of the amylin or amylin analog compositions and the therapeutic results achieved. In some embodiments, an effective dose of a treatment can be administered to a subject once. In some embodiments of the methods described herein, an effective dose of a treatment can be administered to a subject repeatedly. A treatment can be administered over a period of time, such as over a 5 minute, 10 minute, 15 minute, 20 minute, or 25 minute period. The administration can be repeated, for example, on a regular basis, such as hourly for 3 hours, 6 hours, 12 hours or longer or such as biweekly (i.e., every two weeks) for one month, two months, three months, four months or longer. In some embodiments of the methods described herein, administration can be chronic, e.g., one or more doses and/or treatments daily over a period of weeks or months. In some embodiments of these methods and all such methods described herein, the administering is at least once a week.

In some embodiments of these methods and all such methods described herein, the administering is at least twice a week. In some embodiments of these methods and all such methods described herein, the administering is at least three times a week. In some embodiments of these methods and all such methods described herein, the administering is at least four times a week. In some embodiments of these methods and all such methods described herein, the administering is daily.

Examples of dosing and/or treatment schedules are administration daily, twice daily, three times daily or four or more times daily over a period of once a week, twice a week, three times a week, four times a week, five times a week, 2 weeks, 3 weeks, 4 weeks, 1 month, 2 months, 3 months, 4 months, 5 months, or 6 months, or more. In some embodiments of the methods described herein, after an initial treatment regimen, e.g., daily for a month, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. by at least 10%, at least 15%, at least 20%, at least 25%, at least 30%, at least 40%, at least 50%, at least 60%, at least 70%, at least 80% or at least 90% or more.

As shown herein using mouse models, daily dosing of amyline or the amylin analog pramlintide increased memory functions. Thus, in some embodiments of the apsects described herein, the frequency of dosing is daily.

Also provided herein, in some aspects, are unit dose compositions comprising amylin or amylin analogs for the reduction and or inhibition of Aβ deposition or plaques in the brain and/or inhibiting or slowing the progression of disorders mediated by Aβ deposition, such as Alzheimer's disease. The term "unit dose," as used herein, when used in reference to a therapeutic composition, refers to physically discrete units suitable as unitary dosage for the subject, each unit containing a predetermined quantity of active material, such as an amylin analog of any of SEQ ID NO: 3, SEQ ID NO: 4 or SEQ ID NOs: 13-44, calculated to produce the desired therapeutic effect in association with the required physiologically acceptable diluent, i.e., carrier, or vehicle. As described herein, the unit dose compositions are administered in a manner compatible with the dosage formulation, and in a therapeutically effective amount. The quantity to be administered and timing depends on the subject to be treated, capacity of the subject's system to utilize the active ingredient, i.e., the amylin peptide or amylin analog, and degree of therapeutic effect desired.

The success of treatment or therapy using the unit dose compositions comprising amylin or an amylin analog of any of SEQ ID NO: 3, SEQ ID NO: 4 or SEQ ID NOs: 13-44 can be evaluated by the ordinarily skilled clinician by monitoring one or more symptoms or markers of the disease or disorder being treated by administration of the compositions. As used herein, "effective treatment" includes any statistically significant improvement in one or more indicia of the disease or disorder. Where appropriate, a clinically accepted grade or scaling system for the given disease or disorder can be applied, with an improvement in the scale or grade being indicative of effective treatment. For example, a dosage comprising a composition of the invention is considered to be pharmaceutically effective if the dosage reduce degree of neurodegeneration, e.g., indicated by changes in neurodegenerative morphologies or improvement in brain or cognitive function, by at least about 5%, at least about 10%, at least about 15%, at least about 20%, at least about 30%, at least about 40%, or at least about 50%. In one embodiment, the brain or cognitive function is improved by more than 50%, e.g., at least about 60%, or at least about 70%. In another embodiment, the brain or cognitive function is improved by at least about 80%, at least about 90% or greater, as compared to a control (e.g. in the absence of the composition described herein).

Depending upon the therapeutic agent and formulation of the unit dose compositions, effective dosages of unit dose compositions comprising amylin or an amylin analog can include, for example, 1 ng/kg of body weight up to a gram or more per kg of body weight and any amount in between. Preferred amounts, include, for example, unit dose ranges from about 0.03 mg per kg of body weight to about 0.0625 mg per kg of body weight; unit dose ranges from about 0.05 mg per kg of body weight to about 0.2 mg per kg of body weight; unit dose ranges from about 0.1 mg per kg of body weight to about 0.4 mg per kg of body weight; unit dose ranges from about 0.3 mg per kg of body weight to about 1.0 mg per kg of body weight; unit dose ranges from about 0.9 mg per kg of body weight to about 1.6 mg per kg of body weight; unit dose ranges from about 1.5 mg per kg of body weight to about 2.0 mg per kg of body weight; unit dose ranges from about 1.8 mg per kg of body weight to about 3.2 mg per kg of body weight; unit dose ranges from about 3.0 mg per kg of body weight to about 6.5 mg per kg of body weight; unit dose ranges from about 5.5 mg per kg of body weight to about 10 mg per kg of body weight; unit dose ranges from about 8.0 mg per kg of body weight to about 20 mg per kg of body weight, unit dose ranges from about 20.0 mg per kg of body weight to about 50 mg per kg of body weight; or any amount in between.

Dosages in such ranges can be administered once, twice, three times, four times or more per day, or every two days, every three days, every four days, once a week, twice a month, once a month or less frequently over a duration of days, weeks or months, depending on the condition being treated—where the therapeutic approach treats or ameliorates but does not permanently cure the disease or disorder, e.g., as described herein, where the amylin or an amylin analog effects reduction or inhibition of Aβ deposition or Aβ plaque formation in the brain and consequent improvement in memory capacities after repeated administration, the unit dose compositions comprising amylin or an amylin analog can be repeated over time as needed. In some embodiments of the aspects described herein, sustained release formulations of unit dose compositions comprising amylin or an amylin analog are specifically contemplated herein. In some embodiments of the aspects described herein, continuous, relatively low doses are contemplated after an initial higher therapeutic dose.

A unit dose composition comprising comprising amylin or an amylin analog of any of SEQ ID NO: 3, SEQ ID NO: 4 or SEQ ID NOs: 13-44 as described herein can be delivered to or administered to a subject by subcutaneous or intravenous injection, in some embodiments. A unit dose composition comprising amylin or an amylin analog can be incorporated into pharmaceutical compositions suitable for subcutaneous or intravenous, in some embodiments. For example, unit dose compositions can include one or more amylin analogs and a pharmaceutically acceptable carrier, in some embodiments. Supplementary active compounds, such as targeting moieties, can also be incorporated into the unit dose compositions, as described herein. Unit dose compositions for administration of amylin or an amylin analog can include, in some embodiments, sterile aqueous solutions that can also contain buffers, diluents and other suitable additives.

In some embodiments, the effective dose of amylin or an amylin analog can be administered in a single dose or in two or more doses, as desired or considered appropriate under the specific circumstances. For example, as described herein, daily administration of the amylin analog pramlintide in mice led to cognitive improvements.

In some embodiments, the effective dose of amylin or an amylin analog can be administered as two or more separate unit dosages and administered simultaneously into at least two different locations. In some embodiments, the effective dose of amylin or an amylin analog can be administered as two or more separate unit dosages and administered sequentially into the same or different locations.

In some embodiments, if desired to facilitate repeated or frequent infusions, a non-implantable delivery device, e.g., needle, syringe, pen device, or implantable delivery device, e.g., a pump, semi-permanent stent, or reservoir can be advisable. In some such embodiments, the delivery device can include a mechanism to dispense a unit dose of the pharmaceutical composition comprising amylin or an amylin analog. In some embodiments, the device releases the pharmaceutical composition comprising amylin or an amylin analog continuously, e.g., by diffusion. In some embodiments, the device can include a sensor that monitors a parameter within a subject, such as the level of blood Aβ. For example, the device can include pump, e.g., and, optionally, associated electronics.

A unit dose composition comprising amylin or an amylin analog can be modified, in some embodiments, such that it is capable of traversing the blood brain barrier. For example, amylin or an amylin analog can be conjugated to a molecule that enables the agent to traverse the barrier. Such conjugated amylin or amylin analog can be administered by subcutaneous injection, for example.

A unit dose composition comprising amylin or an amylin analog described herein can also be delivered through the use of implanted, indwelling catheters that provide a means for injecting small volumes of fluid containing amylin or the amylin analogs described herein directly into the body. The proximal end of these catheters can be connected to an implanted, access port surgically affixed to the patient's body.

Alternatively, implantable delivery devices, such as an implantable pump can be employed. The delivery of the unit dose compositions comprising amylin or an amylin analog as described herein can be accomplished with a wide variety of devices, including but not limited to U.S. Pat. Nos. 5,735,814, 5,814,014, and 6,042,579, all of which are incorporated herein by reference. Using the teachings described herein, those of skill in the art will recognize that these and other devices and systems can be suitable for delivery of unit dose compositions comprising amylin or an amylin analog described herein.

In some such embodiments, the delivery system further comprises implanting a pump outside the body, the pump coupled to a proximal end of the catheter, and operating the pump to deliver the predetermined dosage of a unit dose composition comprising amylin or an amylin analog described herein through the discharge portion of the catheter. A further embodiment comprises periodically refreshing a supply of the unit dose composition comprising amylin or an amylin analog to the pump outside the body.

Intramuscular or subcutaneous administration of a unit dose composition comprising amylin or an amylin analog can be provided by the subject or by another person, e.g., a another caregiver. A caregiver can be any entity involved with providing care to the human: for example, a hospital, hospice, doctor's office, outpatient clinic; a healthcare worker such as a doctor, nurse, or other practitioner; or a spouse or guardian, such as a parent.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable or unacceptable physiological effects such as toxicity, nausea, dizziness, gastric upset, immune reaction and the like. A pharmaceutically acceptable carrier will not promote the raising of an immune response to an agent with which it is admixed, unless so desired.

The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline Saline-based carriers are most useful for the administration of cells or cell preparations. Still further, aqueous carriers can contain more than one buffer salt, as well as salts such as sodium and potassium chlorides, dextrose, polyethylene glycol and other solutes.

Dosage and administration of therapeutic compositions comprising, for example, amylin or an amylin agonist, described herein vary with the subject to be treated and the therapeutic approach taken in a given instance. The success of a treatment can be evaluated by the ordinarily skilled clinician by monitoring one or more symptoms of the subject being administered the amylin or amylin analog. Effective treatment includes any statistically significant improvement in one or more indicia of the disease. Where appropriate, a clinically accepted grade or scaling system for the given disease or disorder can be applied, with an improvement in the scale or grade being indicative of effective treatment. Depending upon the therapeutic composition, various subject parameters, and the mode of delivery, effective dosages can include, for example, 1 ng/kg of body weight up to a gram or more per kg of body weight and any amount in between. Preferred amounts can be, for example, in the range of 5 µg/kg body weight to 500 mg/kg of body weight or any amount in between. Dosages in such ranges can be administered once, twice, three times, four times or more per day, or every two days, every three days, every four days, once a week, twice a month, once a month or less frequently over a duration of days, weeks or months, as determined by a clinician. Sustained release formulations of the therapeutic compositions comprising amylin or an amylin agonist, are also specifically contemplated herein. Continuous, relatively low doses are also contemplated after an initial higher therapeutic dose.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. Exemplary modes of administration of the therapeutic compositions comprising amylin or an amylin agonist, described herein, include, but are not limited to, injection, infusion, inhalation (e.g., intranasal or intratracheal), ingestion, rectal, and topical (including buccal and sublingual) administration. The phrases "parenteral administration" and "administered parenterally" as used herein, refer to modes of administration other than enteral and topical administration, usually by injection. As used herein, "injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebrospinal, and intrasternal injection and infusion. The phrases "systemic administration," "administered systemically", "peripheral administration" and "administered peripherally" as used herein refer to administration of a therapeutic composition other than directly into a target site, tissue, or organ, such as the lung, such that it enters the subject's circulatory system and, thus, is subject to metabolism and other like processes.

Suitable regimes for initial administration and further doses or for sequential administrations can be varied. In some embodiments, a therapeutic regimen includes an initial administration, for example, an amyline challenge using the methods and assays described herein, followed by subsequent administrations, if necessary. In some embodiments, multiple administrations of an amylin agonist agent can be administered to the subject. For example, the amylin agonist agent can be administered in two or more, three or more, four or more, five or more, or six or more injections. In some embodiments, the same amylin agonist agent can be administered in each subsequent administration. In some embodiments, a different amylin agonist agent described herein can be administered in each subsequent administration.

The terms "treatment" and "treating" as used herein, with respect to treatment of a disease, means preventing the progression of the disease, or altering the course of the disorder (for example, but are not limited to, slowing the progression of the disorder), or reversing a symptom of the disorder or reducing one or more symptoms and/or one or more biochemical markers in a subject, preventing one or more symptoms from worsening or progressing, promoting recovery or improving prognosis. For example, in the case of treating a disorder mediated by Aβ plaque disposition in the brain, e.g., AD, therapeutic treatment refers to reduced neurodegenerative morphologies and/or the alleviation of at least one symptom associated with a neurodegenerative disease, e.g., AD. Measurable lessening includes any statistically significant decline in a measurable marker or symptom, such as assessing the cognitive improvement with neuropsychological tests such as verbal and perception after treatment. In some embodiments of these aspects and all such aspects described herein, at least one symptom of a neurodegenerative disorder, e.g., AD, is alleviated by at least about 10%, at least about 15%, at least about 20%, at least about 30%, at least about 40%, or at least about 50%. In other embodiments, at least one symptom is alleviated by more than 50%, e.g., at least about 60%, or at least about 70%. In other embodiments, at least one symptom is alleviated by at least about 80%, at least about 90% or greater, as compared to a control (e.g. in the absence of the composition or method of treatment described herein).

In some embodiments, the method of treatment further comprises a step of diagnosing a subject with AD prior to the contacting. Subjects amenable to methods of treatment are subjects that have been diagnosed with Alzheimer's disease. Cognitive methods for diagnosing Alzheimer's disease are well known in the art. For example, the stage of Alzheimer's disease can be assessed using the Functional Assessment Staging (FAST) scale, which divides the progression of Alzheimer's disease into 16 successive stages under 7 major headings of functional abilities and losses: Stage 1 is defined as a normal adult with no decline in function or memory. Stage 2 is defined as a normal older adult who has some personal awareness of functional decline, typically complaining of memory deficit and forgetting the names of familiar people and places. Stage 3 (early Alzheimer's disease) manifests symptoms in demanding job situation, and is characterized by disorientation when traveling to an unfamiliar location; reports by colleagues of decreased performance; name- and word-finding deficits; reduced ability to recall information from a passage in a book or to remember a name of a person newly introduced to them; misplacing of valuable objects; decreased concentration. In stage 4 (mild Alzheimer's Disease), the patient may require assistance in complicated tasks such as planning a party or handling finances, exhibits problems remembering life events, and has difficulty concentrating and traveling. In stage 5 (moderate Alzheimer's disease), the patient requires assistance to perform everyday tasks such as choosing proper attire. Disorientation in time, and inability to recall important information of their current lives, occur, but patient can still remember major information about themselves, their family and others. In stage 6 (moderately severe Alzheimer's disease), the patient begins to forget significant amounts of information about themselves and their surroundings and require assistance dressing, bathing, and toileting. Urinary incontinence and disturbed patterns of sleep occur. Personality and emotional changes become quite apparent, and cognitive abulia is observed. In stage 7 (severe Alzheimer's disease), speech ability becomes limited to just a few words and intelligible vocabulary may be limited to a single word. A patient can lose the ability to walk, sit up, or smile, and eventually cannot hold up the head.

Other alternative diagnostic methods for AD include, but not limited to, cellular and molecular testing methods disclosed in U.S. Pat. Nos. 7,771,937, 7,595,167, 5,558,0748, and PCT Application No.: WO2009/009457, the content of which is incorporated by reference in its entirety. Additionally, protein-based biomarkers for AD, some of which can be detected by non-invasive imaging, e.g., PET, are disclosed in U.S. Pat. No. 7,794,948, the content of which is incorporated by reference in its entirety.

Genes involved in AD risk can be used for diagnosis of or high predisposition for AD. One example of other AD risk genes is apolipoprotein E-4 (APOE-4). APOE-4 is one of three common forms, or alleles, of the APOE gene; the others are APOE-e2 and APOE-e3. APOE provides the blueprint for one of the proteins that carries cholesterol in the bloodstream. Everyone inherits a copy of some form of APOE from each parent. Those who inherit one copy of APOE-4 have an increased risk of developing AD. Those who inherit two copies have an even higher risk, but not a certainty of developing AD. In addition to raising risk, APOE-4 may tend to make symptoms appear at a younger age than usual. Other AD risk genes in addition to APOE-e4 are known in the art. Some of them are disclosed in US Pat. App. Nos.:US 2010/0249107, US 2008/0318220, US 2003/0170678 and PCT Application No.: WO 2010/048497, the content of which is incorporated by reference in its entirety. Genetic tests are well established in the art and are available, for example for APOE-e4. A subject carrying the APOE-4 allele can, therefore, be identified as a subject at risk of developing AD.

In some embodiments of the compositions, methods, and assays described herein, other subjects with Aβ plaque deposition or burden are amenable to the methods described herein. Such subjects include, but not limited to, subjects with Down syndrome, Huntington disease, the unaffected carriers of APP or presenting gene mutations, and the late onset AD risk factor, apolipoprotein E-4.

In some embodiments of the compositions, methods, and assays described herein, AD patients that are currently receiving other AD therapeutic treatment can also be subjected to the methods of treatment as described herein.

In some embodiments, a subject who has been diagnosed with an increased risk for developing AD, e.g., using the diagnostic methods and assays described herein or any AD diagnostic methods known in the art, can be subjected to the methods of treatment as described herein.

In some embodiments, the subject selected for the methods described herein can be previously diagnosed with AD and is being under a treatment regimen. Several prescription drugs are currently approved by the U.S. Food and Drug Administration (FDA) to treat people who have been diagnosed with Alzheimer's disease. It is important to understand that none of these medications stops the disease itself, as noted by the National Institute of Health's (NIH) website on the worldwide web.

Medications called cholinesterase inhibitors are prescribed for mild to moderate Alzheimer's disease. These drugs can help delay or prevent symptoms from becoming worse for a limited time and can help control some behavioral symptoms. Cholinesterase inhibitors are prescribed to treat symptoms related to memory, thinking, language, judgment and other thought processes. Cholinesterase inhibitors prevent the breakdown of acetylcholine, a chemical messenger important for learning and memory. This supports communication among nerve cells by keeping acetylcholine levels high. Cholinesterase inhibitors have been shown to delay worsening of symptoms for 6 to 12 months, on average, for about half the people who take them. Cholinesterase inhibitors are generally well tolerated, and if side effects occur, they commonly include nausea, vomiting, loss of appetite and increased frequency of bowel movements.

Cholinesterase inhibitors include: RAZADYNE® (galantamine), EXELON® (rivastigmine), and ARICEPT® (donepezil). Another drug, COGNEX® (tacrine), was the first approved cholinesterase inhibitor but is rarely prescribed today due to safety concerns (Cutler and Sramek, N. Engl. J. Med. 328:808 810, 1993). Donepezil (ARICEPT®) is the only cholinesterase inhibitor approved to treat all stages of Alzheimer's disease, including moderate to severe. Scientists do not yet fully understand how cholinesterase inhibitors work to treat Alzheimer's disease, but, without wishing to be bound or limited by theory, research indicates that they prevent the breakdown of acetylcholine, a brain chemical believed to be important for memory and thinking. As Alzheimer's progresses, the brain produces less and less acetylcholine; therefore, cholinesterase inhibitors can eventually lose their effect.

A medication known as NAMENDA® (memantine), an N-methyl D-aspartate (NMDA) antagonist, is prescribed to treat moderate to severe Alzheimer's disease. This drug's main effect is to delay progression of some of the symptoms of moderate to severe Alzheimer's. It can allow patients to maintain certain daily functions a little longer than they would without the medication. For example, NAMENDA® can help a patient in the later stages of the disease maintain his or her ability to use the bathroom independently for several more months, a benefit for both patients and caregivers. Without wishing to be bound or limited by theory, NAMENDA® is believed to work by regulating glutamate, an important brain chemical. When produced in excessive amounts, glutamate can lead to brain cell death. Because NMDA antagonists work very differently from cholinesterase inhibitors, the two types of drugs can be administered in combination, in some embodiments of the methods described herein. Memantine is prescribed to improve memory, attention, reason, language and the ability to perform simple tasks. It can be used alone or with other Alzheimer's disease treatments. There is some evidence that individuals with moderate to severe Alzheimer's who are taking a cholinesterase inhibitor can benefit by also taking memantine. Memantine can cause side effects, including headache, constipation, confusion and dizziness.

In addition, recent work has indicated that Alzheimer's patients can benefit from increased audio and visual stimuli.

Doctors usually start patients at low drug doses and gradually increase the dosage based on how well a patient tolerates the drug. There is some evidence that certain patients can benefit from higher doses of the cholinesterase inhibitors.

Assays and Methods for Detecting Increased Aβ Peptide and Alzheimer's Disease

Until the discovery by the inventors of the assays and methods described herein, determination and diagnosis of amyloid associated diseases, such as Alzheimer's disease, has had little success, and has required complicated, expensive, and/or invasive tools and methods. In contrast, the assays and methods described herein are minimally invasive, inexpensive, and require only a simple blood test, similar to glucose monitoring in pre-diabetic and diabetic patients. Early, non-invasive, and accurate methods and assays for diagnosis are beneficial for several reasons. Beginning treatment early on in the disease process can help preserve function for some time, even though, to date, the underlying Alzheimer's process cannot be changed. In addition, having an early diagnosis helps people with Alzheimer's and their families plan for the future, make living arrangements, take care of financial and legal matters, and develop support networks.

It has proven extremely difficult to diagnose Alzheimer's disease before death, much less to develop drug therapies, or to treat AD. For example, screening for apolipoprotein E genotype has been suggested as an aid in the diagnosis of AD. Difficulties arise with this technology, however, because the apolipoprotein E4 allele is only a risk factor for AD, not a disease marker. It is absent in many AD patients and present in many non-demented elderly people. Immunoassay methods have been developed for detecting the presence of neurochemical markers in AD patients and to detect an AD-related amyloid protein in cerebral spinal fluid. These methods for diagnosing AD have not been proven to detect AD in all patients, particularly at early stages of the disease Unlike the methods and assays described herein, they are also relatively invasive, requiring a spinal tap. Recently, radiolabeled Aβ peptide has been used to try and label diffuse, compact and neuritic type plaques in sections of AD brain. These peptides, however, do not normally cross the blood-brain barrier in amounts necessary for imaging. Congo red can be used for diagnosing amyloidosis in vivo in non-brain parenchymal tissues. But Congo red is not suitable for in vivo diagnosis of Aβ deposits in brain because only very small amounts, approximately 0.03% of an injected dose of iodinated Congo red, can enter the brain parenchyma. Radioiodinated bisdiazobenzidine compounds related to Congo red, such as Benzo Orange R and Direct Blue 4, have also been proposed to be useful in vitro and in vivo to detect the presence and location of amyloid deposits in an organ of a patient. However, like Congo red, all of the compounds contain strongly acidic sulfonic acid groups which severely limit entry of these compounds into the brain. Imaging compounds, notably Pittsburgh Compound-B, (6-OH-BTA-1, a thioflavin), can selectively bind to Aβ in vitro and in vivo. This technique, combined with PET imaging, has been used to image areas of plaque deposits in Alzheimer's patients. Atomic force microscopy, which can visualize nanoscale molecular surfaces, can be used to determine the aggregation state of Amyloid beta in vitro, but is not useful in in vivo applications.

Attempts have also been made to develop monoclonal antibodies as probes for imaging of amyloid plaques. For instance, antibodies raised against the N-terminal region (1-28) of Aβ bind to in vitro-formed Aβ assemblies, leading to disaggregation of fibrils and partial restoration of Aβ solubility. Some of the monoclonal antibodies raised against soluble Aβ(1-28) have also been found to inhibit fibrillar aggregation of Aβ peptide in vitro. The success of these attempts, however, has been limited due to the difficulty of getting these large molecules across the blood-brain barrier. ELISA, which is an immunosorbent assay that utilizes a pair of antibodies that recognize Amyloid beta, can only be used on ex vivo samples, such as a spinal tap.

In contrast, the inventors have discovered that amylin or amylin analogs can be used in assays, in vitro and ex vivo methods, and kits for detecting the presence of plaques comprising Aβ peptide in the brain, and for identifying individuals at increased risk for Alzheimer's disease (AD) and/or amnestic mild cognitive impairment. The inventors discovered that there is a significant positive correlation between the concentrations of amylin and Aβ1-40 or Aβ1-42 in plasma samples from human subjects with AD or amnestic MCI, but not in control subjects. As demonstrated herein, the inventors showed that intraperitoneal or subcutaneous injection of amylin or an amylin analog in mice and humans, respectively, results in increased blood levels of Aβ peptide in subjects with Alzheimer's disease. Until the discoveries by the inventors described herein, determination and diagnosis of amyloid associated diseases, such as Alzheimer's disease, has had little success, and has required complicated, expensive, and/or invasive tools and methods. In contrast to the standard of care determination and diagnosis of amyloid associated diseases, such as Alzheimer's disease, the assays and methods described herein are non-invasive, inexpensive, and require only an amylin or amylin analog challenge as part of a simple blood test or assay.

Accordingly, in some aspects, provided herein are assays for selecting a therapy for a subject having or at risk for Aβ peptide deposition in the brain, the assay comprising:

subjecting a biological sample, obtained from a subject administered an amylin or amylin analog challenge within 72 hours prior to collection of the biological sample, to an assay that determines the amount of Aβ peptide in the biological sample;

determining the amount of Aβ peptide in the biological sample; and selecting an amylin or amylin analog therapy for the subject when the determined amount of Aβ peptide in the biological sample is increased relative to a reference value; or not selecting an amylin or amylin analog therapy for the subject when the determined amount of Aβ peptide in the biological sample is below a reference value.

In some embodiments of these assays and all such assays described herein, the assay further comprises, when the determined amount of Aβ peptide in the biological sample is increased relative to a reference value, the step of treating the subject with amylin or an amylin analog therapy. In some embodiments of these assays, the treating is at least once a week. In some embodiments of these assays, the treating is at least twice a week. In some embodiments of these assays, the treating is at least three times a week. In some embodiments of these assays, the treating is at least four times a week. In some embodiments of these assays, the treating is daily.

In some embodiments of these assays and all such assays described herein, the biological sample is obtained from the subject within 24 hours of administration to the subject of the amylin or amylin analog challenge.

In some embodiments of these assays and all such assays described herein, the biological sample is obtained from the subject within 4 hours of administration to the subject of the amylin or amylin analog challenge.

In some embodiments of these assays and all such assays described herein, the biological sample is a blood sample, a serum sample, or a plasma sample.

In some embodiments of these assays and all such assays described herein, the Aβ peptide is Aβ42 of SEQ ID NO: 2.

In some embodiments of these assays and all such assays described herein, the amylin or amylin analog administered to the subject prior to the collection of the biological sample comprises a sequence of SEQ ID NO: 3, SEQ ID NO: 4, or SEQ ID NOs: 13-44.

In some embodiments of these assays and all such assays described herein, the subject having or at risk for Aβ peptide deposition in the brain has or is at risk for Alzheimer's disease or amnestic mild cognitive impairment (aMCI).

In some embodiments of these assays and all such assays described herein, the determined amount of Aβ peptide in the biological sample is increased by at least one standard deviation above the reference value.

In some embodiments of these assays and all such assays described herein, the determined amount of Aβ peptide in the biological sample is increased by at least two standard deviations above the reference value.

Also provided herein, in some aspects, are methods for selecting a therapy for a subject having or at risk for Aβ peptide deposition in the brain, the method comprising:
  a. subjecting a biological sample, obtained from a subject administered an amylin or amylin analog challenge within 72 hours prior to collection of the biological sample, to an assay or method that determines the amount of Aβ peptide in the biological sample;
  b. determining the amount of Aβ peptide in the biological sample; and
  c. selecting an amylin or amylin analog therapy for the subject when the determined amount of Aβ peptide in the biological sample is increased relative to a reference value; or not selecting an amylin or amylin analog therapy for the subject when the determined amount of Aβ peptide in the biological sample is below a reference value.

In some embodiments of these methods and all such methods described herein, the determined amount of Aβ peptide in the biological sample is increased by at least one standard deviation above the reference value.

In some embodiments of these methods and all such methods described herein, the determined amount of Aβ peptide in the biological sample is increased by at least two standard deviations above the reference value.

In some embodiments of these methods and all such methods described herein, the method further comprises, when the determined amount of Aβ peptide in the biological sample is increased relative to a reference value, the step of treating the subject with amylin or an amylin analog therapy. In some embodiments of these methods, the treating is at least once a week. In some embodiments of these methods, the treating is at least twice a week. In some embodiments of these methods, the treating is at least three times a week. In some embodiments of these methods, the treating is at least four times a week. In some embodiments of these methods, the treating is daily.

In some embodiments of these methods and all such methods described herein, the biological sample is obtained from the subject within 24 hours of administration to the subject of the amylin or amylin analog challenge.

In some embodiments of these methods and all such methods described herein, the biological sample is obtained from the subject within 4 hours of administration to the subject of the amylin or amylin analog challenge.

In some embodiments of these methods and all such methods described herein, the biological sample is a blood sample, a serum sample, or a plasma sample.

In some embodiments of these methods and all such methods described herein, the Aβ peptide is Aβ42 of SEQ ID NO: 2.

In some embodiments of these methods and all such methods described herein, the amylin or amylin analog administered to the subject prior to the collection of the biological sample comprises a sequence of SEQ ID NO: 3, SEQ ID NO: 4, or SEQ ID NOs: 13-44.

In some embodiments of these methods and all such methods described herein, the subject having or at risk for Aβ peptide deposition in the brain has or is at risk for Alzheimer's disease or amnestic mild cognitive impairment (aMCI).

In some aspects, provided herein are assays comprising: measuring or quantifying the amount of Aβ peptide in a biological sample obtained from a subject administered an amylin or amylin analog challenge within 72 hours prior to collection of the biological sample; and comparing the measured or quantified amount of Aβ peptide with a reference value, and if the amount of Aβ peptide is increased relative to the reference value, identifying the subject as having increased Aβ peptide.

In some aspects, provided herein are assays comprising: measuring or quantifying the amount of Aβ peptide in a first biological sample obtained from a subject prior to administration of an amylin or amylin analog challenge to the subject; measuring or quantifying the amount of Aβ peptide in a second biological sample obtained from the subject within 72 hours of administration of an amylin or amylin analog challenge; comparing the measured or quantified amount of Aβ peptide in the second biological sample to the first biological sample, and if the amount of Aβ peptide in the second biological sample is increased relative to the first biological sample, identifying the subject as having increased Aβ peptide.

In other aspects, provided herein are assays for Alzheimer's disease or amnestic mild cognitive impairment comprising: measuring or quantifying the amount of Aβ peptide in a biological sample obtained from a subject administered an amylin or amylin analog challenge within 72 hours prior to collection of the biological sample; and comparing the measured or quantified amount of Aβ peptide with a reference value, and if the amount of Aβ peptide is increased relative to the reference value, identifying the subject as having Alzheimer's disease or amnestic mild cognitive impairment.

In some aspects, provided herein are assays for Alzheimer's disease or amnestic mild cognitive impairment comprising: measuring or quantifying the amount of Aβ peptide in a first biological sample obtained from a subject prior to administration of an amylin or amylin analog challenge to the subject; measuring or quantifying the amount of Aβ peptide in a second biological sample obtained from the subject within 72 hours of administration of an amylin or amylin analog challenge; comparing the measured or quantified amount of Aβ peptide in the second biological sample to the first biological sample, and if the amount of Aβ peptide in the second biological sample is increased relative to the first biological sample, identifying the subject as having Alzheimer's disease or amnestic mild cognitive impairment.

Also provided herein, in other aspects, are assays for detecting the presence of plaques comprising Aβ peptide in a subject comprising: measuring or quantifying the amount of Aβ peptide in a biological sample obtained from a subject administered an amylin or amylin analog challenge within 72 hours prior to collection of the biological sample; and comparing the measured or quantified amount of Aβ peptide with a reference value, and if the amount of Aβ peptide is increased relative to the reference value, identifying the subject as having plaques comprising Aβ peptide.

In some aspects, provided herein are assays for detecting the presence of plaques comprising Aβ peptide in a subject comprising: measuring or quantifying the amount of Aβ peptide in a first biological sample obtained from a subject prior to administration of an amylin or amylin analog challenge to the subject; measuring or quantifying the amount of Aβ peptide in a second biological sample obtained from the subject within 72 hours of administration of an amylin or amylin analog challenge; comparing the measured or quantified amount of Aβ peptide in the second biological sample to the first biological sample, and if the amount of Aβ peptide in the second biological sample is increased relative to the first biological sample, identifying the subject as having plaques comprising Aβ peptide.

In some embodiments of these assays and all such assays described herein, the biological sample is a blood sample, a serum sample, plasma sample, or other biological sample.

In some embodiments of these assays and all such assays described herein, the amylin or amylin analog administered to the subject comprises a sequence of SEQ ID NO: 3, SEQ ID NO: 4, or SEQ ID NOs: 13-44.

As used herein, "an amylin or amylin analog challenge" refers to administration of a dose of amylin or an amylin analog to a subject in an amount sufficient to measure or quantify a subject's response to the amylin via measurement or quantification of Aβ peptide in a biological sample obtained from the subject. Because amylin or amylin analogs can traverse the blood brain barrier, as demonstrated herein, amylin or an amylin analog challenge in a subject leads to transient increases or surges in the level of Aβ peptide in the blood of the subject, if the subject has plaques comprising Aβ peptide in the brain, or has Alzheimer's disease or amnestic MCI. The dose use in an amylin or amylin analog challenge can, in different embodiments, be less than, equivalent to, or greater than that found in a therapeutically effective dose of amylin or an amylin analog used in the methods described herein. In some embodiments of the aspects described herein, as part of "an amylin or amylin analog challenge," a biological sample, such as, for example, a blood, serum, or plasma, is obtained from the subject within 96 hours following the challenge. Preferably a biological sample is obtained from the subject within 96 hours, within 84 hours, within, 72 hours, within 60 hours, within 48 hours, within 36 hours, within 24 hours, within 23 hours, within 22 hours, within 21 hours, within 20 hours, within 19 hours, within 18 hours, within 17 hours, within 16 hours, within 15 hours, within 14 hours, within 12 hours, within 11 hours, within 10 hours, within 9 hours, within 8 hours, within 7 hours, within 6 hours, within 5 hours, within 4 hours, within 2 hours, within 1 hour following administration of the amylin or amylin analog challenge.

As used herein, "determining the amount of Aβ peptide," or "measuring or quantifying the amount of Aβ peptide," refers to any method or assay that can be used to obtain a qualitative or quantitative measurement of the expression of Aβ peptide in a biological sample obtained from a subject. Such measuring or quantifying can use, for example, protein based assays used to detect changes in expression of proteins, such as ELISA or Western Blot analyses using antibodies or antigen-binding fragments thereof specific for Aβ peptide, such as antibodies raised against the N-terminal region (1-28) of Aβ.

The term "expression" refers to the cellular processes involved in producing RNA and proteins and as appropriate, secreting proteins, including where applicable, but not limited to, for example, transcription, translation, folding, modification and processing. "Expression products" include RNA transcribed from a gene and polypeptides obtained by translation of mRNA transcribed from a gene, and such expression can be detected using methods known to one of skill in the art.

The terms "increased," "increase" or "enhance" in connection with the amount of Aβ peptide in a biological sample obtained from a subject following administration of amylin are all used herein to generally mean an increase by a statically significant amount. For the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference value or level, or at least about a 1.5-fold, at least about a 1.6-fold, at least about a 1.7-fold, at least about a 1.8-fold, at least about a 1.9-fold, at least about a 2-fold, at least about a 3-fold, or at least about a 4-fold, or at least about a 5-fold, at least about a 10-fold increase, any increase between 2-fold and 10-fold, at least about a 25-fold increase, or greater as compared to a reference level.

The amount or level of Aβ peptide in a biological sample can be determined by comparison to a suitable reference value that acts a standard of comparison. The reference level is obtained or measured in a reference biological sample, such as a reference sample obtained from an age-matched normal control (e.g., an age-matched subject not having Alzheimer's disease), or a reference sample from the same subject prior to administration of amylin or an amylin analog, for example, a "first biological sample." A "reference value" is thus, in some embodiments, a predetermined reference level, such as an average or median amount or level of Aβ peptide obtained from, for example, biological samples from a population of healthy subjects that are in the chronological age group matched with the chronological age of the tested subject. In some embodiments, the reference biological samples from which the reference value is obtained can also be gender matched. For example, as explained herein, the amount or level of Aβ peptide in a biological sample can be assessed relative to the amount or level of Aβ peptide in a biological sample from the same subject prior to administration of amylin, or from a sample from another subject or from a repository of normal subject samples known to not have Alzheimer's disease or amnestic MCI. Exemplary analytical methods for measuring or quantifying the amount or level of Aβ peptide in a biological sample are explained herein.

Similarly, the terms "decrease," "reduced," "reduction," or "decrease" in connection with with the amount of Aβ peptide in a biological sample are all used herein generally to refer to a decrease by a statistically significant amount. However, for avoidance of doubt, ""reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference sample), or any decrease between 10-100% as compared to a reference level.

The terms "subject," "patient," and "individual" are used interchangeably herein, and refer to an animal, for example a human. For treatment of those disease states which are specific for a specific animal such as a human subject, the term "subject" refers to that specific animal. The terms 'non-human animals' and 'non-human mammals' are used interchangeably herein, and include mammals such as rats, mice, rabbits, sheep, cats, dogs, cows, pigs, and non-human primates. In some embodiments of the aspects described herein, a subject refers to a human subject showing symptoms of Alzheimer's disease, having memory loss, showing cognitive decline, or a subject at increased risk for Alzheimer's disease, such as a subject having a family history of neurodegenerative diseases.

As used herein, the terms "biological sample" or "subject sample" or "sample" refer to a quantity of tissue or fluid, or a cell or population of cells obtained from a subject. In some embodiments, the biological sample is a blood sample, including, for example, a serum sample, or a plasma sample. Most often, the sample has been removed from a subject, but the term "biological sample" can also, in some embodiments, refer to cells or tissue quantity of tissue or fluid analyzed in vivo, i.e. without removal from the subject. A biological sample or tissue sample includes, but is not limited to, blood, plasma, serum, cerebrospinal fluid, lymph fluid, bone marrow, tumor biopsy, urine, stool, sputum, pleural fluid, nipple aspirates, lymph fluid, the external sections of the skin, lung tissue, adipose tissue, connective tissue, sub-epithelial tissue, epithelial tissue, liver tissue, kidney tissue, uterine tissue, respiratory tissues, breast tissue, gastrointestinal tissue, and genitourinary tract tissue, tears, saliva, milk, cells (including, but not limited to, blood cells), biopsies, scrapes (e.g., buccal scrapes), tumors, organs, and also samples of an in vitro cell culture constituent. Often, a "biological sample" can comprise cells from the subject, but the term can also refer to non-cellular biological material, such as non-cellular fractions of blood, saliva, or urine. In some embodiments of the assays and methods described herein, a biological sample can be obtained from a subject within 72 hours following administration of amylin to the subject and the sample stored or preserved until such time as the assays and methods described herein can be applied to the biological sample. In other words, in some embodiments, the collection of the biological sample and the assays and methods described herein can be separated in time and/or location.

Also provided herein, in some aspects, are assays comprising: administering an amylin or amylin analog challenge to a subject; obtaining a biological sample from the subject within 72 hours of the administration of the amylin or amylin analog challenge; measuring or quantifying the amount of Aβ peptide in the biological sample obtained from the subject administered the amylin or amylin analog challenge; and comparing the measured or quantified amount of Aβ peptide with a reference value, and if the amount of Aβ peptide is increased relative to the reference value, identifying the subject as having increased Aβ peptide.

In some aspects, provided herein are assays comprising: measuring or quantifying the amount of Aβ peptide in a first biological sample obtained from a subject prior to administration of an amylin or amylin analog challenge to the subject; administering an amylin or amylin analog challenge to the subject; measuring or quantifying the amount of Aβ peptide in a second biological sample obtained from the subject within 72 hours of the administration of the amylin or amylin analog challenge; comparing the measured or quantified amount of Aβ peptide in the second biological sample to the first biological sample, and if the amount of Aβ peptide in the second biological sample is increased relative to the first biological sample, identifying the subject as having increased Aβ peptide.

In other aspects, provided herein are assays for Alzheimer's disease or amnestic mild cognitive impairment comprising: administering an amylin or amylin analog challenge to a subject; obtaining a biological sample from the subject within 72 hours of the administration of the amylin or amylin analog challenge; measuring or quantifying the amount of Aβ peptide in the biological sample obtained from the subject administered the amylin or amylin analog challenge; and comparing the measured or quantified amount of Aβ peptide with a reference value, and if the amount of Aβ peptide is increased relative to the reference value, identifying the subject as having Alzheimer's disease or amnestic mild cognitive impairment.

In some aspects, provided herein are assays for Alzheimer's disease or amnestic mild cognitive impairment comprising: measuring or quantifying the amount of Aβ peptide in a first biological sample obtained from a subject prior to administration of an amylin or amylin analog challenge to the subject; administering an amylin or amylin analog challenge to the subject; measuring or quantifying the amount of Aβ peptide in a second biological sample obtained from the subject within 72 hours of the administration of the amylin or amylin analog challenge to the subject; comparing the measured or quantified amount of Aβ peptide in the second biological sample to the first biological sample, and if the amount of Aβ peptide in the second biological sample is increased relative to the first biological sample, identifying the subject as having Alzheimer's disease or amnestic mild cognitive impairment.

Also provided herein, in other aspects, are assays for detecting the presence of plaques comprising Aβ peptide in a subject comprising: administering an amylin or amylin analog challenge to a subject; obtaining a biological sample from the subject within 72 hours of the administration of the amylin or amylin analog challenge; measuring or quantifying the amount of Aβ peptide in the biological sample obtained from the subject administered the amylin or amylin analog challenge; and comparing the measured or quantified amount of Aβ peptide with a reference value, and if the amount of Aβ peptide is increased relative to the reference value, identifying the subject as having plaques comprising Aβ peptide.

In some aspects, provided herein are assays for detecting the presence of plaques comprising Aβ peptide in a subject comprising: measuring or quantifying the amount of Aβ peptide in a first biological sample obtained from a subject prior to administration of an amylin or amylin analog challenge to the subject; administering an amylin or amylin analog challenge to the subject; measuring or quantifying the amount of Aβ peptide in a second biological sample obtained from the subject within 72 hours of the administration of the amylin or amylin analog challenge; comparing the measured or quantified amount of Aβ peptide in the second biological sample to the first biological sample, and if the amount of Aβ peptide in the second biological sample is increased relative to the first biological sample, identifying the subject as having plaques comprising Aβ peptide.

In some embodiments of these assays and all such assays described herein, the biological sample is a blood sample, a serum sample, or a plasma sample.

In some embodiments of these assays and all such assays described herein, the amylin or amylin analog administered to the subject comprises a sequence of SEQ ID NOs: 3 or 4.

As used herein, "administering an amylin or amylin analog challenge" refers to any form of systemic administration of a therapeutic composition comprising amylin or an amylin agonist, such as intravenous or subcutaneous injection, as known to one of skill in the art. Therapeutic compositions comprising amylin or an amylin agonist for administration in the assays and methods described herein comprise a physiologically tolerable carrier together with amylin of SEQ ID NO: 3 or an amylin analog, such as an amylin analog of SEQ ID NO: 4 or SEQ ID NOs: 13-44, as described herein, dissolved or dispersed therein as an active ingredient. In preferred embodiments, the therapeutic composition comprising amylin or an amylin analog is not immunogenic when administered to a mammal or human patient for therapeutic purposes, unless so desired.

In preferred embodiments of the assays and methods described herein, the amylin or amylin agonist challenge is administered to a subject via intravenous or subcutaneous injection, following which, a biological sample, such as a blood sample, is obtained from the subject.

In some aspects, also provided herein, are methods for detecting Alzheimer's disease or amnestic mild cognitive impairment in a subject comprising: measuring or quantifying the amount of Aβ peptide in a biological sample obtained from a subject administered an amylin or amylin analog challenge within 72 hours prior to collection of the biological sample; and comparing the measured or quantified amount of Aβ peptide with a reference value, and if the amount of Aβ peptide is increased relative to the reference value, identifying the subject as having Alzheimer's disease or amnestic mild cognitive impairment.

In some aspects, described herein are methods for detecting Alzheimer's disease or amnestic mild cognitive impairment in a subject comprising: measuring or quantifying the amount of Aβ peptide in a first biological sample obtained from a subject prior to administration of an amylin or amylin analog challenge to the subject; measuring or quantifying the amount of Aβ peptide in a second biological sample obtained from the subject within 72 hours of administration of the amylin or amylin analog challenge; comparing the measured or quantified amount of Aβ peptide in the second biological sample to the first biological sample, and if the amount of Aβ peptide in the second biological sample is increased relative to the first biological sample, identifying the subject as having Alzheimer's disease or amnestic mild cognitive impairment.

Also provided herein, in other aspects, are methods for detecting the presence of plaques comprising Aβ peptide in a subject comprising: measuring or quantifying the amount of Aβ peptide in a biological sample obtained from a subject administered an amylin or amylin analog challenge, preferably within 72 hours prior to collection of the biological sample; and comparing the measured or quantified amount of Aβ peptide with a reference value, and if the amount of Aβ peptide is increased relative to the reference value, identifying the subject as having plaques comprising Aβ peptide.

In some aspects, provided herein are methods for detecting the presence of plaques comprising Aβ peptide in a subject: measuring or quantifying the amount of Aβ peptide in a first biological sample obtained from a subject prior to administration of an amylin or amylin analog challenge to the subject; measuring or quantifying the amount of Aβ peptide in a second biological sample obtained from the subject preferably within 72 hours of administration of the an amylin or amylin analog challenge; comparing the measured or quantified amount of Aβ peptide in the second biological sample to the first biological sample, and if the amount of Aβ peptide in the second biological sample is increased relative to the first biological sample, identifying the subject as having plaques comprising Aβ peptide.

In other aspects, provided herein are methods for detecting Alzheimer's disease or amnestic mild cognitive impairment in a subject comprising: administering an amylin or amylin analog challenge to a subject; obtaining a biological sample from the subject; measuring or quantifying the amount of Aβ peptide in the biological sample obtained from the subject administered amylin; and comparing the measured or quantified amount of Aβ peptide with a reference value, and if the amount of Aβ peptide is increased relative to the reference value, identifying the subject as having Alzheimer's disease or amnestic mild cognitive impairment. In some embodiments of these aspects and all such aspects described herein, the biological sample is obtained within 72 hours of the administration of the amylin or amylin analog challenge.

In some aspects, provided herein are methods for detecting Alzheimer's disease or amnestic mild cognitive impairment comprising: measuring or quantifying the amount of Aβ peptide in a first biological sample obtained from a subject prior to administration of an amylin or amylin analog challenge to the subject; administering an amylin or amylin analog challenge to the subject; measuring or quantifying the amount of Aβ peptide in a second biological sample obtained from the subject within, for example, 72 hours of the administration of the amylin or amylin analog challenge; comparing the measured or quantified amount of Aβ peptide in the second biological sample to the first biological sample, and if the amount of Aβ peptide in the second biological sample is increased relative to the first biological sample, identifying the subject as having Alzheimer's disease or amnestic mild cognitive impairment.

Also provided herein, in other aspects, are methods for detecting the presence of plaques comprising Aβ peptide in a subject comprising: administering an amylin or amylin analog challenge to a subject; obtaining a biological sample from the subject; measuring or quantifying the amount of Aβ peptide in the biological sample obtained from the subject administered amylin; and comparing the measured or quantified amount of Aβ peptide with a reference value, and if the amount of Aβ peptide is increased relative to the reference value, identifying the subject as having plaques comprising Aβ peptide. In some embodiments of these aspects and all such aspects described herein, the biological sample is obtained within 72 hours of the administration of the amylin or amylin analog challenge.

In some aspects, provided herein are methods for detecting the presence of plaques comprising Aβ peptide comprising: measuring or quantifying the amount of Aβ peptide in a first biological sample obtained from a subject prior to administration of an amylin or amylin analog challenge to the subject; administering an amylin or amylin analog challenge to the subject; measuring or quantifying the amount of Aβ peptide in a second biological sample obtained from the subject after the step of administration of the amylin or amylin analog challenge; comparing the measured or quantified amount of Aβ peptide in the second biological sample to the first biological sample, and if the amount of Aβ peptide in the second biological sample is increased relative to the first biological sample, identifying the subject as having plaques comprising Aβ peptide.

In some embodiments of these methods and all such methods described herein, the biological sample is a blood sample, a serum sample, or a plasma sample.

In some embodiments of these methods and all such methods described herein, the amylin or amylin analog administered to the subject comprises a sequence of SEQ ID NOs: 3 or 4.

In some embodiments of these methods and all such methods described herein, the methods can further comprise administration of one or more medications or therapeutic treatments. In some such embodiments, the medication is a cholinesterase inhibitor, such as, for example, galantamine, rivastigmine, or donepezil. In some such embodiments, the medication is an N-methyl D-aspartate (NMDA) antagonist, such as, for example, memantine, an N-methyl D-aspartate (NMDA) antagonist. In some such embodiments, the medication is amylin or an amylin analog, such as for example, pramlintide acetate. In some embodiments, the methods can further comprise administration of one or more cholinesterase inhibitors, such as, for example, galantamine, rivastigmine, or donepezil; one or more In N-methyl D-aspartate (NMDA) antagonists, such as, for example, memantine; amylin or an amylin analog, such as for example, pramlintide acetate; or any combination thereof. In some embodiments of these methods, the methods further comprise increasing audio and/or visual stimuli to the subject.

Also provided herein, in some aspects, are amylin and amylin analogs for imaging purposes. As described herein, the inventors have determined that amylin can traverse the blood brain barrier, and interacts with the amylin receptor (calcitonin receptor (CTR) and receptor activity modifying protein 3 (RAMP3) or CTR/RAMP3) and IDE (insulin degrading enzyme in the brain). Thus, compositions comprising amylin and amylin analogs can be used for neural imaging purposes, such as via positron emission topography (PET), if suitably labeled, for example, and in assays thereof.

In some aspects, provided herein are compositions comprising amylin or amylin analogs for use in positron emission topography as "radiotracers." PET scanning is used for diagnosis of brain disease, such as brain tumors, strokes, and neuron-damaging diseases which cause dementia (such as Alzheimer's disease), which all cause great changes in brain metabolism, which in turn causes easily detectable changes in PET scans. PET can be useful in early cases of certain dementias where the early damage is too diffuse and makes too little difference in brain volume and gross structure to change CT and standard MRI images enough to be able to reliably differentiate it from the normal range of cortical atrophy, and which does not cause clinical dementia.

Positron emission tomography (PET) measures emissions from radioactively labeled metabolically active chemicals that have been injected into the bloodstream. The emission data are computer-processed to produce 2- or 3-dimensional images of the distribution of the chemicals throughout the brain. The labeled amylin or amylin analogs, also known as amylin radiotracers, can be injected into the bloodstream and enter the brain. Sensors in the PET scanner can then detect the radioactivity as the amylin radiotracers accumulate in various regions of the brain. A computer uses the data gathered by the sensors to create multicolored 2- or 3-dimensional images that show where the compound acts in the brain.

Radionuclides used in PET scanning are typically isotopes with short half-lives such as carbon-11 (~20 min), nitrogen-13 (~10 min), oxygen-15 (~2 min), fluorine-18 (~110 min)., or rubidium-82(~1.27 min). Due to the short half-lives of most positron-emitting radioisotopes, the radiotracers have traditionally been produced using a cyclotron in close proximity to the PET imaging facility. Accordingly, in some embodiments of the aspects described herein, a composition comprising amylin or an amylin analog is chemically labeled with fluorine-18. In some embodiments of the aspects described herein, a composition comprising amylin or an amylin analog is chemically labeled with rubidium-82. In some embodiments of the aspects described herein, a composition comprising amylin or an amylin analog is chemically labeled with carbon-11. In some embodiments of the aspects described herein, a composition comprising amylin or an amylin analog is chemically labeled with nitrogen-13. In some embodiments of the aspects described herein, a composition comprising amylin or an amylin analog is chemically labeled with oxygen-15.

Accordingly, provided herein, in some aspects, are radiotracer compositions comprising an amylin or amylin analog labeled with a radionuclide.

In some embodiments of these compositions and all such composition described herein, the amylin or amylin analog comprises a sequence of SEQ ID NO: 3, SEQ ID NO: 4, or SEQ ID NOs: 13-44.

In some embodiments of these compositions and all such composition described herein, the radionuclide is fluorine-18 or rubidium-82.

Systems

Also provided herein, in other aspects and embodiments are systems (and computer readable media for causing computer systems) to perform methods for classifying, determining or diagnosing a patient having or at risk for having increased Aβ peptide in the brain, or a patient having or at risk for Alzheimer's disease. These systems are based, in part, on the inventors' discovery that administration of amylin causes an increase in the blood levels of another amyloid protein, Aβ peptide, in subjects or patients having Alzheimer's disease or.

Accordingly, in some aspects, provided herein are systems for classifying, determining, or diagnosing a patient having or at risk for having increased Aβ peptide in the brain, or a patient having or at risk for Alzheimer's disease. Such systems comprise: (a) a determination module configured to receive a biological sample, such as a blood sample from a subject administered amylin, measure or quantify the amount of in the biological sample of Aβ peptide, and to output information on the level or amount of Aβ peptide in the biological sample; (b) a storage device configured to store the output information of the level or amount of Aβ peptide in the biological sample from the determination module; (c) a comparison module adapted to receive input from the storage device and compare the data stored on the storage device with a reference level or amount of Aβ peptide, wherein if the level or amount of Aβ peptide is increased relative to the reference expression level data, the comparison module provides information to an output module that the biological sample is associated with a subject that has an increased Aβ peptide level or amount, or has or is at risk for Alzheimer's disease; and (d) an output module for displaying the information to the user.

Also provided herein, in some aspects, are systems for obtaining data from at least one biological sample obtained from a subject within 72 hours of amylin administration, the system comprising:

a. a determination module configured to receive said at least one biological sample obtained from a subject within 72 hours of administration of amylin or an amylin analog, and perform a measurement or quantification of the amount of Aβ peptide in the at least one biological sample to generate an Aβ peptide amount output;

b. a storage device configured to store said Aβ peptide amount output from said determination module;

c. a comparison module configured to receive said Aβ peptide amount output of the biological sample sample obtained from the subject within 72 hours of administration of amylin or an amylin analog, and perform at least one comparison analysis on said Aβ peptide amount output to determine the presence or absence of one of the following conditions and produce a comparison data output:

i. the biological sample from obtained from a subject within 72 hours of administration of amylin or an amylin analog has an increased amount of Aβ peptide relative to a reference value; or ii. the biological sample from obtained from a subject within 72 hours of administration of amylin or an amylin analog does not have increased amount of Aβ peptide relative to a reference value; and d. an output or display module for displaying a content based in part on the comparison data output from said comparison module, wherein the content comprises a signal indicative that the biological sample obtained from a subject within 72 hours of administration of amylin or an amylin analog has increased amount of Aβ peptide relative to the reference value, or a signal indicative that the biological sample obtained from the subject within 72 hours of administration of amylin or an amylin analog does not have increased amount of Aβ peptide relative to the reference value.

In some embodiments of these systems and all such systems described herein, the at least one biological sample is a blood sample, a serum sample, or a plasma sample.

In some embodiments of these systems and all such systems described herein, the amount of Aβ peptide being measured or quantified by the determination module of step (a) is Aβ42 of SEQ ID NO: 2.

In some embodiments of these systems and all such systems described herein, the at least one biological sample is obtained from the subject within 24 hours of administration of amylin or an amylin analog.

In some embodiments of these systems and all such systems described herein, the at least one biological sample is obtained from the subject within 4 hours of administration of amylin or an amylin analog.

In some embodiments of these systems and all such systems described herein, the amylin or amylin analog administered to the subject comprises a sequence of SEQ ID NO: 3, SEQ ID NO: 4, or SEQ ID NOs: 13-44.

In some embodiments of these systems and all such systems described herein, the comparison output of step (c) determines whether the amount of Aβ peptide in the biological sample is increased by at least one standard deviation above the reference value.

In some embodiments of these systems and all such systems described herein, the comparison output of step (c) determines whether the amount of Aβ peptide in the biological sample is increased by at least two standard deviations above the reference value.

Embodiments of the systems provided herein can be described through functional modules, which are defined by computer executable instructions recorded on computer readable media and which cause a computer to perform method steps when executed. The modules described herein are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules can perform other functions, thus the modules are not limited to having any particular functions or set of functions.

The computer readable storage media can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), USB memory, flash memory or other memory technology, CD-ROM (compact disc read only memory), DVDs (digital versatile disks) or other optical storage media, magnetic cassettes, magnetic tape, magnetic disk storage or other magnetic storage media, cloud server memory systems, other types of volatile and non-volatile memory, and any other tangible medium which can be used to store the desired information and which can accessed by a computer including and any suitable combination of the foregoing.

Computer-readable data embodied on one or more computer-readable storage media can define instructions, for example, as part of one or more programs, which, as a result of being executed by a computer, instruct the computer to perform one or more of the functions described herein, and/or various embodiments, variations and combinations thereof. Such instructions can be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable storage media on which such instructions are embodied can reside on one or more of the components of either of a system, or a computer readable storage medium described herein, or can be distributed across one or more of such components.

The computer-readable storage media can be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions can be embodied as any type of computer code (e.g., software or microcode) that can be employed to program a computer to implement aspects of the present invention. The computer executable instructions can be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments of the systems described herein include, at minimum, a determination module or device, a storage module or device, a comparison module or device, and an output module or device or display module or device. The functional modules can be executed on one, or multiple, computers, or by using one, or multiple, computer networks. The determination system has computer executable instructions to provide e.g., expression information in computer readable form.

The determination system can comprise any system for determining or assaying the level or amount of Aβ peptide in a sample, such as a blood, serum or plasma sample. Such systems can include, but are not limited to, PCR or quantitative PCR machines or devices, microarray devices or systems, Northern blot analysis systems, ELISA etc., as known to one of ordinary skill in the art.

The information determined in the determination system can be read by the storage device. As used herein the "storage device" is intended to include any suitable computing or processing apparatus or other device configured or adapted for storing data or information. Examples of an electronic apparatus suitable for use with the present invention include a stand-alone computing apparatus, data telecommunications networks, including local area networks (LAN), wide area networks (WAN), Internet, Intranet, and Extranet, local and remote servers, and local and distributed computer processing systems. Storage devices also include, but are not limited to: magnetic storage media, such as floppy discs, hard disc storage media, remote or local servers, magnetic tape, optical storage media such as CD-ROM, DVD, electronic storage media such as RAM, ROM, EPROM, EEPROM and the like, general hard disks and hybrids of these categories such as magnetic/optical storage media. The storage device is adapted or configured for having recorded thereon nucleic acid sequence information. Such information can be provided in digital form that can be transmitted and read electronically, e.g., via the Internet, on a diskette, via USB (universal serial bus) or via any other suitable mode of communication.

As used herein, "stored" refers to a process for encoding information on the storage device. Those skilled in the art can readily adopt any of the presently known methods for recording information on known media to generate manufactures comprising information relating to immune stimulating microbes.

In some embodiments of the aspects and embodiments described herein, the reference data stored in the storage device to be read by the comparison module is e.g., the level or amount of Aβ peptide obtained from the same patient or subject at, for example, an earlier timepoint, such as prior to administration of amylin or an amylin analog, or a level or amount of Aβ peptide obtained from a patient sample not having Alzheimer's disease, The "comparison module" can use a variety of available software programs and formats for the comparison operative to compare level or amount of Aβ peptide information data determined in the determination system to one or more reference samples and/or stored reference data.

The comparison module, or any other module of the invention, can include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application can include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in some embodiments, users can directly access data (via Hypertext links for example) residing on Internet databases using a HTML interface provided by Web browsers and Web servers.

The comparison module provides a computer readable comparison result that can be processed in computer readable form by predefined criteria, or criteria defined by a user, to provide a content based in part on the comparison result that may be stored and output as requested by a user using a display module or output device.

The content based on the comparison result, can be, for example, the amount or level of Aβ, the relative fold-change or increase in percentage of of Aβ peptide, or the relative risk of Alzheimer's disease. Alternatively, or additionally, the content based on the comparison result can be a further treatment step indicated for the patient, e.g., administration of a cholinesterase inhibitors, such as, for example, RAZADYNE® (galantamine), EXELON® (rivastigmine), or ARICEPT® (donepezil), an N-methyl D-aspartate (NMDA) antagonist, such as, for example, NAMENDA® (memantine), continued administration of amylin, or a combination thereof.

In some embodiments of the systems described herein, the content based on the comparison result is displayed on a computer monitor. In some embodiments of the systems described herein, the content based on the comparison result is displayed through printable media. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., tablet or mobile phone devices, or any other type of processor, visual display devices such as flat panel displays, cathode ray tubes and the like, as well as computer printers of various types.

In some embodiments of the systems described herein, a World Wide Web browser is used for providing a user interface for display of the content based on the comparison result. It should be understood that other modules of the invention can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces.

The modules of the machine, or those used in the computer readable medium, can assume numerous configurations. For example, function may be provided on a single machine or distributed over multiple machines.

Systems and computer readable media described herein are merely illustrative embodiments of the invention for performing methods of diagnosis in an individual, and are not intended to limit the scope of the invention. Variations of the systems and computer readable media described herein are possible and are intended to fall within the scope of the invention.

Kits for Detection of Increased Aβ peptide

Conveniently, in some aspects, the amount or level of Aβ peptide in a biological sample for use in the assays and methods described herein can be measured or quantified using a kit comprising, for example, amylin or an amylin analog for administration, and one or more reagents for detecting the amount or level of Aβ peptide in the biological sample, such as, for example, a blood, serum, or plasma sample. As used herein, a "reagent for detecting the amount or level of Aβ peptide" can include any molecule capable of specifically detecting Aβ peptide including, but not limited to, monoclonal and polyclonal antibodies and fragments thereof, and oligonucleotides. For example, the kit can comprise amylin or an amylin analog in a formulation suitable for administration to a subject and an antibody specific for Aβ peptide. The antibody specific for Aβ peptide can be used in an ELISA analysis, as known to one of ordinary skill in the art. Optionally, the kits include, for example, instructions for administration of amylin or an amylin analog, and/or a device for the administration of the amylin or amylin analog, such as a needle and syringe, and/or one or more containers for collection of the biological sample from the subject administered amylin or an amylin analog, and/or one or more reagents for detecting the amount or level of Aβ peptide in biological sample obtained from the subject administered amylin or amylin analog, or for performing the assays or methods described herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Embodiments of the various aspects described herein can be illustrated by the following numbered paragraphs:

1. A method for reducing Aβ peptide deposition in the brain, the method comprising administering to a subject having increased Aβ peptide deposition in the brain a therapeutically effective amount of amylin or an amylin analog.
2. A method for inhibiting progression of Alzheimer's disease or amnestic mild cognitive impairment, the method comprising administering to a subject having or at risk for Alzheimer's disease or amnestic mild cognitive a therapeutically effective amount of amylin or an amylin analog.
3. The method of paragraphs 1 or 2, wherein the administering is at least once a week.
4. The method of paragraphs 1 or 2, wherein the administering is at least twice a week.
5. The method of paragraphs 1 or 2, wherein the administering is at least three times a week.
6. The method of paragraphs 1 or 2, wherein the administering is at least four times a week.
7. The method of paragraphs 1 or 2, wherein the administering is daily.
8. The method of any one of paragraphs 1-7, wherein the administering is performed by injection.
9. The method of paragraph 8, wherein the injection is a systemic injection.
10. The method of any one of paragraphs 1-9, further comprising determining the amount or quantity of Aβ peptide in a biological sample obtained from the subject within 72 hours of said administering.
11. The method of paragraph 10, wherein the determining is within 24 hours of said administering.
12. The method of paragraph 10, wherein the determining is within 4 hours of said administering.
13. The method of any one of paragraphs 10-12, wherein the biological sample is obtained from the subject within 24 hours of said administering.
14. The method of any one of paragraphs 10-12, wherein the biological sample is obtained from the subject within 4 hours of said administering.
15. The method of any one of paragraphs 10-14, wherein the biological sample is a blood sample, a serum sample, or a plasma sample.
16. The method of any one of paragraphs 10-15, wherein the Aβ peptide is Aβ42 of SEQ ID NO: 2.
17. The method of any one of paragraphs 1-16, wherein the amylin or amylin analog administered to the subject comprises a sequence of SEQ ID NO: 3, SEQ ID NO: 4, or SEQ ID NOs: 13-44.
18. The method of any one of paragraphs 1-17, wherein the amylin or amylin analog is administered as a unit dose composition.
19. The method of any one of paragraphs 1 or 3-18, wherein the subject having increased Aβ peptide deposition in the brain has or is at risk for Alzheimer's disease or amnestic mild cognitive impairment (aMCI).
20. The method of any one of paragraphs 1-19, further comprising administering to the subject a cholinesterase inhibitor.
21. The method of paragraph 20, wherein the cholinesterase inhibitor is galantamine, rivastigmine, or donepezil.
22. The method of any one of paragraphs 1-21, further comprising administering to the subject an N-methyl D-aspartate (NMDA) antagonist.
23. The method of paragraph 22, wherein the N-methyl D-aspartate (NMDA) antagonist is memantine.
24. An assay for selecting a therapy for a subject having or at risk for Aβ peptide deposition in the brain, the assay comprising:
    a. subjecting a biological sample, obtained from a subject administered an amylin or amylin analog challenge within 72 hours prior to collection of the biological sample, to an assay that determines the amount of Aβ peptide in the biological sample;
    b. determining the amount of Aβ peptide in the biological sample; and
    c. selecting an amylin or amylin analog therapy for the subject when the determined amount of Aβ peptide in the biological sample is increased relative to a reference value; or not selecting an amylin or amylin analog therapy for the subject when the determined amount of Aβ peptide in the biological sample is below a reference value.
25. The assay of paragraph 24, further comprising, when the determined amount of Aβ peptide in the biological sample is increased relative to a reference value, the step of treating the subject with amylin or an amylin analog therapy.
26. The assay of paragraph 25, wherein the treating is at least once a week.
27. The assay of paragraph 25, wherein the treating is at least twice a week.
28. The assay of paragraph 25, wherein the treating is at least three times a week.
29. The assay of paragraph 25, wherein the treating is at least four times a week.
30. The assay of paragraph 25, wherein the treating is daily.
31. The assay of any one of paragraphs 24-30, wherein the biological sample is obtained from the subject within 24 hours of administration to the subject of the amylin or amylin analog challenge.
32. The assay of any one of paragraphs 24-30, wherein the biological sample is obtained from the subject within 4 hours of administration to the subject of the amylin or amylin analog challenge.
33. The assay of any one of paragraphs 24-32, wherein the biological sample is a blood sample, a serum sample, or a plasma sample.
34. The assay of any one of paragraphs 24-33, wherein the Aβ peptide is Aβ42 of SEQ ID NO: 2.
35. The assay of any one of paragraphs 24-34, wherein the amylin or amylin analog administered to the subject prior to the collection of the biological sample comprises a sequence of SEQ ID NO: 3, SEQ ID NO: 4, or SEQ ID NOs: 13-44.
36. The assay of any one of paragraphs 24-35, wherein the subject having or at risk for Aβ peptide deposition in the brain has or is at risk for Alzheimer's disease or amnestic mild cognitive impairment (aMCI).
37. The assay of any one of paragraphs 24-36, wherein the determined amount of Aβ peptide in the biological sample is increased by at least one standard deviation above the reference value.

38. The assay of any one of paragraphs 24-36, wherein the determined amount of Aβ peptide in the biological sample is increased by at least two standard deviations above the reference value.
39. A method for selecting a therapy for a subject having or at risk for Aβ peptide deposition in the brain, the method comprising:
   a. subjecting a biological sample, obtained from a subject administered an amylin or amylin analog challenge within 72 hours prior to collection of the biological sample, to an assay or method that determines the amount of Aβ peptide in the biological sample;
   b. determining the amount of Aβ peptide in the biological sample; and
   c. selecting an amylin or amylin analog therapy for the subject when the determined amount of Aβ peptide in the biological sample is increased relative to a reference value; or not selecting an amylin or amylin analog therapy for the subject when the determined amount of Aβ peptide in the biological sample is below a reference value.
40. The method of paragraph 39, wherein the determined amount of Aβ peptide in the biological sample is increased by at least one standard deviation above the reference value.
41. The method of paragraph 39, wherein the determined amount of Aβ peptide in the biological sample is increased by at least two standard deviations above the reference value.
42. The method of any one of paragraphs 39-41, further comprising, when the determined amount of Aβ peptide in the biological sample is increased relative to a reference value, the step of treating the subject with amylin or an amylin analog therapy.
43. The method of paragraph 42, wherein the treating is at least once a week.
44. The method of paragraph 42, wherein the treating is at least twice a week.
45. The method of paragraph 42, wherein the treating is at least three times a week.
46. The method of paragraph 42, wherein the treating is at least four times a week.
47. The method of paragraph 42, wherein the treating is daily.
48. The method of any one of paragraphs 39-47, wherein the biological sample is obtained from the subject within 24 hours of administration to the subject of the amylin or amylin analog challenge.
49. The method of any one of paragraphs 39-47, wherein the biological sample is obtained from the subject within 4 hours of administration to the subject of the amylin or amylin analog challenge.
50. The method of any one of paragraphs 39-49, wherein the biological sample is a blood sample, a serum sample, or a plasma sample.
51. The method of any one of paragraphs 39-50, wherein the Aβ peptide is Aβ42 of SEQ ID NO: 2.
52. The method of any one of paragraphs 39-51, wherein the amylin or amylin analog administered to the subject prior to the collection of the biological sample comprises a sequence of SEQ ID NO: 3, SEQ ID NO: 4, or SEQ ID NOs: 13-44.
53. The method of any one of paragraphs 39-52, wherein the subject having or at risk for Aβ peptide deposition in the brain has or is at risk for Alzheimer's disease or amnestic mild cognitive impairment (aMCI).
54. A radiotracer composition comprising an amylin or amylin analog labeled with a radionuclide.
55. The radiotracer composition of paragraph 54, wherein the amylin or amylin analog comprises a sequence of SEQ ID NO: 3, SEQ ID NO: 4, or SEQ ID NOs: 13-44.
56. The radiotracer composition of paragraphs 54 or 55, wherein the radionuclide is fluorine-18 or rubidium-82.
57. An assay comprising:
   a. measuring or quantifying the amount of Aβ peptide in a biological sample obtained from a subject administered an amylin or amylin analog challenge within 72 hours prior to collection of the biological sample; and
   b. identifying the subject as having increased Aβ peptide in the brain and selecting a therapy if the measured or quantified amount of Aβ peptide is increased relative to a reference value.
58. An assay comprising:
   a. measuring or quantifying the amount of Aβ peptide in a first biological sample obtained from a subject prior to administration of an amylin or amylin analog challenge to the subject;
   b. measuring or quantifying the amount of Aβ peptide in a second biological sample obtained from the subject within 72 hours of administration of an amylin or amylin analog challenge; and
   c. identifying the subject as having increased Aβ peptide in the brain and selecting a therapy if the amount of Aβ peptide in the second biological sample is increased relative to the first biological sample.
59. An assay for selecting a therapy for a subject having or at risk for Alzheimer's disease or amnestic mild cognitive impairment comprising:
   a. measuring or quantifying the amount of Aβ peptide in a biological sample obtained from a subject administered an amylin or amylin analog challenge within 72 hours prior to collection of the biological sample; and
   b. selecting a therapy for the subject having or at risk for Alzheimer's disease or amnestic mild cognitive impairment if the amount of Aβ peptide measured or quantified is increased relative to a reference value.
60. An assay for selecting a therapy for a subject having or at risk for Alzheimer's disease or amnestic mild cognitive impairment comprising:
   a. measuring or quantifying the amount of Aβ peptide in a first biological sample obtained from a subject prior to administration of an amylin or amylin analog challenge to the subject;
   b. measuring or quantifying the amount of Aβ peptide in a second biological sample obtained from the subject within 72 hours of administration of an amylin or amylin analog challenge; and
   c. identifying the subject as having increased Aβ peptide in the brain and optionally selecting a therapy if the amount of Aβ peptide in the second biological sample is increased relative to the first biological sample.
61. An assay for identifying the presence of plaques comprising Aβ peptide in a subject comprising:
   a. measuring or quantifying the amount of Aβ peptide in a biological sample obtained from a subject administered an amylin or amylin analog challenge within 72 hours prior to collection of the biological sample; and
   b. identifying the subject as having plaques comprising Aβ peptide if the amount of Aβ peptide is increased relative to a reference value.

62. The assay of paragraph 61, wherein the reference value is the value of Aβ peptide in a biological sample from said subject prior to administration of the amylin or amylin analog challenge.

63. The assay of any one of paragraphs 57-62, wherein the amount of Aβ peptide in the biological sample is increased by at least one standard deviation above the reference value or first biological sample.

64. The assay of any one of paragraphs 57-62, wherein the amount of Aβ peptide in the biological sample is increased by at least two standard deviations above the reference value or first biological sample.

65. An assay for identifying the presence of plaques comprising Aβ peptide in the brain comprising:
  a. measuring or quantifying the amount of Aβ peptide in a first biological sample obtained from a subject prior to administration of an amylin or amylin analog challenge to the subject;
  b. measuring or quantifying the amount of Aβ peptide in a second biological sample obtained from the subject within 72 hours of administration of an amylin or amylin analog challenge; and
  c. identifying the subject as having plaques comprising Aβ peptide in the brain and optionally selecting a therapy if the amount of Aβ peptide in the second biological sample is increased relative to the first biological sample.

66. The assay of paragraph 65, wherein the amount of Aβ peptide in the biological sample is increased by at least one standard deviation above the first biological sample.

67. The assay of paragraph 65, wherein the amount of Aβ peptide in the biological sample is increased by at least two standard deviations above the first biological sample.

68. The assay of any one of paragraphs 57-67, wherein the biological sample is a blood sample, a serum sample, or a plasma sample.

69. The assay of any one of paragraphs 57-68, wherein the amylin or amylin analog administered to the subject comprises a sequence of SEQ ID NO: 3, SEQ ID NO: 4, or SEQ ID NOs: 13-44.

70. The assay of any one of paragraphs 57-69, wherein the Aβ peptide being measured or quantified is Aβ42 of SEQ ID NO: 2.

71. The assay of any one of paragraphs 57-70, wherein the measuring or quantifying of steps (a) or (b) is within 24 hours of the amylin or amylin analog challenge.

72. The assay of any one of paragraphs 57-70, wherein the measuring or quantifying of steps (a) or (b) is within 4 hours of the amylin or amylin analog challenge.

73. An assay comprising:
  a. administering an amylin or amylin analog challenge to a subject;
  b. obtaining a biological sample from the subject after the administration of the amylin or amylin analog challenge;
  c. measuring or quantifying the amount of Aβ peptide in the biological sample obtained from the subject administered the amylin or amylin analog challenge; and
  d. identifying the subject as having increased Aβ peptide in the brain if the amount of Aβ peptide is increased relative to the reference value.

74. An assay comprising:
  a. measuring or quantifying the amount of Aβ peptide in a first biological sample obtained from a subject prior to administration of an amylin or amylin analog challenge to the subject;
  b. administering an amylin or amylin analog challenge to the subject;
  c. measuring or quantifying the amount of Aβ peptide in a second biological sample obtained from the subject within 72 hours of the administration of the amylin or amylin analog challenge; and
  d. identifying the subject as having increased Aβ peptide in the brain if the amount of Aβ peptide in the second biological sample is increased relative to the first biological sample.

75. An assay for identifying a subject having or at risk for Alzheimer's disease or amnestic mild cognitive impairment comprising:
  a. administering an amylin or amylin analog challenge to a subject;
  b. obtaining a biological sample from the subject within 72 hours of the administration of the amylin or amylin analog challenge;
  c. measuring or quantifying the amount of Aβ peptide in the biological sample obtained from the subject administered the amylin or amylin analog challenge; and
  d. identifying the subject as having Alzheimer's disease or amnestic mild cognitive impairment if the measured or quantified amount of Aβ peptide is increased relative to a reference value.

76. An assay for identifying a subject having or at risk for Alzheimer's disease or amnestic mild cognitive impairment comprising:
  a. measuring or quantifying the amount of Aβ peptide in a first biological sample obtained from a subject prior to administration of an amylin or amylin analog challenge to the subject;
  b. administering an amylin or amylin analog challenge to the subject;
  c. measuring or quantifying the amount of Aβ peptide in a second biological sample obtained from the subject within 72 hours of the administration of the amylin or amylin analog challenge to the subject; and
  d. identifying the subject as having Alzheimer's disease or amnestic mild cognitive impairment if the amount of Aβ peptide measured or quantified in the second biological sample is increased relative to the first biological sample.

77. An assay for detecting the presence of plaques comprising Aβ peptide in the brain in a subject comprising:
  a. administering an amylin or amylin analog challenge to a subject;
  b. obtaining a biological sample from the subject within 72 hours of the administration of the amylin or amylin analog challenge;
  c. measuring or quantifying the amount of Aβ peptide in the biological sample obtained from the subject administered the amylin or amylin analog challenge; and
  d. identifying the subject as having plaques comprising Aβ peptide in the brain if the amount of Aβ peptide is increased relative to a reference value.

78. An assay for detecting the presence of plaques in the brain comprising Aβ peptide in a subject comprising
  a. measuring or quantifying the amount of Aβ peptide in a first biological sample, obtained from a subject prior to administration of an amylin or amylin analog challenge to the subject;
  b. administering an amylin or amylin analog challenge to the subject;
  c. measuring or quantifying the amount of Aβ peptide in a second biological sample obtained from the subject within 72 hours of the administration of the amylin or amylin analog challenge; and d. identifying the subject as having plaques in the brain comprising Aβ peptide, if the amount of Aβ peptide in the second biological sample is increased relative to the first biological sample.

79. The assay of any one of paragraphs 73-78, wherein the amount of Aβ peptide in the biological sample is increased by at least one standard deviation above the reference value or first biological sample.

80. The assay of any one of paragraphs 73-78, wherein the amount of Aβ peptide in the biological sample is increased by at least two standard deviations above the reference value or first biological sample.

81. The assay of any one of paragraphs 73-80, wherein the biological sample is a blood sample, a serum sample, or a plasma sample.

82. The assay of any one of paragraphs 73-81, wherein the amylin or amylin analog administered to the subject comprises a sequence of SEQ ID NO: 3, SEQ ID NO: 4, or SEQ ID NOs: 13-44.

83. The assay of any one of paragraphs 73-82, wherein the Aβ peptide being measured or quantified is Aβ42 of SEQ ID NO: 2.

84. The assay of any one of paragraphs 73-83, wherein the amylin or amylin analog challenge is administered to the subject via intravenous or subcutaneous administration.

85. The assay of any one of paragraphs 73-84, wherein the measuring or quantifying of steps (b) or (c) is within 24 hours of the amylin or amylin analog challenge.

86. The assay of any one of paragraphs 73-85, wherein the measuring or quantifying of steps (b) or (c) is within 4 hours of the amylin or amylin analog challenge.

87. A method for detecting Alzheimer's disease or amnestic mild cognitive impairment in a subject comprising:
    a. measuring or quantifying the amount of Aβ peptide in a biological sample obtained from a subject administered an amylin or amylin analog challenge within 72 hours prior to collection of the biological sample; and
    b. identifying the subject as having Alzheimer's disease or amnestic mild cognitive impairment if the amount of Aβ peptide is increased relative to a reference value.

88. A method for detecting Alzheimer's disease or amnestic mild cognitive impairment in a subject comprising:
    a. measuring or quantifying the amount of Aβ peptide in a first biological sample obtained from a subject prior to administration of an amylin or amylin analog challenge to the subject;
    b. measuring or quantifying the amount of Aβ peptide in a second biological sample obtained from the subject within 72 hours of administration of the amylin or amylin analog challenge; and
    c. identifying the subject as having Alzheimer's disease or amnestic mild cognitive impairment if the amount of Aβ peptide in the second biological sample is increased relative to the first biological sample.

89. A method for detecting the presence of plaques comprising Aβ peptide in the brain in a subject comprising:
    a. using any of the assays of any one of paragraphs 24-38 or 57-86; and
    b. identifying the subject as having plaques comprising Aβ peptide in the brain, if the amount of Aβ peptide measured or quantified by the assay is increased relative to a reference value.

90. A method for detecting Alzheimer's disease or amnestic mild cognitive impairment in a subject comprising:
    a. administering an amylin or amylin analog challenge to a subject;
    b. using any of the assays of any one of paragraphs 24-38 or 57-86; and
    c. identifying the subject as having Alzheimer's disease or amnestic mild cognitive impairment if the amount of Aβ peptide measured or quantified by the assay is increased relative to a reference value.

91. A method for detecting the presence of plaques comprising Aβ peptide in a subject comprising:
    a. administering an amylin or amylin analog challenge to a subject;
    b. using any of the assays of any one of paragraphs 24-38 or 57-86; and
    c. identifying the subject as having plaques comprising Aβ peptide, if the amount of Aβ peptide measured or quantified by the assay is increased relative to a reference value.

92. The method of any one of paragraphs 87 or 88, wherein the biological sample is a blood sample, a serum sample, or a plasma sample.

93. The method of any one of paragraphs 87-92, wherein the amount of Aβ peptide in the biological sample is increased by at least one standard deviation above the reference value or first biological sample.

94. The method of any one of paragraphs 87-92, wherein the amount of Aβ peptide in the biological sample is increased by at least two standard deviations above the reference value or first biological sample.

95. The method of any one of paragraphs 87-94, wherein the amylin or amylin analog administered to the subject comprises a sequence of SEQ ID NO: 3, SEQ ID NO: 4, or SEQ ID NOs: 13-44.

96. The method of any one of paragraphs 87-95, wherein the Aβ peptide being measured or quantified is Aβ42 of SEQ ID NO: 2.

97. The method of any one of paragraphs 87-96, wherein the amylin or amylin analog challenge is administered to the subject via intravenous or subcutaneous administration.

98. The method of any one of paragraphs 87-97, wherein if the measured or quantified amount of Aβ peptide is increased relative to a reference value or relative to the first biological sample, the method further comprises administration of a therapeutically effective amount of amylin or an amylin analog.

99. The method of paragraph 98, wherein the amylin or amylin analog administered to the subject comprises a sequence of SEQ ID NO: 3, SEQ ID NO: 4, or SEQ ID NOs: 13-44.

100. The method of paragraph 98, wherein the amylin analog comprises pramlintide acetate of SEQ ID NO: 4.

101. The method of any one of paragraphs 87-100, wherein if the measured or quantified amount of Aβ peptide is increased relative to a reference value or relative to the first biological sample, the method further comprises administration of a therapeutically effective amount of a cholinesterase inhibitor.

102. The method of paragraph 101, wherein the cholinesterase inhibitor is galantamine, rivastigmine, or donepezil.

103. The method of any one of paragraphs 87-102, wherein if the measured or quantified amount of Aβ peptide is increased relative to a reference value or relative to the first biological sample, the method further comprises administration of a therapeutically effective amount of an N-methyl D-aspartate (NMDA) antagonist.

104. The method of paragraph 103, wherein the N-methyl D-aspartate (NMDA) antagonist is memantine.

105. The method of any one of paragraphs 87-104, wherein if the measured or quantified amount of Aβ peptide is increased relative to a reference value or relative to the first biological sample, the method further comprises increasing audio stimuli, visual stimuli, or a combination thereof to the subject.

106. The assay or method of any one of paragraphs 24-53 or 57-105, wherein the step of determining, quantifying, or measuring the amount of Aβ peptide in the biological sample is performed using a non-human machine.

107. A system for obtaining data from at least one biological sample obtained from a subject within 72 hours of amylin administration, the system comprising:
   a. a determination module configured to receive said at least one biological sample obtained from a subject within 72 hours of administration of amylin or an amylin analog, and perform a measurement or quantification of the amount of Aβ peptide in the at least one biological sample to generate an Aβ peptide amount output;
   b. a storage device configured to store said Aβ peptide amount output from said determination module;
   c. a comparison module configured to receive said Aβ peptide amount output of the biological sample sample obtained from the subject within 72 hours of administration of amylin or an amylin analog, and perform at least one comparison analysis on said Aβ peptide amount output to determine the presence or absence of one of the following conditions and produce a comparison data output:
      i. the biological sample from obtained from a subject within 72 hours of administration of amylin or an amylin analog has an increased amount of Aβ peptide relative to a reference value; or
      ii. the biological sample from obtained from a subject within 72 hours of administration of amylin or an amylin analog does not have increased amount of Aβ peptide relative to a reference value; and
   d. an output or display module for displaying a content based in part on the comparison data output from said comparison module, wherein the content comprises a signal indicative that the biological sample obtained from a subject within 72 hours of administration of amylin or an amylin analog has increased amount of Aβ peptide relative to the reference value, or a signal indicative that the biological sample obtained from the subject within 72 hours of administration of amylin or an amylin analog does not have increased amount of Aβ peptide relative to the reference value.

108. The system of paragraph 107, wherein the at least one biological sample is a blood sample, a serum sample, or a plasma sample.

109. The system of any one of paragraphs 107-108, wherein the amount of Aβ peptide being measured or quantified by the determination module of step (a) is Aβ42 of SEQ ID NO: 2.

110. The system of any one of paragraphs 107-109, wherein the at least one biological sample is obtained from the subject within 24 hours of administration of amylin or an amylin analog.

111. The system of any one of paragraphs 107-110, wherein the at least one biological sample is obtained from the subject within 4 hours of administration of amylin or an amylin analog.

112. The system of any one of paragraphs 107-111, wherein the amylin or amylin analog administered to the subject comprises a sequence of SEQ ID NO: 3, SEQ ID NO: 4, or SEQ ID NOs: 13-44.

113. The system of any one of paragraphs 107-112, wherein the comparison output of step (c) determines whether the amount of Aβ peptide in the biological sample is increased by at least one standard deviation above the reference value.

114. The system of any one of paragraphs 107-112, wherein the comparison output of step (c) determines whether the amount of Aβ peptide in the biological sample is increased by at least two standard deviations above the reference value.

115. An amylin or an amylin analog for use in reducing Aβ peptide deposition in the brain of a subject.

116. An amylin or an amylin analog for use in inhibiting progression of Alzheimer's disease or amnestic mild cognitive impairment in a subject.

117. The use of paragraphs 115 or 116, wherein the amylin or an amylin analog is formulated for administration to a subject at least once a week.

118. The use of any one of paragraphs 115 or 116, wherein the amylin or an amylin analog is formulated for administration to a subject at least twice a week.

119. The use of any one of paragraphs 115 or 116, wherein the amylin or an amylin analog is formulated for administration to a subject at least three times a week.

120. The use of any one of paragraphs 115 or 116, wherein the amylin or an amylin analog is formulated for administration to a subject at least four times a week.

121. The use of any one of paragraphs 115 or 116, wherein the amylin or an amylin analog is formulated for administration to a subject daily.

122. The use of any one of paragraphs 115-121, wherein the amylin or an amylin analog is formulated for administration to a subject by injection.

123. The use of paragraph 122, wherein the injection is a systemic injection.

124. The use of any one of paragraphs 115-123, wherein the amylin or amylin analog comprises a sequence of SEQ ID NO: 3, SEQ ID NO: 4, or SEQ ID NOs: 13-44.

125. The use of any one of paragraphs 115-124, wherein the amylin or amylin analog is formulated as a unit dose composition.

126. The use of any one of paragraphs 115 or 117-125, wherein the subject having Aβ peptide deposition in the brain has or is at risk for Alzheimer's disease or amnestic mild cognitive impairment (aMCI).

EXAMPLES

Using a sample of homebound elderly, we found a significant positive relationship between amylin and Aβ42 in blood only in patients with AD or amnestic mild cognitive impairment (amnestic MCI), a prodromal stage of AD (Table 1). In contrast, we did not observe the relationship between Aβ42 and amylin among those with normal cognitive function. Without wishing to be bound or limited by theory, the positive relationship between plasma Aβ and amylin in AD can be explained by: 1) there is a large amount of Aβ42 in the AD brains but there is little or no Aβ42 in normal brains, 2) amylin is a short peptide, which freely passes through the brain blood barrier (BBB) into the brain (Banks and Kastin, 1998), 3) both Aβ42 and amylin compete with each other for degradation by the insulin degrading enzyme (IDE) in the brain (Qiu et al., 1998; Bennett et al., 2003; Shen et al., 2006).

Amylin is a short peptide with 37 amino acids, and is co-secreted with insulin by β-cells in the pancreas. The main role of amylin in the brain is to reduce food intake and control body weight (Geary, 1999). Giving a person exogenous amylin peripherally or intracerebroventricularly can equally reduce appetite and food intake (Olsson et al., 2007), which has been used in the clinic. Pramlintide, a modified amylin, with only 3 amino acid changes to reduce aggregation, has become a medication for type 2 diabetics to control overeating. Subcutaneous injections of Pramlintide have been in clinical practice and proven to be safe.

As demonstrated herein at FIGS. 2A-2J, amylin challenge blood assays can be used to detect Aβ deposits in the brain. TgAPP2576 mice (n=5) and control mice (n=5) were used. Intraperitoneal injection of amylin (20 mg/kg) was performed, and blood was drawn and collected at pre-injection, after injection at 5 minutes, 1 hr and 24 hrs. Serum Aβ1-40 and Aβ1-42 were measured using ELISA assay. The results of serum Aβ1-40 and Aβ1-42 for each individual mouse are shown. This experiment has been repeated twice for each mouse and similar results were obtained.

Figure 3B:
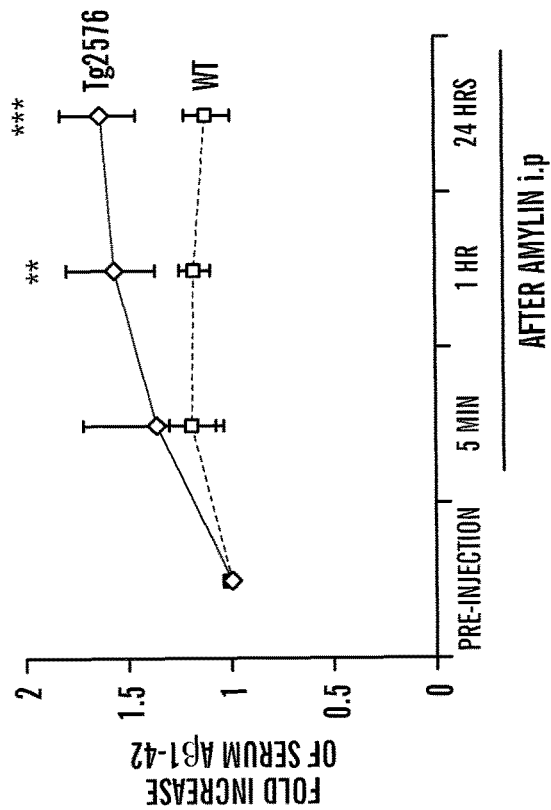
Figure 3A:
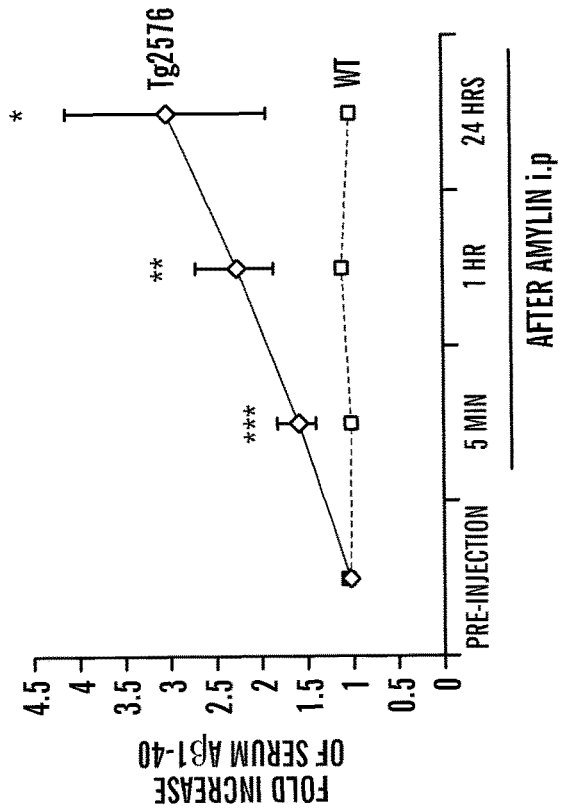

As shown at FIGS. 3A-3E, amylin injection removes Aβ from the brain into blood in APP transgenic mice. Both the Tg2576 and wild type (WT) mice were used for the amylin challenge test. FIGS. 3A-3B. Amylin (20 mg/kg) was intraperitoneally injected (i.p), and blood was drawn and collected at the time points of pre-injection (the control n=7; Tg2576 n=11), after injection 5 minutes (the control n=7; Tg2576 n=6), 1 hr (the control n=7; Tg2576 n=10) and 24 hrs (the control n=7; Tg2576 n=11). Serum Aβ1-40 and Aβ1-42 were measured by using the ELISA assays. FIGS. 3C-3E. The levels of serum Aβ1-40 and Aβ1-42 at pre-injection of amylin were treated as 1 s, and the relative fold increase after amylin injection at each time point was shown and compared with the pre-injection level by using two-way ANOVA. *$p<0.01$; $p<0.05$ and *$p<0.10$.

Figure 4:
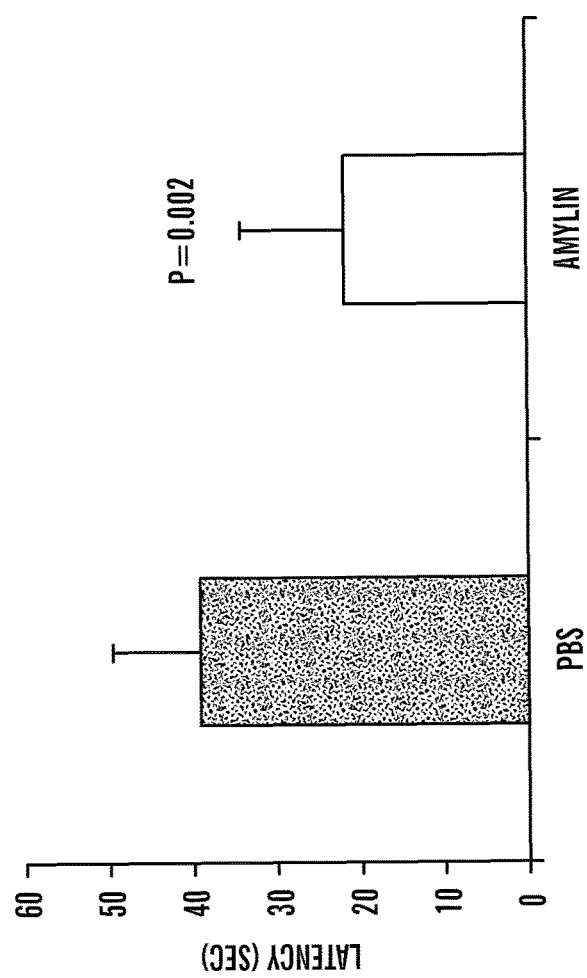
FIG. 4 demonstrates that amylin treatment improves Y-water maze in APP transgenic Mice: 5XFAD mice were treated with either i.p amylin or saline for 8 weeks followed by Y-water maze test. The average latency of recognizing the object after the training was calculated for each group (n=10) and statistical significance for the comparison is shown.

A demonstration that amylin treatment improves Y-water maze behavior and cognition in APP transgenic is shown at FIG. 4. 5XFAD mice were treated with either i.p amylin or saline for 8 weeks followed by Y-water maze test. The average latency of recognizing the object after the training was calculated for each group (n=10) and statistical significance for the comparison is shown.

Figure 5A:
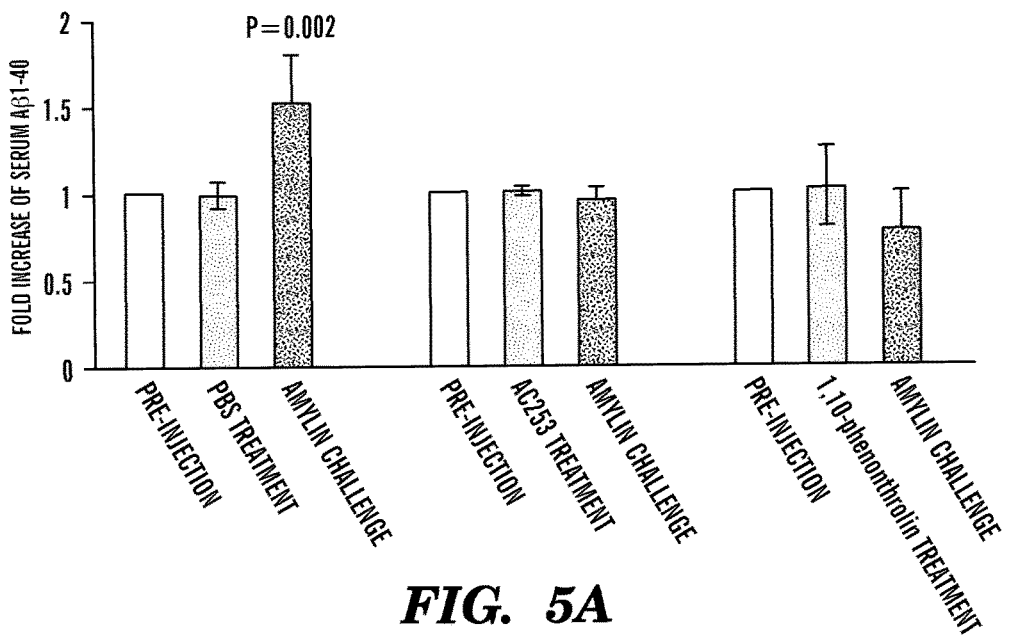
FIGS. 5A-5B demonstrate that the removal of A$\beta$ from the brain into blood is through amylin receptor and insulin degrading enzyme: Tg2576 mice were used for the amylin challenge test. The mice received blood draws before any treatment. Then the mice had intraperitoneally injection (i.p) of PBS, AC253 (amylin receptor antagonist) or 1,10-phenonthrolin (IDE inhibitor) and received another blood draw 24 hrs post the treatment followed by i.p amylin (20 mg/kg). The final blood draw was conducted after 24 hrs post i.p amylin. Serum A$\beta$1-40 (5A) and A$\beta$1-42 (5B) were measured by using the ELISA assays. The levels of serum A$\beta$1-40 and A$\beta$1-42 at pre-injection of amylin were treated as 1 s, and the relative fold increases with different treatments were calculated and compared with the pre-injection level by using two-way ANOVA. P values for statistical significance are shown.
Figure 5B:
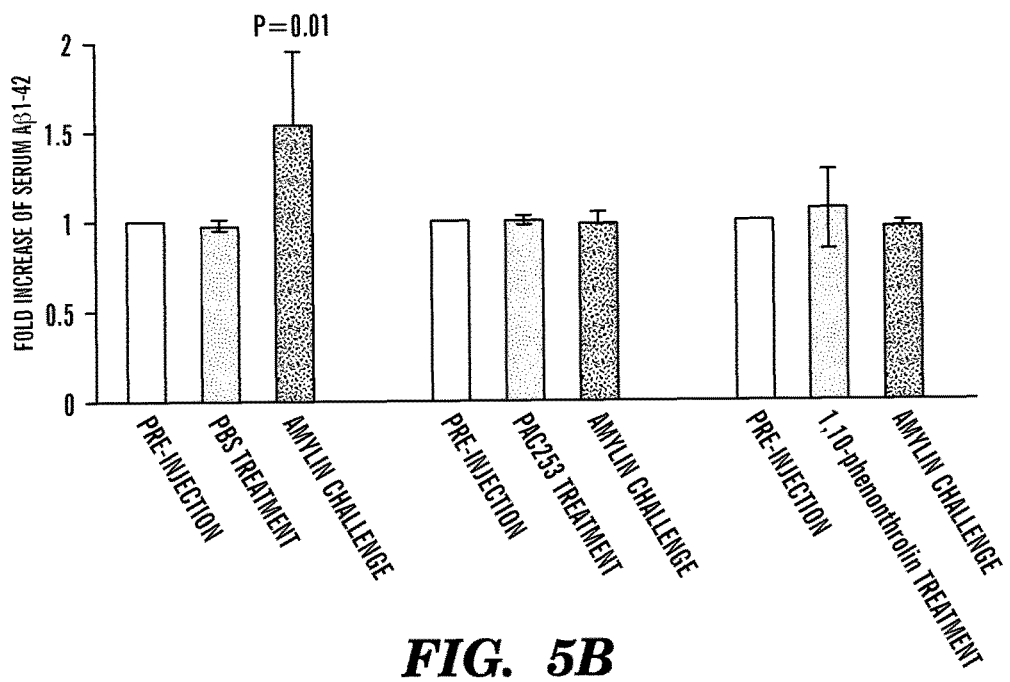
Figure 6A:
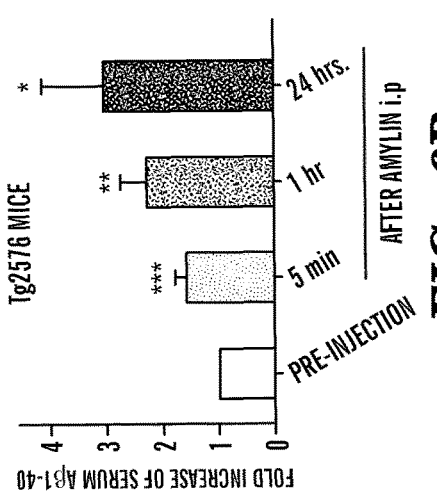
FIGS. 6A-6D demonstrate amylin injection and serum A$\beta$ in mice. Both control mice (wild type) and Tg2576 mice were used for the amylin injection test. Amylin (20 mcg/kg) was intraperitoneally injected (i.p), and blood was drawn at the following time points: at baseline or pre-injection (controls n=7; Tg2576 n=11), at 5 minutes (controls n=7; Tg2576 n=6), at 1 hr (controls n=7; Tg2576 n=10) and at 24 hrs (controls n=7; Tg2576 n=11) post injection. Serum A$\beta$1-40 and A$\beta$1-42 were measured by using the ELISA assays. The levels of serum A$\beta$1-40 and A$\beta$1-42 at pre-injection of amylin were treated as 1 s, and the relative fold increase after amylin injection at each time point was shown and compared with the pre-injection level by using a two-way ANOVA. *$p<0.01$; $p<0.05$ and *$p<0.10$. Compared to the pre-injection levels, all the Tg2576 mice, but none of the control mice (wild type), had surges of serum A$\beta$40 and A$\beta$42 after a single amylin injection.
Figure 6B:
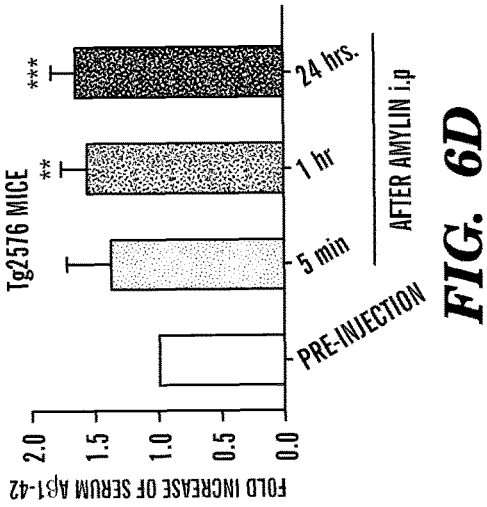
Figure 6C:
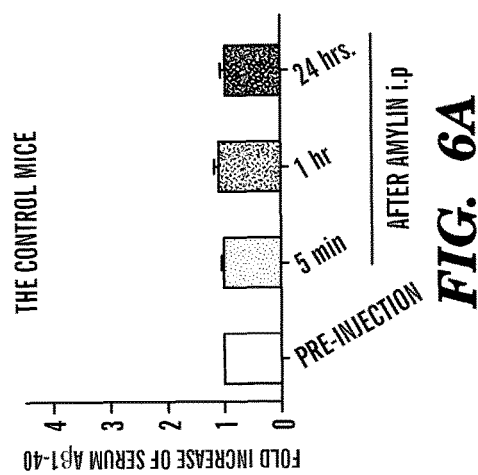
Figure 6D:
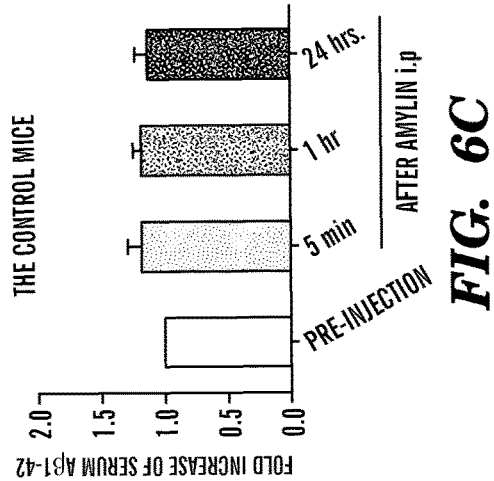

FIGS. 5A-5B demonstrate that the removal of Aβ from the brain into blood is through amylin receptor and insulin degrading enzyme. Tg2576 mice were used for the amylin challenge test. The mice received blood draws before any treatment. Then the mice had intraperitoneally injection (i.p) of PBS, AC253 (amylin receptor antagonist) or 1,10-phenonthrolin (IDE inhibitor) and received another blood draw 24 hrs post the treatment followed by i.p amylin (20 mg/kg). The final blood draw was conducted after 24 hrs post i.p amylin. Serum Aβ1-40 (5A) and Aβ1-42 (5B) were measured by using the ELISA assays. The levels of serum Aβ1-40 and Aβ1-42 at pre-injection of amylin were treated as 1 s, and the relative fold increases with different treatments were calculated and compared with the pre-injection level by using two-way ANOVA. P values for statistical significance are shown.

FIGS. 6A-6D depict amylin injection and serum Aβ in mice. Both control mice (wild type) and Tg2576 mice were used for the amylin injection test. Amylin (20 mcg/kg) was intraperitoneally injected (i.p), and blood was drawn at the following time points: at baseline or pre-injection (controls n=7; Tg2576 n=11), at 5 minutes (controls n=7; Tg2576 n=6), at 1 hr (controls n=7; Tg2576 n=10) and at 24 hrs (controls n=7; Tg2576 n=11) post injection. Serum Aβ1-40 and Aβ1-42 were measured by using the ELISA assays. The levels of serum Aβ1-40 and Aβ1-42 at pre-injection of amylin were treated as 1 s, and the relative fold increase after amylin injection at each time point was shown and compared with the pre-injection level by using a two-way ANOVA. *$p<0.01$; $p<0.05$ and *$p<0.10$. Compared to the pre-injection levels, all the Tg2576 mice, but none of the control mice (wild type), had surges of serum Aβ40 and Aβ42 after a single amylin injection. FIGS. 6A-6D show the group differences at different time points, demonstrating that the peripheral amylin injection can induce increases of both blood Aβ40 and Aβ42 specifically in Tg2576 mice.

FIG. 7 depicts results of i.p injection of pramlintide, an analog of amylin, into one Tg2576 mouse (A1) and two wild type mice (N1 and N2) and comparison of their serum Aβ40 level before and after the injection. Again, one pramlintide injection induced the surge of serum Aβ40 in the Tg2576 mouse, but not in those wild type mice, indicating that pramlintide can have the same effect as amylin.

Increased blood Aβ induced by the amylin injection reflecting the brain pathology is demonstrated by FIGS. 8A-8B. To further prove that the surge of Aβ in serum provoked by the amylin challenge correlates with Aβ pathology in the brain, another type of APP transgenic mice, 5XFAD, was used, which have abundant Aβ42, but very little or no Aβ40, in the brain when the animals are young. FIG. 8A shows that the i.p injection of amylin into 5XFAD mice aged 3 months resulted in an increased level of Aβ1-42, but not Aβ1-40, in serum. Using another APP mouse line which carries the APP Dutch mutation and mainly produces Aβ40, but not Aβ42, the amylin challenge provoked only a surge of Aβ1-40, but not Aβ1-42, in blood (FIG. 8B).

Figure 9:
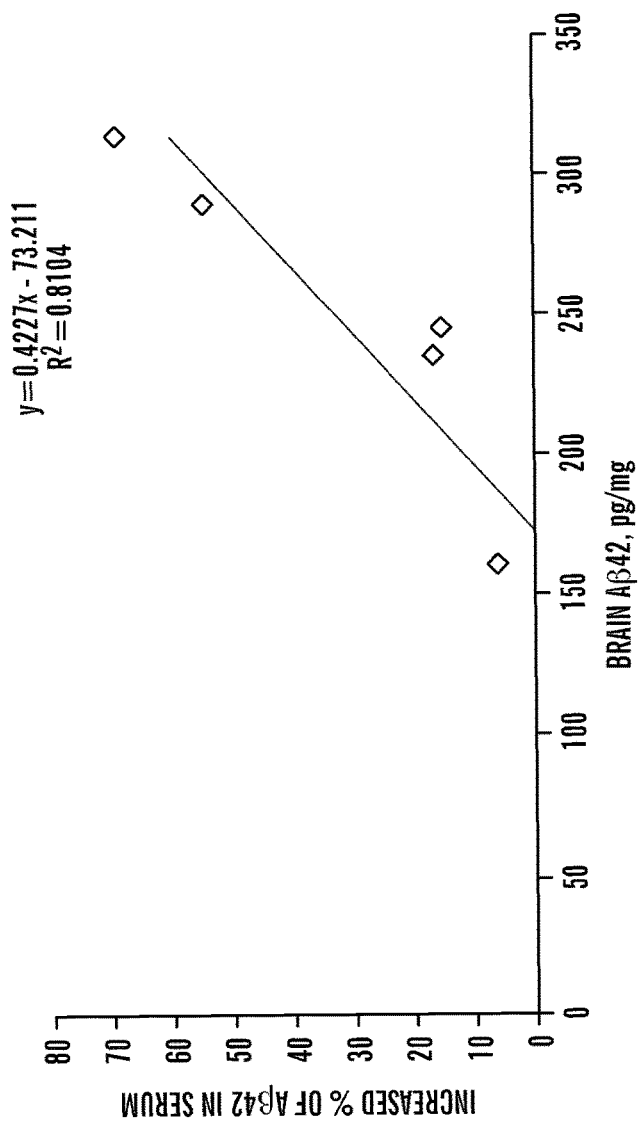
FIG. 9 demonstrates that using different aged 5XFAD mice peripheral amylin injection resulted in an increase of serum Aβ levels reflecting the amounts of Aβ in the brains The higher the levels of Aβ and the number of amyloid plaques in the brain, the higher fold of serum Aβ was increased after the peripheral amylin challenge. The data further demonstrates the specificity of peripheral amylin injection as an amylin challenge test for the AD pathology in the brain.

FIG. 9 demonstrates that using different aged 5XFAD mice peripheral amylin injection resulted in an increase of serum Aβ levels reflecting the amounts of Aβ in the brains. The higher the levels of Aβ and the number of amyloid plaques in the brain, the higher fold of serum Aβ was increased after the peripheral amylin challenge. The data further demonstrates the specificity of peripheral amylin injection as an amylin challenge test for the AD pathology in the brain.

Figure 10B:
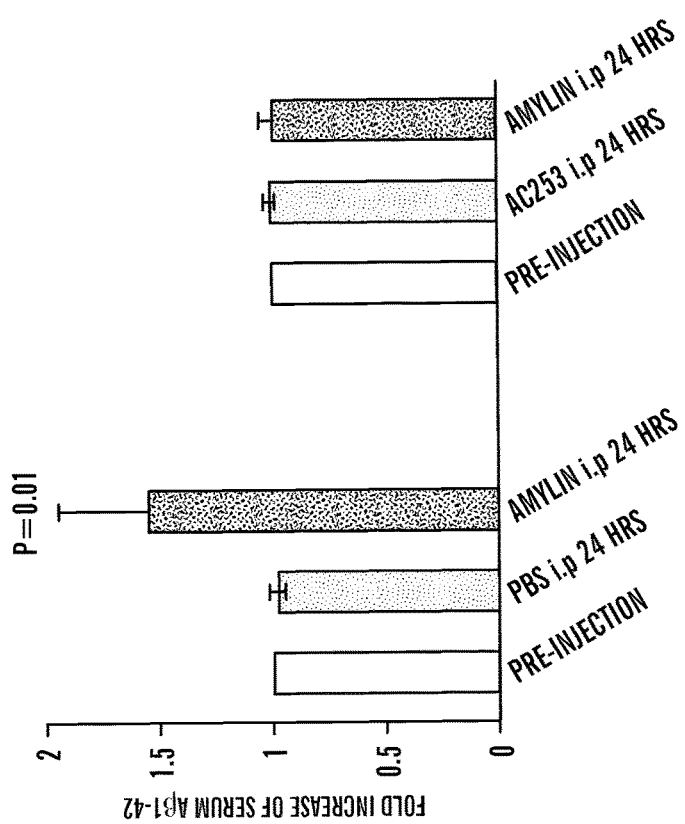
FIGS. 10A-10C depict mechanistic studies of the amylin challenge test. To elucidate whether the effects of the amylin challenge is through the amylin receptor, we used amylin receptor antagonists to pretreat the Tg2576 mice. The surges of serum Aβ at 24 hrs post the peripheral injection of amylin were completely blocked by the pre-treatment of amylin receptor antagonists, AC253, indicating that this process is specifically mediated by amylin binding to its receptor. The amylin receptor is a complex of the calcitonin receptor (CTR) and receptor activity-modifying proteins 1 or 3 (RAMP1 or RAMP3), while CTR/RAMP1 binds amylin and calcitonin gene-related peptide (CGRP), CTR/RAMP3 binds amylin only. Next we injected human CGRP, and observed no significant surge of serum Aβ, indicating that CTR/RAMP3 is the receptor complex mediating the effect by amylin to induce the removal of Aβ from the brain into blood (FIG. 10C).
Figure 10A:
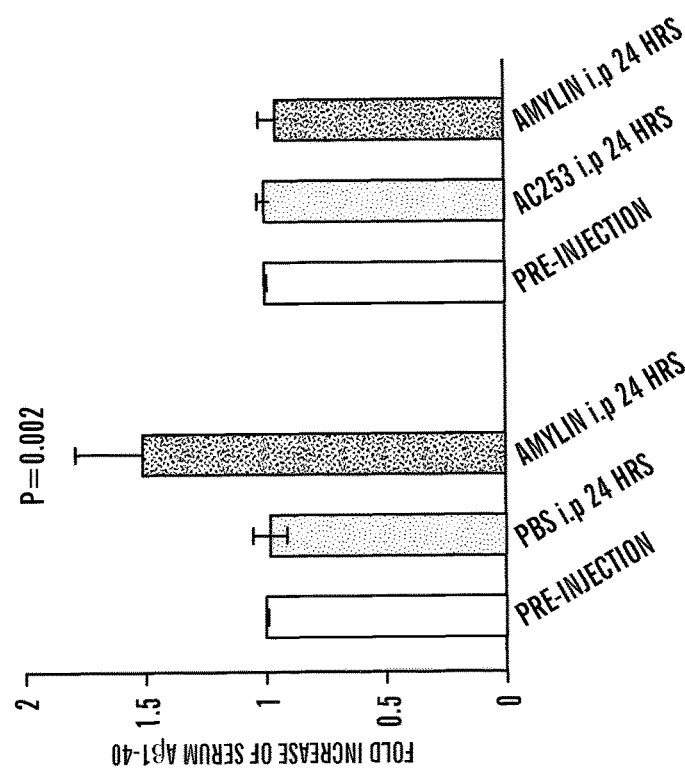
Figure 10C:
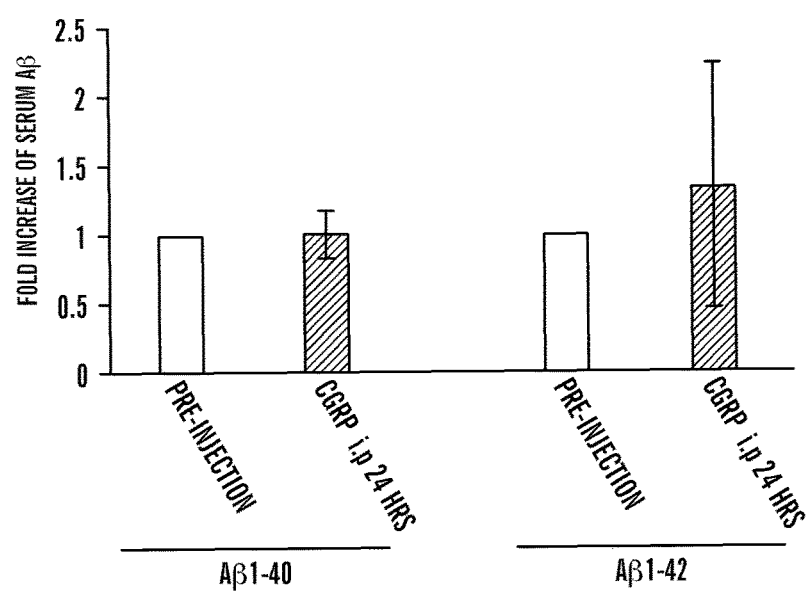

Mechanistic studies of the amylin challenge test are depicted in FIGS. 10A-10C. To elucidate whether the effects of the amylin challenge is through the amylin receptor, we used amylin receptor antagonists to pretreat the Tg2576 mice. The surges of serum Aβ at 24 hrs post the peripheral injection of amylin were completely blocked by the pre-treatment of amylin receptor antagonists, AC253, indicating that this process is specifically mediated by amylin binding to its receptor. The amylin receptor is a complex of the calcitonin receptor (CTR) and receptor activity-modifying proteins 1 or 3 (RAMP1 or RAMP3), while CTR/RAMP1 binds amylin and calcitonin gene-related peptide (CGRP), CTR/RAMP3 binds amylin only. Next we injected human CGRP, and observed no significant surge of serum $A\beta$, indicating that CTR/RAMP3 is the receptor complex mediating the effect by amylin to induce the removal of $A\beta$ from the brain into blood.

Figure 11B:
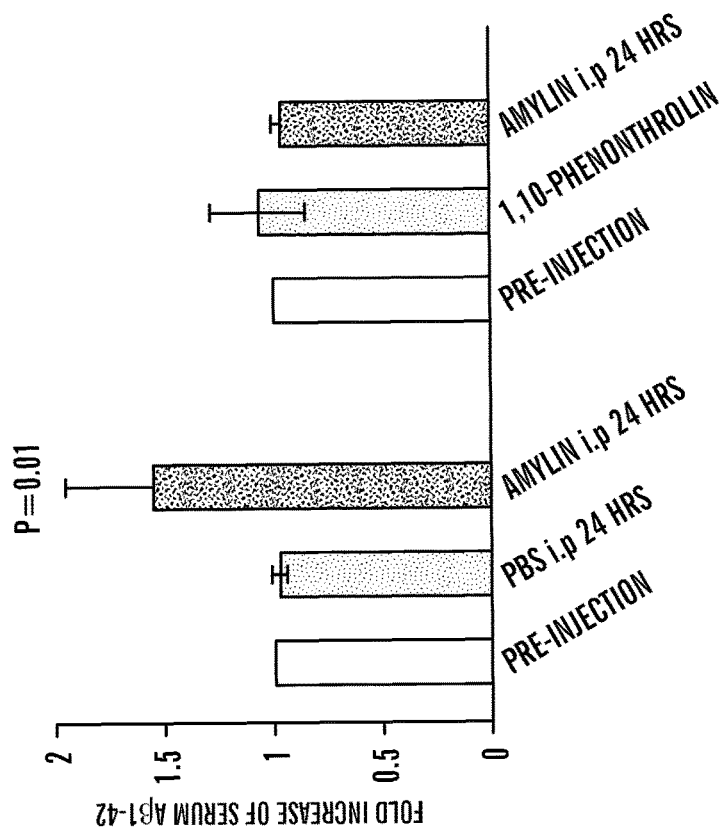
FIGS. 11A-11B demonstrate that surges of serum Aβ are completely blocked at 24 hrs post the peripheral injection of amylin. As amylin and Aβ are degraded by the same protease, IDE, we next pre-treated the Tg2576 mice with 1-10 phenonthrolin, a metalloprotease inhibitor to inhibit the activity of IDE, followed by the amylin challenge. It was next tested whether CTR/RAMP3 and IDE form a complex in this process to regulate Aβ in the brain. To prove this, RAMP3 was immunoprecipitated by its specific antibody from the brain extracts of 5XFAD transgenic mice treated with amylin followed by a western blot with an IDE antibody, demonstrating the existence of the complex of CTR/RAMP3 and IDE. Another experiment with IDE immunoprecipitation and then RAMP3 western blot also illustrated the complex.
Figure 11A:
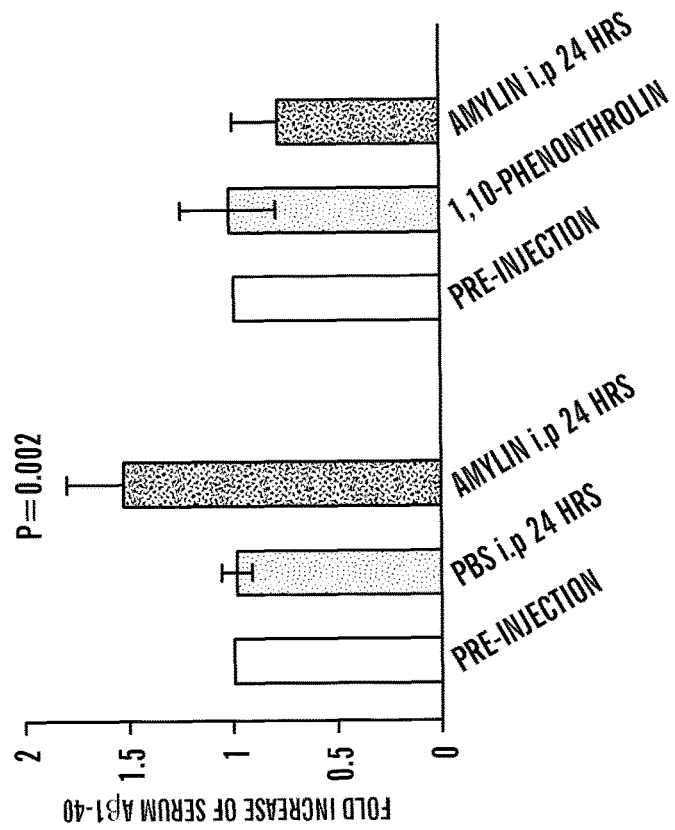

FIGS. 11A-11B demonstrate that surges of serum $A\beta$ are completely blocked at 24 hrs post the peripheral injection of amylin. As amylin and $A\beta$ are degraded by the same protease, IDE, we next pre-treated the Tg2576 mice with 1-10 phenonthrolin, a metalloprotease inhibitor to inhibit the activity of IDE, followed by the amylin challenge. It was next tested whether CTR/RAMP3 and IDE form a complex in this process to regulate $A\beta$ in the brain. To prove this, RAMP3 was immunoprecipitated by its specific antibody from the brain extracts of 5XFAD transgenic mice treated with amylin followed by a western blot with an IDE antibody, demonstrating the existence of the complex of CTR/RAMP3 and IDE. Another experiment with IDE immunoprecipitation and then RAMP3 western blot also illustrated the complex.

Figure 12:
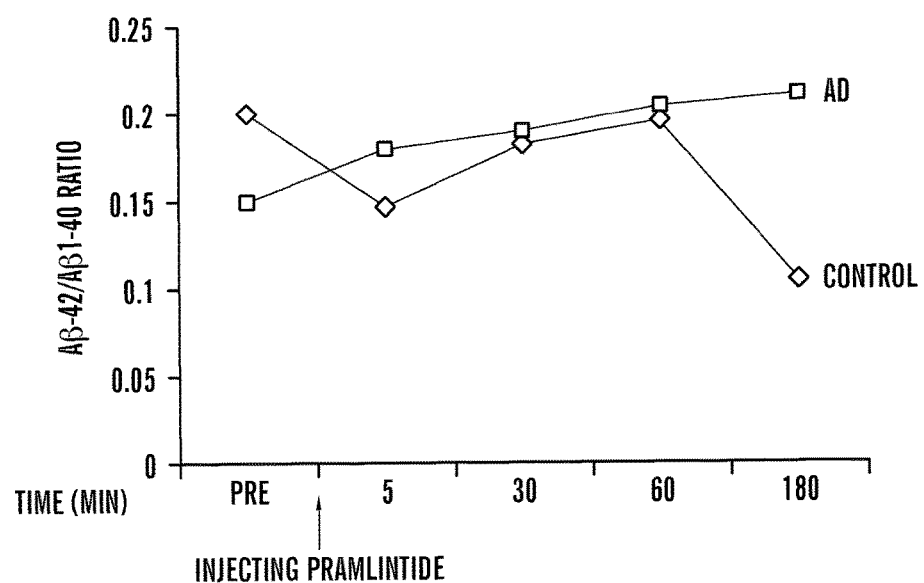
FIG. 12 demonstrates that while plasma Aβ1-42 was increased after the injection of pramlintide in an Alzheimer's disease human patient, it was decreased in the control. Subcutaneous injections of one dose of pramlintide (60 mcg) was performed in two subjects followed in the research registry of the BU ADC, one control and one probable Alzheimer's disease. Blood was drawn to collect plasma samples before the injection and at 5, 30, 60 and 180 minutes after the injection. Vital signs and blood glucose were monitored at these time points and prior to discharge of the subject from the facility. One hour after the injection, the subjects were offered a standard meal. Plasma Aβ1-40 and Aβ1-42 were measured (Table 2). Both subjects had stable vital signs during the trial, and did not have nausea, vomiting, abdominal pain, headache, dizziness and itching during the trial or over the next 48 hours. In the AD subject, plasma Aβ1-42 was increased until 30 minutes and then decreased after the injection of pramlintide. In contrast, in the control subject, plasma Aβ1-42 was decreased at all the time points (Table 2). We also calculated the ratio of plasma Aβ1-42/Aβ1-40 ratio.

FIG. 12 provides in vivo human data demonstrating that while plasma $A\beta1-42$ was increased after the injection of pramlintide in an Alzheimer's disease human patient, it was decreased in the control. Subcutaneous injections of one dose of pramlintide (60 mcg) was performed in two subjects followed in the research registry of the BU ADC, one control and one probable Alzheimer's disease. Blood was drawn to collect plasma samples before the injection and at 5, 30, 60 and 180 minutes after the injection. Vital signs and blood glucose were monitored at these time points and prior to discharge of the subject from the facility. One hour after the injection, the subjects were offered a standard meal. Plasma $A\beta1-40$ and $A\beta1-42$ were measured (Table 2). Both subjects had stable vital signs during the trial, and did not have nausea, vomiting, abdominal pain, headache, dizziness and itching during the trial or over the next 48 hours. In the AD subject, plasma $A\beta1-42$ was increased until 30 minutes and then decreased after the injection of pramlintide. In contrast, in the control subject, plasma $A\beta1-42$ was decreased at all the time points (Table 2). We also calculated the ratio of plasma $A\beta1-42/A\beta1-40$ ratio, and FIG. 12 shows a significant increase of $A\beta1-42/A\beta1-40$ ratio in the AD subject, whereas a decrease of the ratio was observed in the control subject, at 3 hours post-injection, after the challenge of pramlintide. A broad range of pramlintide doses (30 to 300 mcg tid) are used clinically and shown to reduce postprandial plasma glucose concentrations safely (NDA21-332). The human results provided herein are encouraging, in part, because the dose of pramlintide (60 mcg) used was only moderate.

Figure 13:
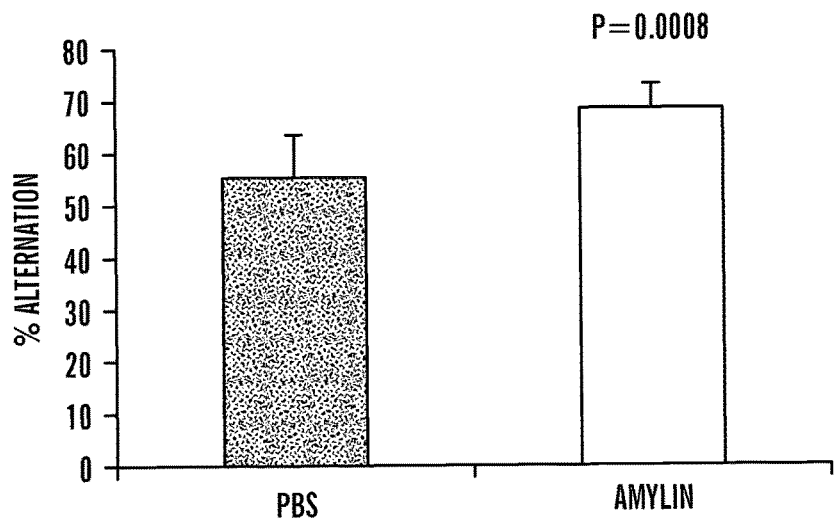
FIG. 13 demonstrates long-term treatment with amylin on memory in the APP transgenic mice. Since amylin can enhance the removal of Aβ out of the brain into blood, it was tested whether amylin and its analogs can be a treatment for AD. Thus, we treated 5XFAD mice aged 2 months old with i.p injection of amylin (20 mcg/kg) vs. saline (n=8 in each group) daily for 10 weeks, and then conducted Y Maze Spontaneous Alternation test for measuring the willingness of mice to explore new environments. As shown, the % alternation rate was significantly increased by the amylin treatment of these mice.

FIG. 13 further demonstrates long-term treatment with amylin on memory in the APP transgenic mice. Since amylin can enhance the removal of $A\beta$ out of the brain into blood, it was tested whether amylin and its analogs can be a treatment for AD. Thus, we treated 5XFAD mice aged 2 months old with i.p injection of amylin (20 mcg/kg) vs. saline (n=8 in each group) daily for 10 weeks, and then conducted Y Maze Spontaneous Alternation test for measuring the willingness of mice to explore new environments. As shown, the % alternation rate was significantly increased by the amylin treatment of these mice.

Figure 14:
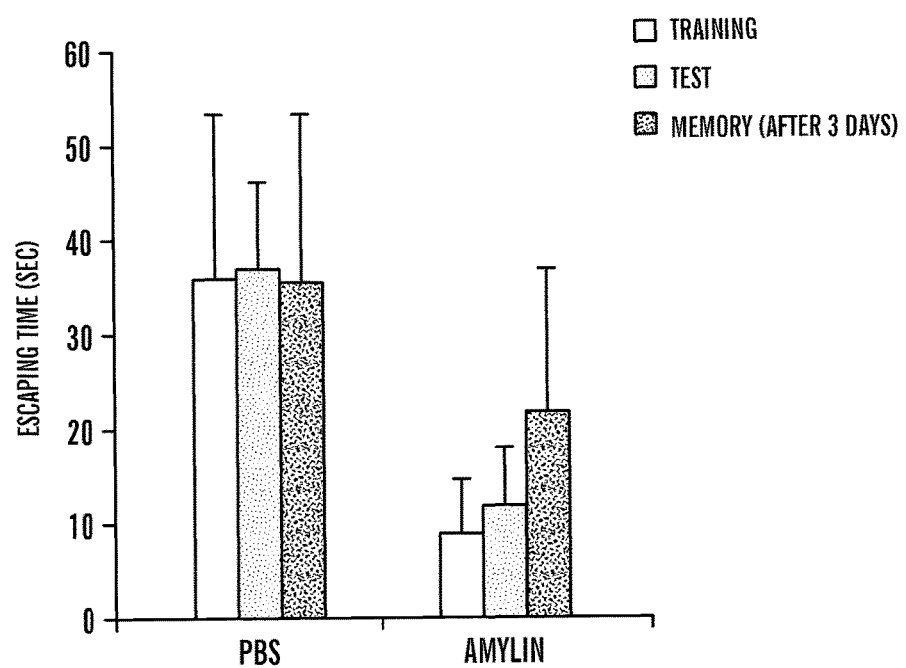
FIG. 14 further demonstrates long-term treatment with amylin on memory in the APP transgenic mice using the Y-water Maze test, for the acquisition and retention aspects of learning and memory. The data shows that the amylin treatment significantly reduced the time for acquisition, e.g. the mice spent less time escaping onto the platform in the water maze; for memory retention, e.g. the mice exhibited effect in shortening the time to find the platform at 30 minutes and at 3 days, than the placebo ($p<0.02$).

FIG. 14 further demonstrates long-term treatment with amylin on memory in the APP transgenic mice using the Y-water Maze test, for the acquisition and retention aspects of learning and memory. The data shows that the amylin treatment significantly reduced the time for acquisition, e.g. the mice spent less time escaping onto the platform in the water maze; for memory retention, e.g. the mice exhibited effect in shortening the time to find the platform at 30 minutes and at 3 days, than the placebo (p<0.02).

Figures 15, 16:
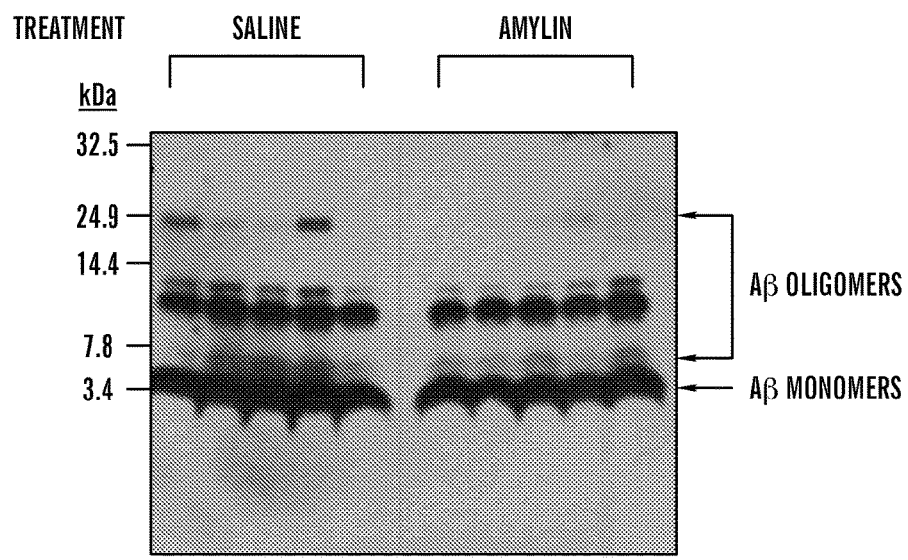
FIG. 15 shows a mechanism of amylin treatment on the AD pathology in the brain. Changes of Aβ in the brain were examined after the amylin treatment in 5XFAD mice using both western blots and ELISA assays. While the amylin treatment did not change the amount of Aβ monomers in the brain compared to the saline treatment, the amylin treatment significantly reduced the amount of Aβ oligomers, which are much more neurotoxic than the monomers. Thus, without wishing to be bound or limited by theory, the benefits of memory improvement from amylin treatment is mediated, in part, by 1) removing A(from the AD brain into blood and 2) reducing the amount of Aβ oligomers in the brain.
FIG. 16 depicts that amylin and its analogs may also play a role of or β or γ secretase inhibitor. When the trial with pramlintide on two subjects was conducted, both subjects showed the levels of plasma Aβ1-40 and Aβ1-42 were reduced significantly at 3 hours post- injection of pramlintide despite the AD subject initially showing an increase of plasma Aβ1-42 after the pramlintide injection (Table 2). Part of Aβ sequence, 17-23 amino acids, is shown to inhibit γ secretase to generate more Aβ (Li et al. 2010) as a mechanism of self-regulation. γ secretase inhibition has been proposed to be a treatment for AD, but the clinical trials failed mainly due to its adverse events. We compared the sequences of Aβ and amylin, and found that there are some homologies between the inhibitor sequence within Aβ and the region of amylin. This indicates that amylin and its analogs can play a role of γ secretase inhibitor that can be another mechanism of amylin treatment for AD. Pramlintide has a safety profile in the clinical use for diabetes.

FIG. 15 shows a mechanism of amylin treatment on the AD pathology in the brain. Changes of $A\beta$ in the brain were examined after the amylin treatment in 5XFAD mice using both western blots and ELISA assays. While the amylin treatment did not change the amount of $A\beta$ monomers in the brain compared to the saline treatment, the amylin treatment significantly reduced the amount of $A\beta$ oligomers, which are much more neurotoxic than the monomers. Thus, without wishing to be bound or limited by theory, the benefits of memory improvement from amylin treatment is mediated, in part, by 1) removing $A\beta$ from the AD brain into blood and 2) reducing the amount of $A\beta$ oligomers in the brain.

FIG. 16 depicts that amylin and its analogs may also play a role of $\gamma$ secretase inhibitor. When the trial with pramlintide on two subjects was conducted, both subjects showed the levels of plasma $A\beta1-40$ and $A\beta1-42$ were reduced significantly at 3 hours post-injection of pramlintide despite the AD subject initially showing an increase of plasma $A\beta1-42$ after the pramlintide injection. Part of $A\beta$ sequence, 17-23 amino acids, is shown to inhibit $\gamma$ secretase to generate more $A\beta$ (Li et al. 2010) as a mechanism to self-regulation. $\gamma$ secretase inhibition has been proposed to be a treatment for AD, but the clinical trials failed mainly due to its adverse events. We compared the sequences of $A\beta$ and amylin, and found that there are some homologies between the inhibitor sequence within $A\beta$ and the region of amylin. This indicates that amylin and its analogs can play a role of $\gamma$ secretase inhibitor that can be another mechanism of amylin treatment for AD. Pramlintide has a safety profile in the clinical use for diabetes.

Validation: We used the APP transgenic mice (Tg2576) to conduct amylin challenge test. Tg2576 mice have $A\beta$ deposits in the brain like the AD pathology. After intraperitoneal injection of amylin (20 mg/kg), Tg2576 mice (n=5) presented with the increase of serum $A\beta40$ and $A\beta42$ at 5 minutes, 1 hr and 24 hrs compared to the pre-injection levels of serum $A\beta40$ and $A\beta42$. However, the control mice (n=5) did not have these surges of serum $A\beta40$ and $A\beta42$ after the amylin challenge.

The data described herein provide novel assays and kits for diagnosis of AD and amnestic MCI. Based on these data, giving one dose of amylin subcutaneously or intravenously, and drawing blood before and after giving the amylin to measure plasma $A\beta42$ can be used in assays, methods, and kits to diagnose AD and amnestic MCI. AD patients or prodromal AD patients (amnestic MCI) with enormous $A\beta42$ in the brain will have an elevated level of $A\beta42$ in their plasma after the amylin injection compared to the baseline. Patients with other types of dementia or no AD will not have a rise in $A\beta42$ in their blood after the amylin injection because there is little or no $A\beta42$ in their brains. These assays and kits are similar to those used in glucose tolerance tests, which show abnormalities only in diabetic patients after the challenge of glucose is given. Amylin is already safely used in the treatment of type 2 diabetes. Accordingly, the assays and tests described herein can be used to reduce the cost to screen for AD risk, and are less invasive and more acceptable to AD patients than the lumbar puncture test currently used to obtain cerebral spinal fluid (CSF) or PET imaging.

In some embodiments, continuous injection of amylin can also be used in methods for treatment of AD.

TABLE 1

Correlations between Aβ and amylin in plasma

| Diagnoses | The controls N = 145 | Amnestic MCI N = 15 | Alzheimer's disease N = 40 |
|---|---|---|---|
| I. AGE, YEAR, MEAN ± SD* | 72.3 ± 8.0 | 75.7 ± 8.7 | 80.5 ± 8.1 |
| II. MMSE, MEAN ± SD* | 27.1 ± 2.6 | 26.4 ± 2.5 | 22.2 ± 3.3 |
| III. Aβ40 WITH AMYLIN IN PLASMA | r = +0.02, p = 0.83 | r = +0.58, p = 0.02 | r = +0.29, p = 0.06 |
| IV. Aβ42 WITH AMYLIN IN PLASMA | r = +0.06, p = 0.46 | r = +0.73, p = 0.001 | r = +0.52, p = 0.0004 |

Using ANOVA analysis, age and average Mini Mental State Exam (MMSE) scores in the subgroups of the controls, amnestic mild cognitive impairment (amnestic MCI) and Alzheimer's disease are compared.
*$p < 0.0001$.
Pearson analyses were performed to determine Coerrelation Coefficient between plasma A 40 or A 42 and amylin in different subgroups: the controls, amnestic MCI and Alzheimer's disease. P values for statistical significance are shown.

TABLE 2

Data of the levels of figure stick glucose and plasma Aβ

| Blood Measurements | Subjects | Pre-injection | Post 5' | Post 30' | Post 60' | Post 180' |
|---|---|---|---|---|---|---|
| Glucose, pM/L | Control | 115 | 108 | 115 | 114 | 149 |
|  | AD | 85 | 91 | 88 | 135 | 115 |
| Aβ1-40, pg/ml | Control | 148.4 | 178.4 | 150.4 | 110.5 | 100.8 |
|  | AD | 180.6 | 160.8 | 161.0 | 129.4 | 104.6 |
| Aβ1-42, pg/ml | Control | 29.9 | 26.0 | 27.5 | 21.7 | 10.6 |
|  | AD | 27.0 | 29.0 | 31.8 | 26.6 | 22.0 |

REFERENCES

Banks, W. A., and Kastin, A. J. (1998). Differential permeability of the blood-brain barrier to two pancreatic peptides: insulin and amylin. Peptides 19, 883-889.

Bennett, R. G., Hamel, F. G., and Duckworth, W. C. (2003). An insulin-degrading enzyme inhibitor decreases amylin degradation, increases amylin-induced cytotoxicity, and increases amyloid formation in insulinoma cell cultures. Diabetes 52, 2315-2320.

Geary, N. (1999). Effects of glucagon, insulin, amylin and CGRP on feeding. Neuropeptides 33, 400-405.

Olsson, M., Herrington, M. K., Reidelberger, R. D., Permert, J., and Arnelo, U. (2007). Comparison of the effects of chronic central administration and chronic peripheral administration of islet amyloid polypeptide on food intake and meal pattern in the rat. Peptides 28, 1416-1423.

Qiu, W. Q., Walsh, D. M., Ye, Z., Vekrellis, K., Zhang, J., Podlisny, M. B., Rosner, M. R., Safavi, A., Hersh, L. B., and Selkoe, D. J. (1998). Insulin-degrading enzyme regulates extracellular levels of amyloid beta-protein by degradation. J Biol Chem 273, 32730-32738.

Shen, Y., Joachimiak, A., Rosner, M. R., and Tang, W. J. (2006). Structures of human insulin-degrading enzyme reveal a new substrate recognition mechanism. Nature 443, 870-874.

I claim:

1. A method for inhibiting progression of Alzheimer's disease or amnestic mild cognitive impairment, the method comprising administering to a subject having Alzheimer's disease or amnestic mild cognitive impairment a therapeutically effective amount of an amylin or amylin analog, wherein the amylin analog has a sequence selected from the group consisting of SEQ ID NOs: 13-44; and obtaining a biological sample from the subject within 72 hours of said administering and measuring the amount or quantity of Aβ peptide in the biological sample.

2. The method of claim 1, wherein the administering is at least once a week.

3. The method of claim 1, wherein the administering is performed by systemic injection.

4. The method of claim 1, wherein the biological sample is obtained from the subject within 24 hours of said administering.

5. The method of claim 1, wherein the biological sample is a blood sample, a serum sample, or a plasma sample.

6. The method of claim 1, wherein the Aβ peptide is Aβ42 of SEQ ID NO: 2.

7. The method of claim 1, further comprising administering to the subject a cholinesterase inhibitor.

8. The method of claim 1, further comprising administering to the subject an N-methyl D-aspartate (NMDA) antagonist.

* * * * *